United States Patent [19]

Arnaud et al.

[11] Patent Number: 5,274,104

[45] Date of Patent: Dec. 28, 1993

[54] N-SUBSTITUTED HETEROCYCLIC DERIVATIVES USEFUL IN THE TREATMENT OF CARDIOVASCULAR DISORDERS

[75] Inventors: Joëlle Arnaud, Montpellier; Jean-Louis Assens, Grabels; Claude Bernhart, Saint Gély du Fesc; Bernard Ferrari, Les Matelles; Frédérique Haudricourt, Montpellier; Pierre Perreaut, Saint Gély du Fesc, all of France

[73] Assignee: Elf Sanofi, A French Corp., Paris, France

[21] Appl. No.: 901,145

[22] Filed: Jun. 19, 1992

[30] Foreign Application Priority Data

Jun. 21, 1991 [FR] France .................. 91 07685

[51] Int. Cl.$^5$ .................. A61K 31/415; A61K 31/42; C07D 233/54; C07D 257/04; C07D 271/06; C07D 271/08

[52] U.S. Cl. .................................. 548/252; 514/364; 514/381; 514/397; 514/398; 548/253; 548/132; 548/300.7; 548/301.1; 548/301.4; 548/301.7; 548/311.7; 548/313.7

[58] Field of Search .................. 548/300.7, 313.7, 252, 548/253, 132, 311.7, 301.1, 301.4, 301.7; 514/364, 381, 397, 398

[56] References Cited

U.S. PATENT DOCUMENTS

| 3,716,335 | 2/1973 | Ullman et al. | 548/300.7 |
| 3,770,763 | 11/1973 | Cusic et al. | 548/300.7 X |
| 3,872,117 | 3/1975 | Meiser et al. | 548/313.7 X |
| 4,544,754 | 10/1985 | Los | 548/300.7 |
| 4,614,535 | 9/1986 | Schmierer et al. | 71/92 |
| 4,719,222 | 1/1988 | Pinza et al. | 548/300.7 X |
| 4,723,989 | 2/1988 | Buck et al. | 71/92 |
| 4,726,835 | 2/1988 | Uemura et al. | 548/300.7 X |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,992,094 | 2/1991 | Alvarado et al. | 548/300.7 X |
| 5,011,935 | 4/1991 | Nakatani et al. | 548/313.7 |

FOREIGN PATENT DOCUMENTS

| 0144749 | 3/1984 | European Pat. Off. | 71/92 |
| 0207680 | 1/1987 | European Pat. Off. | 548/300.7 |
| 0253310 | 9/1987 | European Pat. Off. | 548/252 |
| 0324377 | 5/1989 | European Pat. Off. | 548/252 |
| 1445904 | 3/1969 | Fed. Rep. of Germany | 548/311.7 |

Primary Examiner—Floyd D. Higel
Attorney, Agent, or Firm—Bacon & Thomas

[57] ABSTRACT

The present invention relates to N-substituted heterocyclic derivatives of formula:

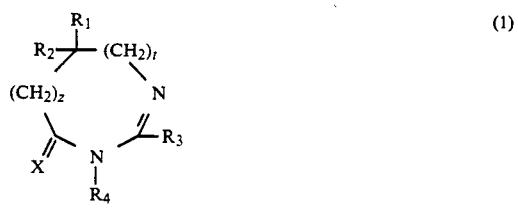

processes for their preparation, and pharmaceutical compositions which contain them. The compounds according to the invention are non-peptide compounds which oppose the action of angiotensin II. The compounds according to the invention are thus useful in the treatment of cardiovascular disorders such as hypertension and heart failure.

13 Claims, No Drawings

N-SUBSTITUTED HETEROCYCLIC DERIVATIVES USEFUL IN THE TREATMENT OF CARDIOVASCULAR DISORDERS

The present invention relates to N-substituted heterocyclic derivatives, their preparation and the pharmaceutical compositions which contain them.

The compounds according to the invention oppose the action of angiotensin II which is a hormone of formula:

H-Asp-Arg-Val-Tyr-Ile-His-Pro-Phe-OH

Angiotensin II is a powerful vasopressor agent which is the biologically active product of the reninangiotensin system: renin acts on the angiotensinogen of the plasma to produce angiotensin I, which is converted to angiotensin II by the action of angiotensin I conversion enzyme.

The compounds of the present invention are nonpeptide compounds which are antagonists of angiotensin II. By inhibiting the action of angiotensin II on its receptors, the compounds according to the invention especially prevent the increase in the blood pressure produced by the hormone-receptor interaction. They also have other physiological actions at the central nervous system level.

The compounds according to the invention are thus useful in the treatment of cardiovascular disorders such as hypertension or heart failure as well as in the treatment of central nervous system disorders and in the treatment of glaucoma and of diabetic retinopathy.

The subject of the present invention is compounds of formula:

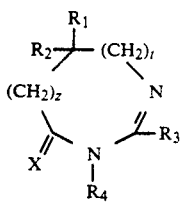
(1)

in which:

$R_1$ and $R_2$ each independently represent a $C_1$-$C_6$ alkyl, a $C_3$-$C_7$ cycloalkyl, a phenyl or a phenylalkyl in which the alkyl is $C_1$-$C_3$, the said alkyl, phenyl and phenylalkyl groups being unsubstituted or substituted by one or more halogen atoms or by a group chosen from a $C_1$-$C_4$ perfluoroalkyl, a hydroxyl or a $C_1$-$C_4$ alkoxy;

or $R_1$ and $R_2$ form together a group of formula =$CR'_1R'_2$, in which $R'_1$ represents hydrogen, a $C_1$-$C_4$ alkyl or a phenyl, and $R'_2$ represents a $C_1$-$C_4$ alkyl or a phenyl;

or $R_1$ and $R_2$ bonded together also represent either a group of formula —$(CH_2)_n$— or a group of formula —$(CH_2)_pY(CH_2)_q$—, in which Y is either an oxygen atom, or a sulphur atom, or a group CH substituted by a $C_1$-$C_4$ alkyl group, a phenyl group or a phenylalkyl group in which the alkyl is $C_1$-$C_3$, or a group in which $R_5$ represents a hydrogen, a $C_1$-$C_4$ alkyl, a phenylalkyl in which the alkyl is $C_1$-$C_3$, a $C_1$-$C_4$ alkylcarbonyl, a $C_1$-$C_4$ haloalkylcarbonyl, a $C_1$-$C_4$ polyhaloalkylcarbonyl, a benzoyl, an alpha aminoacyl or a N-protector group, or $R_1$ and $R_2$ bonded together with the atom of carbon to which they are bonded constitute an indane or an adamantane;

$R_3$ represents a hydrogen, a $C_1$-$C_6$ alkyl, which is unsubstituted or substituted by one or more halogen atoms; a $C_2$-$C_6$ alkenyl; a $C_3$-$C_7$ cycloalkyl; a phenyl; a phenylalkyl in which the alkyl is $C_1$-$C_3$, a phenylalkenyl in which the alkenyl is $C_2$-$C_3$, the said phenyl groups being unsubstituted or substituted one or more times by a halogen atom, a $C_1$-$C_4$ alkyl, a $C_1$-$C_4$ haloalkyl, a $C_1$-$C_4$ polyhaloalkyl, a hydroxyl or a $C_1$-$C_4$ alkoxy;

$R_4$ represents a group chosen from:

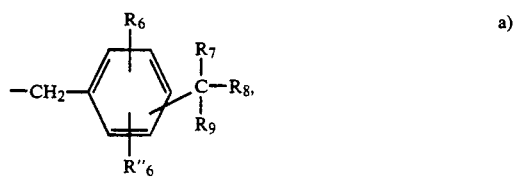
a)

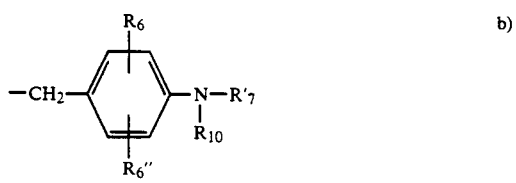
b)

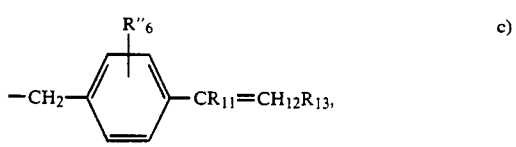
c)

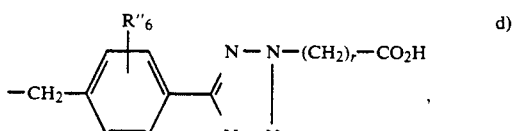
d)

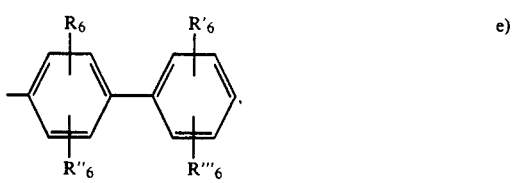
e)

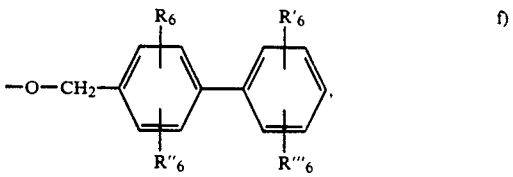
f)

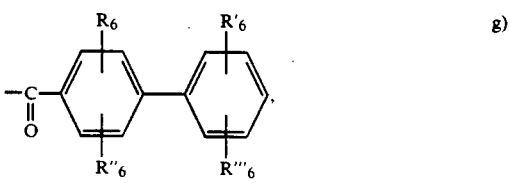
g)

-continued h) 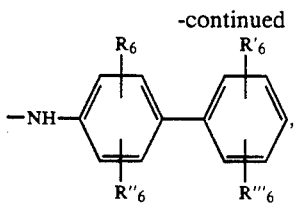

j) 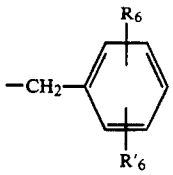

k) 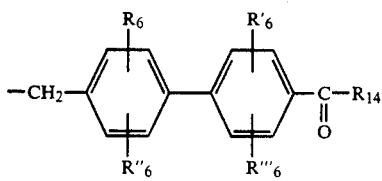

l) 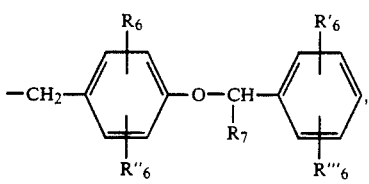

R''₆ and R'''₆ are similar or different and each independently represent hydrogen, a chlorine atom or a group chosen from a $C_1$–$C_6$ alkyl, a $C_1$–$C_4$ alkoxy, an amino or an aminomethyl;

R₆ and R'₆ are similar or different and each independently represent a hydrogen atom, a carboxy, an alkoxycarbonyl in which the alkoxy is $C_1$–$C_4$, a cyano, a 5-tetrazolyl, a 5-methyltetrazolyl or a 4H-5-oxo-1,2,4-oxadiazol-3-yl, or a 4H-3,5-dioxo-1,2,4-oxadiazol-2-yl, on condition that for the groups e, f, g, h, j, at least one of the substituents R₆ or R'₆ is different from hydrogen;

R₇ represents a $C_1$–$C_4$ alkyl or a group chosen from:

—(CH₂)ᵣ—CO₂H,  i)

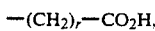 ii)

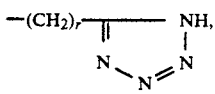 iii)

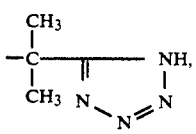 iv)

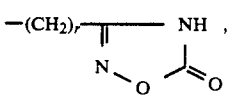 v)

-continued

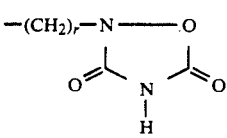 vi)

—(CH₂)ᵣ—CN  vii)
—OCOCH₃  viii)

R'₇ represents a $C_1$–$C_4$ alkyl or a group chosen from:

—(CH₂)ₛ—CO₂H,
—(CH₂)ᵣ—CN, $$-(CH_2)_r-\underset{NH}{\overset{\parallel}{C}}-OCH_3$$

(tetrazole structure with NH)

(dimethyl-substituted tetrazole with NH)

(oxadiazolone with NH)

(oxadiazolidinedione with NH)

R₈ is identical to R₇, or else R₈ represents hydrogen, a halogen atom, a $C_1$–$C_4$ alkyl, a $C_3$–$C_7$ cycloalkyl, a phenyl substituted by R'₆, a benzyl in which the phenyl is substituted by R'₆, a hydroxyl, a $C_1$–$C_4$ alkoxy, a cyano, a group OCOR₁₅ in which R₁₅ represents a $C_1$–$C_4$ alkyl, a $C_1$–$C_4$ haloalkyl or a phenyl substituted by R'₆:

R₉ is hydrogen or R₉ is identical to R₈, with the limitation that R₉ cannot be identical to R₇;

or R₈ and R₉ together with the carbon atom to which they are bonded constitute a $C_3$–$C_7$ cycloalkyl or a carbonyl group;

R₁₀ represents hydrogen, a $C_1$–$C_4$ alkyl, a $C_3$–$C_7$ cycloalkyl, a phenyl substituted by R'₆ or a benzyl whose phenyl is substituted by R'₆;

R₁₁ represents hydrogen, a $C_1$–$C_6$ alkyl, a phenyl, a carboxy, an alkoxycarbonyl in which the alkoxy is $C_1$–$C_4$, a 5-tetrazolyl or a 4H-5-oxo-1,2,4-oxadiazol-3-yl, or 4H-3,5-dioxo-1,2,4-oxadiazol-2-yl;

R₁₂ represents hydrogen, a $C_1$–$C_6$ alkyl, a cyano, a carboxy, an alkoxycarbonyl in which the alkoxy is $C_1$–$C_4$, a 5-tetrazolyl, a phenyl substituted by R'₆ or a benzyl whose phenyl is substituted by R'₆;

R₁₃ represents hydrogen, a $C_1$–$C_6$ alkyl, an alkoxycarbonyl in which the alkoxy is $C_1$–$C_4$, a phenyl substituted by R'₆, a benzyl whose phenyl is substituted by R'₆, a cyano, a carboxy, a 5-tetrazolyl, a 4H-5-oxo-1,2,4-oxadiazol-3-yl or a 4H-3,5-dioxo-1,2,4-oxadiazol-2-yl, on condition that R₁₁ and R₁₃ do not simultaneously represent one of the following groups: a carboxy, a 5-tetrazolyl, a 4H-5-oxo-1,2,4-oxadiazol-3-yl or a 4H-3,5-dioxo-1,2,4-oxadiazol-2-yl;

$R_{14}$ represents a $C_1$–$C_4$ carboxyalkyl, a phenyl or a carboxyphenyl;

p+q=m;

n is an integer of between 2 and 11;

m is an integer of between 2 and 5;

r represents 0, 1 or 2;

s represents 1 or 2;

X represents an oxygen atom or a sulphur atom;

z and t are zero or one is zero and the other represents 1; with the limitation that for the values a), b), k) and l) of $R_4$, $R_6$ represents hydrogen when $R_7$, $R'_7$ or $R_{14}$ contains either a carboxy group or a 5-tetrazolyl group or a 4H-5-oxo-1,2,4-oxadiazol-3-yl group or a 4H-3,5-dioxo-1,2,4-oxadiazol-2-yl group; and their salts.

When a compound according to the invention has an asymmetric carbon, the invention comprises the 2 optical isomers of this compound. The separation of the optical isomers can be carried out according to the methods described in "Synthesis of Optically Active alpha-aminoacids", R. M. Williams, Pergamon Press, 1989.

The salts of the compounds of formula (1) according to the present invention comprise those with inorganic or organic acids which allow a separation or a suitable crystallisation of the compounds of formula (1), such as trifluoroacetic acid, picric acid, oxalic acid or an optically active acid, for example a mandelic acid or a camphorsulphonic acid, and those which form pharmaceutically acceptable salts such as the hydrochloride, the hydrobromide, the sulphate, the hydrogen sulphate, the dihydrogen phosphate, the methanesulphonate, the maleate, the fumarate or the 2-naphthalenesulphonate.

The salts of the compounds of formula (1) also comprise the salts with organic or inorganic bases, for example the alkaline or alkaline-earth inorganic salts such as the sodium, potassium or calcium salts, the sodium and potassium salts being preferred, or with a tertiary amine, such as trometamol, or indeed the salts of arginine, of lysine or of any pharmaceutically acceptable amine.

According to the present description and in the claims which will follow, a halogen atom means a bromine, chlorine or fluorine atom; alkyl means a linear or branched hydrocarbon radical; N-protector group (also denoted by Pr) means a group used conventionally in the chemistry of peptides to allow a temporary protection of the amine function, for example a Boc, Z, Fmoc group or a benzyl group; esterified carboxy group means a labile ester under the appropriate conditions, as for example a methyl, ethyl, benzyl or tertiary butyl ester; α-amino acid group means a residue of a natural α-amino acid which carries no other functional groups than the amino and carboxy functions.

The compounds of formula (1) in which $R_1$ and $R_2$ bonded together represent a group —$(CH_2)n$ in which n is 4 or 5, are preferred compounds; the compounds of formula (1) in which $R_1$ and $R_2$ represent, the one a methyl and the other a cyclohexyl, are also preferred.

Likewise, the compounds of formula (1) in which $R_3$ represents a $C_1$–$C_6$ linear alkyl group are preferred compounds.

The compounds of formula (1) in which X represents an oxygen atom are also preferred compounds.

The compounds of formula (1) in which $R_4$ represents the group a) are preferred: very particularly preferred are the compounds (1) in which $R_4$ represents a group of formula:

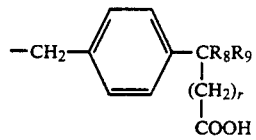

in which r, $R_8$ and $R_9$ have the meanings indicated above for (1).

Finally the compounds of formula (1) in which z=t=0 are preferred compounds.

The following abbreviations are used in the description and in the examples:

Et: ethyl nBu, tBu: n-butyl, tert-butyl

DMF: dimethylformamide

THF: tetrahydrofuran

DCM: dichloromethane

NBS: N-bromosuccinimide

DCC: dicyclohexylcarbodiimide

DIPEA: diisopropylethylamine

Ether: ethyl ether

TFA: trifluoroacetic acid

Z: benzyloxycarbonyl

Boc: tert-butoxycarbonyl

BOP: benzotriazolyloxytris(dimethylamino)phosphonium hexafluorophosphate

Fmoc: fluorenylmethyloxycarbonyl

AcOH: acetic acid

AcOEt: ethyl acetate

MeOH: methanol

DMAP: 4-(dimethylamino)pyridine

LDA: lithium diisopropylamide tetr: 5-tetrazolyl.

Another subject of the present invention is the process for preparing the compounds (1). The compounds (1) according to the invention in which $R_4$ has one of the values a), b), c), d), j), k) or l) are prepared according to the process described below and called process 1. The said process is characterised in that:

a1) a heterocyclic derivative of formula:

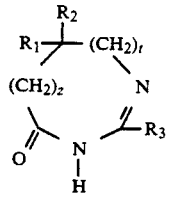

(2)

in which z, t, $R_1$, $R_2$ and $R_3$ have the meanings indicated above for (1) is reacted with a halide of formula:

Hal—$R'_4$     (3)

in which Hal represents a halogen atom, preferably bromine, and $R'_4$ represents either $R_4$ or a precursor group of $R_4$;

b1) optionally, the compound thus obtained, of formula:

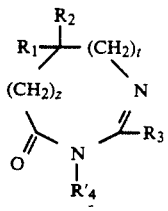

(4)

is treated with Lawesson's reagent [2,4-bis(4-methoxyphenyl)-1,3-dithia-2,4-diphosphetane-2,4-disulphide];

c1) the compound obtained in a1) or in b1), of formula:

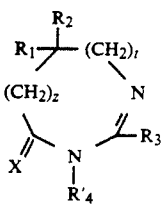

(5)

in which X represents an oxygen atom or a sulphur atom, is optionally treated in order to prepare the compound (1) by conversion of the $R'_4$ group to $R_4$.

Stage a1) of the process is carried out in an inert solvent such as DMF, DMSO or THF, in basic medium, for example in the presence of potassium hydroxide, sodium hydroxide, a metal alkoxide or a metal hydride.

Stage b1) is carried out by heating under nitrogen in a solvent such as toluene, according to the method described by M. P. Cava et al. (Tetrahedron, 1985, 41, 22, 5061).

The compounds (2) are prepared by known methods. For example, it is possible to use the method described by Jacquier et al. (Bull. Soc. Chim. France, 1971, (3), 1040-1051) and by Brunken and Bach (Chem. Ber., 1956, 89, 1363-1373) and to react an alkyl imidate with an amino acid or its ester, according to the following reaction scheme:

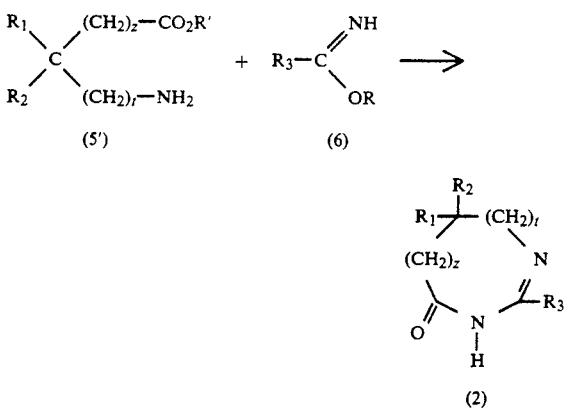

in which r represents a $C_1$-$C_4$ alkyl, R' represents hydrogen or a $C_1$-$C_4$ alkyl and $R_1$, $R_2$, $R_3$, z and t are as defined previously for (1).

This reaction is carried out in acid medium, by heating in an inert solvent such as xylene or toluene.

According to another operating mode, a compound (2), can be prepared by reaction in acid medium of an amino alkylamide (5") with an alkyl orthoester (10) according to the following reaction scheme:

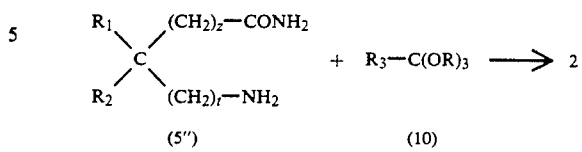

in which R represents a $C_1$-$C_4$ alkyl.

By using a procedure described by H. Takenaka et al. (Heterocycles, 1989, 29 (6), 1185-89), it is also possible to prepare the compound (2) by first reacting the derivative (5") with an acid halide of formula:

$$R_3-CO-Hal \quad (12)$$

in which Hal represents a halogen, preferably chlorine; cyclisation is carried out in basic medium.

The halogenated compounds $R'_4Hal$ (3) are known or prepared by known methods, for example the methods described in Patent Applications EP 324377 and W 91-12001.

When the compound (1) to be prepared possesses a carboxy group within the $R_4$ substituent, $R'_4$ contains an esterified carboxy group. When the compound (1) to be prepared possesses a tetrazolyl group within the $R_4$ substituent, $R'_4$ contains either a protected tetrazolyl, for example by a trityl group, or a cyano group which will be then replaced by a tetrazolyl group protected by a trityl. The conversion of $R'_4$ to $R_4$ is then carried out at stage c1) of the process.

In the particular case of the preparation of a $R_4$ group comprising a tetrazolyl, stage a1) can be carried out either with a $R_4Hal$ compound comprising a tetrazolyl group protected by a trityl or with a $R'_4Hal$ compound comprising a cyano, precursor of the tetrazole.

When the compound (1) to be prepared possesses a 4H-5-oxo-1,2,4-oxadiazol-3-yl group, the latter is prepared by one of the methods of the literature mentioned below:

M. A. Perez et al., Synthesis, 1983, 483.

A. R. Katritzky et al., Tetrahedron, 1965, 21, 1681-1692.

K. R. Rao et al., Heterocycles, 1988, 27, (3), 683-685.

G. Babu et al., J. Org. Chem., 1976, 41, (20), 3223-3237.

Thus, the substituent is obtained from the $C(OC_2H_5)=NCO_2CH_3$ group which itself is obtained from a carboxy group converted into a carboxamido group [R. J. Bergeron et al., J. Org. Chem., 1985, 50 (15), 2781].

When the compound (1) to be prepared possesses a 4H-3,5-dioxo-1,2,4-oxadiazol-2-yl group, the latter is prepared from a nitro group according to the method described by J. L. Kraus et al. in J. Het. Chem., 1982, 19, 971 or according to the method described by N. B. Vsevolozhakaya et al. in Zh. Org. Khim., 1971, 7 (5), 923-929.

The preparation of a compound $R'_4Hal$ useful for the synthesis of a compound (1) in which $R_4$ is the group a) can be carried out by one of the known methods, chosen by a person skilled in the art and adapted according to the nature of the substituents $R_6$, $R_6''$, $R_7$, $R_8$ or $R_9$ which enter into the composition of the group a).

Thus, the procedure described by J. Gyr in Chem. Ber., 1908, 41, 4321, allows the preparation of 2-(para-tolyl)phenylacetic acid ($R_4H$); the method described by M. E. Grundy et al. in J. Chem. Soc., 1960, 372–376 can also be used. An ester of this acid is prepared by a known process and then the corresponding halogenated derivative HalR'₄ (3), for example, by action of N-bromosuccinimide according to the process described in European Patent Application EP 324377.

It is also possible to prepare in the same manner compounds R₄H and R'₄Hal in which one and/or the other of the phenyl rings carries an R₆ and/or R'₆ and/or R"₆ substituent.

The ester of a 2-(para-tolyl)-2-alkylphenylacetic acid is obtained by alkylation of the ester of 2-(para-tolyl)-phenylacetic acid, for example by the action of an alkyl iodide and sodium hydride.

2,2-Diphenyl-2-(para-tolyl)acetic acid (R₄H) is prepared from benzilic acid and toluene according to the method described by A. Bistrzycki in Chem. Ber., 1901, 34, 3080. The ester is then prepared and then the halogenated derivative R'₄Hal by known methods.

3-(para-Tolyl)-3-phenylpropionic acid (R₄H) is prepared according to W. Karsten in Chem. Ber., 1893, 26, 1579–1583. It allows the preparation of the corresponding R'₄Hal compound.

The ethyl ester of 2-(para-tolyl)dihaloacetic acid is prepared according to R. N. McDonald et al. in J. Org. Chem., 1980, 45 (15), 2976–2984; it allows the preparation of the corresponding halogenated derivative.

para-Methylbenzyl cyanide is used for the preparation of 5-(para-methylbenzyl)tetrazole by action of tributyltin azide, or of sodium azide. Trityl 5-(paramethylbenzyl)tetrazole (R'₄H) is then prepared by action of trityl chloride.

It is also possible to prepare a 2-monoalkyl-, 2,2-dialkyl- or 2-cycloalkyl-para-methylbenzyl cyanide according to J. Org. Chem. 1969, 34, 227, by action of an alkyl bromide or cycloalkyl bromide on paramethylbenzyl cyanide. This compound can be used to prepare the corresponding acid and then its ester by known methods. It can also be used for the conversion of the cyano group to tetrazolyl by action of tributyltin azide according to a known method.

2,2-Dibenzyl-para-methylbenzyl cyanide is obtained by the action of a benzyl halide, for example benzyl bromide, on para-methylbenzyl cyanide, in basic medium; the corresponding halide derivative (R'₄Hal) is then prepared.

In a similar manner, 1-cyano-1-(4-methylphenyl)cyclohexane is obtained by the action of 1,5-dibromopentane on para-methylbenzyl cyanide, according to the operating procedure described by J. Org. Chem. 1971, 36 (9), 1308.

In order to prepare an alkyl para-tolyl cyanide, it is necessary to proceed by different known successive stages. Thus, for example by operating according to Tetrahedron, 1959, 7, 236–240, the ethyl ester of 3-(para-tolyl)-2-cyano-2-butenoic acid is prepared; this is converted into the ethyl ester of 3-methyl-3-(paratolyl)-2-cyanobutanoic acid, according to J. Am. Chem. Soc., 1957, 79, 4487 and then into the corresponding acid; the method described in Japanese Patent Application, Japan Kokai 78-124248 is then used to prepare 2-(para-tolyl)-2-methylpropyl cyanide. Optionally, this product can be converted into 2-(paratolyl)-1,1,2-trimethylpropyl cyanide by the action of methyl iodide in the presence of lithium diisopropylamide.

The compounds of formula (1) for which R₄ represents the group a), in which R₇ represents —(CH₂)-COOH, allow the preparation of the compounds of formula (1) in which R₇ represents —(CH₂)ᵣ—CONHOH by the action of thionyl chloride and of hydroxylamine.

In order to prepare a compound R₄Hal in which the group R₄ represents the group a), in which the substituent R₈ is a hydroxyl or a C₁–C₄ alkoxy and R₇ and R₉ have the values indicated above for (1), the method described by A. McKenzie et al. in J. Chem. Soc., 1934, 1070–1075 can be used. In order to prepare the compounds of formula (1) in which R₈ is an acetoxy group R₁₅COO, the acylation reaction can be carried out either on a compound of formula (1), in which R₈ is a hydroxyl or on a compound R'₄H, in which R₈ is a hydroxyl.

A compound R'₄Hal useful for the synthesis of a compound (1) in which R₄ is the group b) is obtained from a compound R'₄H. For example, to obtain a group R₄ in which R₁₀ is a phenyl and R'₇ is CH₂CO₂H N-phenyl-N-(para-tolyl)trifluoroacetamide is used as compound R'₄H. This is prepared from N-(paratolyl)-phenylamine and trifluoroacetic anhydride. The N-(para-tolyl)phenylamine itself is prepared according to C. Izard-Verchere et al. in Chim. Therap., 1971, 5, 346–351. At stage c1) of the process, the amine protective group, the trifluoromethylcarbonyl, is replaced by hydrogen in basic medium and then a tert-butyl acetate group is introduced by the action of tert-butyl bromoacetate; it is then converted into the methylcarboxylic group in order to obtain the expected compound (1). This method is varied according to the nature of the substituents (R₆, R"₆, R'₇ and R₁₀) belonging to R₄.

Thus, in order to obtain a group R₄ in which R₇ is a cyano and R₁₀ is a phenyl, the method described by J. R. Robinson in Can. J. Chem., 1954, 32, 901–905 is used; the cyano can then be converted into tetrazolyl according to the usual methods. A compound of formula (1), in which R₄ is the group b) with R'₇ representing a cyano group, can be treated with potassium cyanide according to the method described by A. Bonetti et al. in J. Org. Chem., 1972, 27 (21), 3352, in order to prepare a compound of formula (1) in which R₇ represents —C(=NH)OCH₃; the method of M. A. Perez et al., Synthesis, 1983, 483 can then be used in order to convert R'₇ to oxadiazolyl.

In order to prepare a compound (1) in which R₄ is the group c), it is possible either to introduce the double bond in the group R'₄ or to introduce it only at stage c1) of the process by conversion of the precursor group R'₄.

Thus, it is possible, for example, to use 4-(bromomethyl)benzonitrile as compound R'₄Hal; stage c1) of the process then comprises the following successive stages: the nitrile is converted to aldehyde by the action of a reducing agent such as Raney nickel and then phenylacetic acid is reacted in basic medium, according to the process described by H. E. Zimmerman et al., J. Am. Chem. Soc. 1959, 81, 2086. In the compound (1) thus obtained, the group R₄ is the 2-(para-tolyl)-1-phenylacrylic acid radical.

It is also possible to use the H. E. Zimmerman reaction to prepare a compound R'₄Hal such as the tert-butyl ester of 2-[4-(bromomethyl)phenyl]-1-phenylacrylic acid.

According to another method of preparation, when the group R₄ is c) comprising a tetrazolyl, it is possible to prepare the precursor comprising the cyano group, for example by the action of an aldehyde on para-methylbenzyl cyanide (Ivanov et al., Compt. Rend. Acad. Bulgar. Sci., 1957, 10 (1), 53). Thus, when the aldehyde is pivalaldehyde, 4,4-dimethyl-2-(para-tolyl)2-pentenenitrile is obtained. The compound R'$_4$Hal then obtained by the usual conversions is 1-(para-bromomethylphenyl)-3,3-dimethyl-1-(1-trityl5-tetrazolyl)-1-butene.

Another method of preparation of the compound R'$_4$H in reacting an alkylphosphonate cyanide with para-tolualdehyde or with a para-tolyl alkyl ketone according to the reaction described in Chem. Pharm. Bull., 1980, 1394. The preparation of paratolylalkylacetone is described in J. Am. Chem. Soc., 1950, 4169 and the preparation of alkylphosphonate cyanide is described by E. Schaumann et al. in Synthesis, 1983, 449–450.

According to another process, in order to prepare a compound R'$_4$H which makes it possible to obtain a compound of formula (1) in which R$_4$ is the group c) with R$_{12}$ and R$_{13}$ representing a carboxy, an alkoxycarbonyl in which the alkoxy is C$_1$–C$_4$ or a 5-tetrazolyl, an appropriate derivative of malonic acid can be reacted with a compound of formula:

$$CH_3 \text{—} \underset{R_{11}}{\overset{R''_6}{\text{—C}_6H_4\text{—C=Y}}}$$

in which Y represents an oxygen or a NH group and R''$_6$ and R$_{11}$ have the natures indicated above for (1).

The preparation of a compound R'$_4$Hal, in which R'$_4$ is the group d), is carried out from paramethylbenzonitrile which makes it possible to obtain 5-(para-tolyl)tetrazole by the action of an azide, for example sodium azide, according to the usual methods.

When the group R$_4$=d) consists of a carboxyl or carboxylalkyl function, the preparation of the compound (1) can be carried out by substituting the tetrazole by the appropriate function in a final stage (stage c1) of the process.

The preparation of a compound R'$_4$Hal in which R'$_4$ is the group k) is carried out according to the procedure described by E. Burker in Bull. Soc. Chim. Fr., 1888, 449 and Weizmann et al. in Chem. Ind., 1940, 402.

The preparation of a compound R'$_4$Hal in which R'$_4$ is the group l) is carried out according to the procedure described in International Patent Application WO 91-12001.

Alternatively, the preparation of a compound (1) which carries a substituent R$_4$ of formula g) is carried out by using the process 1 of the invention in which, in stage a1), the compound R'$_4$Hal is replaced by a compound R'$_4$OH(3'). The compound R'$_4$OH is prepared by known methods. Thus, for example, 2-(tert-butoxycarbonyl)-4-biphenylcarboxylic acid is prepared according to S. Cacchi et al. in Chem. Ind., 1986, 286.

The compounds of formula (1) can be prepared according to another process called process 2 which is also a subject of the present invention. This process is characterised in that:

a2) an amino acid of formula:

$$\underset{R_2}{\overset{R_1}{\diagdown}} \underset{(CH_2)_z}{\overset{(CH_2)_t\text{—NHPr}}{\diagup}} C \diagdown COOH \qquad (7)$$

in which z, t, R$_1$ and R$_2$ have the meanings indicated above for (1) and the amine function of which is protected by the group Pr, is reacted with a derivative of formula:

$$H_2N\text{—}R'_4 \qquad (8)$$

in which R'$_4$ represents either R$_4$ or a precursor group of R$_4$;

b2) after deprotection of the amine, the compound thus obtained of formula:

$$\underset{R_2}{\overset{R_1}{\diagdown}} \underset{(CH_2)_t\text{—NH}_2}{\overset{(CH_2)_z\text{—C(=O)—NH—R'}_4}{\diagup}} C \qquad (9)$$

is then treated with an alkyl ortho ester of formula R$_3$C(OR)$_3$ (10) in which R$_3$ has the meaning indicated above for (1) and R is a C$_1$–C$_4$ alkyl;

c2) optionally, the compound thus obtained of formula:

(4)

is treated with Lawesson's reagent [2,4-bis(4-methoxyphenyl)-1,3-dithia-2,4-diphosphetane-2,4-disulphide];

d2) the compound thus obtained in b2) or in c2) of formula:

(5)

is then treated under conditions suitable for the preparation of compound (1) by conversion of the group R'$_4$ to group R$_4$.

The compounds (7) are known or prepared by known methods (Chemistry of the Amino Acids, Greenstein and Winitz, John Wiley publ., 1961, vol. I, 697). Optionally, these compounds can be obtained optically pure by using methods for asymmetric synthesis or for resolution of the racemic mixture, such as described in "Synthesis of Optically Active alpha-aminoacids" R. M. Williams, Pergamon Press, 1989.

The compounds (8) are known or prepared according to known methods. Stage a2) is carried out under the usual conditions for the coupling of an acid with an amine, for example in the presence of BOP and of DIPEA.

Stage b2), which is the cyclisation of compound (9) in the presence of (10), is carried out according to Jacquier et al. (Bull. Soc. Chim. France, 1971, (3), 1040-1051) and according to Brunken and Bach (Chem. Ber., 1956, 89, 1363-1373).

In the description below, the process comprising stages a2) to d2) is called process (2).

According to a variant of process (2), at stage b2), it is possible to optionally isolate an intermediate (9') of formula:

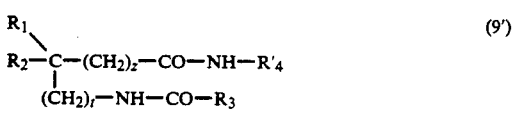

to then prepare the compound (4) by cyclisation in acid medium.

According to another variant of process (2) and in order to prepare a compound (1) in which z=0 and $R_1R_2$ represents a group $=CR'_1R'_2$, an amino acid of formula:

can be reacted in acid medium with an aldehyde or a ketone of formula:

in which $R'_1$ and $R'_2$ have the meanings given above for (1) and then, by the action of compound (8), a compound of formula:

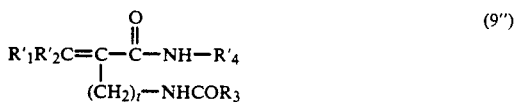

is obtained.

The cyclisation of this compound in acid medium leads to compound (4).

In a preferential manner, process (2) is used for the preparation of compounds (1) in which $R_4$ represents one of the groups e), f) or h).

For the preparation of a compound $R'_4NH_2$ (8) in $R'_4$ is a substituted biphenyl, converted into $R_4=e$) at stage c2), the procedure described by J. Witte et al. in J. Org. Chem., 1972, 37 (18), 2849 is used.

When $R_4$ is the group f), the preparation of $R'_4NH_2$ is carried out according to A. F. McKay et al., Can. J. Chem., 1960, 38, 343.

Finally, when $R_4$ is the group h), the preparation of $R'_4H$ is carried out according to S. A. Glover et al., J. Chem. Soc., Perkin I, 1981, 842; $R'_4NH_2$ is then prepared according to J. Witte et al., J. Org. Chem., 1972, 37 (18), 2849.

The compounds (1) according to the invention, in which $R_1$ and $R_2$ bonded together represent a group of formula $—(CH_2)_pY(CH_2)_q—$, in which Y is a group NH, can be prepared by catalytic hydrogenolysis of a corresponding compound (1) in which Y is a group $N—R_5$, $R_5$ being a benzyl.

The affinity of the products according to the invention for the angiotensin II receptors was studied by a test for binding of angiotensin II labelled with iodine 125 at membranal receptors of rat liver. The method used is that described by S. Keppens et al. in Biochem. J., 1982, 208, 809-817.

The $IC_{50}$: concentration which gives 50% of displacement of the labelled angiotensin II, bonded specifically to the receptor, is measured. The $IC_{50}$ of the compounds according to the invention is lower than $10^{-6}M$.

Furthermore, the angiotensin II antagonistic effect of the products according to the invention was observed in different animal species in which the renin-angiotensin system was activated beforehand (C. Lacour et al., J. Hypertension, 1989, 7 (suppl. 2), 33-p. 35).

The compounds according to the invention are active after administration by different routes, especially orally.

No sign of toxicity was observed with these compounds at the pharmacologically active doses.

Thus the compounds according to the invention can be used in the treatment of various cardiovascular disorders, especially hypertension or heart failure, as well as in the treatment of glaucoma, diabetic retinopathies and various disorders of the central nervous system, memory deficiencies or Alzheimer's disease, for example.

Another subject of the present invention is pharmaceutical compositions containing an effective dose of a compound according to the invention or of a pharmaceutically acceptable salt thereof and suitable excipients. The said excipients are chosen according to the pharmaceutical form and the desired method of administration.

In the pharmaceutical compositions of the present invention for oral, sublingual, subcutaneous, intramuscular, intravenous, topical, intratracheal, intranasal, transdermal or rectal administration, the active substances of formula (1) above, or their optional salts, can be administered in a unit form of administration, mixed with conventional pharmaceutical carriers, to animals or to human beings for the prevention or the treatment of the above disorders or diseases. The appropriate unit forms of administration comprise the oral forms such as tablets, gelatin capsules, powders, granules and oral solutions or suspensions, the sublingual, oral, intratracheal or intranasal forms of administration, the subcutaneous, intramuscular or intravenous forms of administration and the forms for rectal administration. For topical application, the compounds according to the invention can be used in creams, ointments or lotions.

In order to obtain the desired prophylactic or therapeutic effect, the dose of active substance can vary between 0.01 and 50 mg per kg of body weight and per day.

Each unit dose can contain from 0.1 to 1,000 mg, preferably from 1 to 500 mg, of active ingredients in combination with a pharmaceutical carrier. This unit dose can be administered 1 to 5 times per day, so as to administer a daily dosage of 0.5 to 5,000 mg, preferably from 1 to 2,500 mg.

When a solid composition is prepared in the form of tablets, the principal active ingredient is mixed with a pharmaceutical vehicle such as gelatin, starch, lactose, magnesium stearate, talc, gum arabic or similar. Tablets can be coated with sucrose, a cellulose derivative or other appropriate materials or can even be treated so that they have a prolonged or delayed activity and that they release a predetermined quantity of the active substance in a continuous manner.

A preparation in gelatin capsules is obtained by mixing the active ingredient with a diluent and by pouring the mixture obtained into soft or hard gelatin capsules.

A preparation in the form of syrup or of elixir or for administration in the form of drops can contain the active ingredient in conjunction with a sweetener, preferably low-calorie, methylparaben and propylparaben as antiseptic, as well as a flavouring agent and an appropriate colorant.

Water-dispersible powders or granules can contain the active ingredient mixed with dispersing agents or wetting agents, or suspending agents, such as polyvinylpyrrolidone, likewise with sweeteners or flavour regulators.

For rectal administration, suppositories are used which are prepared with binders which melt at rectal temperature, for example cocoa butter or polyethylene glycols.

For parenteral administration, aqueous suspensions, isotonic saline solutions or sterile and injectable solutions are used which contain pharmacologically compatible dispersing and/or wetting agents, for example propylene glycol or butylene glycol.

The active substance can be formulated also in the form of microcapsules, optionally with one or more carriers or additives.

The compositions of the present invention can contain, besides the products of formula (1) above or one of the pharmaceutically acceptable salts thereof, other active substances such as, for example, tranquillisers or other medicinal products which can be used in the treatment of the disorders or diseases indicated above.

Thus, the subject of the present invention are pharmaceutical compositions which contain several active substances in combination of which one is a compound according to the invention and the other(s) can be a beta-blocker, a calcium antagonist, a diuretic, a nonsteroidal antiinflammatory or a tranquilliser.

The examples which follow illustrate the invention without, however, limiting it. In these examples, the following abbreviations are used:

RT signifies room temperature, $KHSO_4$—$K_2SO_4$ signifies an aqueous solution containing 16.6 g of potassium bisulphate and 33.3 g of potassium sulphate per liter.

The melting points (m.p.) are given in degrees Celsius, except when otherwise indicated; they were measured without recrystallisation of the product.

The purity of the products is checked by thin layer chromatography (TLC) or by HPLC. The products are characterised by their melting point or by their NMR spectrum recorded at 200 MHz in deuterated DMSO, the internal reference being tetramethylsilane.

The following are used in the interpretation of NMR spectra:
s singlet
b.s. broad singlet
d doublet
t triplet
q quadruplet
quint quintuplet
sext sextuplet
m unresolved bands or multiplet
NOE effect signifies Nuclear Overhauser Effect.

In each of the examples, the nature of the substituent $R_4$ of the compound (1) prepared indicated.

Except when otherwise indicated, the compounds which have 1 or more asymmetric carbon atoms are obtained in the form of racemates or of a mixture of diastereoisomers.

EXAMPLE 1

2-[4-((2-n-Butyl-5-oxo-4-Spirocyclopentane-2-imidazolin-1-yl)methyl)phenyl]phenylacetic acid.

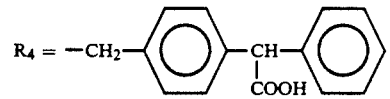

A) 2-(para-Tolyl)phenylacetic acid.

This acid is prepared from mandelic acid by the action of toluene according to the operating procedure described by J. Gyr in Chem. Ber., 1908, 41, 4308–4322. After crystallisation from an ether-hexane mixture, a product is obtained which contains, according to its NMR spectra, about 15% of 2-(ortho-tolyl)phenylacetic acid.

m.p.=b 100°–105° C.

B) tert-Butyl ester of 2-(para-tolyl)phenylacetic acid.

12 g of the acid obtained above are dissolved in 55 ml of dichloromethane and 5.3 ml of oxalyl chloride are added dropwise at 0° C. and the mixture is then left stirring for 5 hours at RT. The reaction mixture is then concentrated under vacuum and then evaporated twice with benzene. The residue obtained is dissolved in 150 ml of THF, 6.9 g of potassium tert-butoxide are added, at 0° C., and the mixture is then stirred for 1 and a half hours at RT. The residue is concentrated under vacuum to half its volume and is then taken up in a water-ether mixture; the ether phases are separated and then washed with a saturated solution of sodium chloride, dried over sodium sulphate and concentrated under vacuum. After chromatography on silica, 7.90 g of the expected product, identified by its NMR and IR spectra, are obtained.

C) tert-Butyl ester of 2-(para-(bromomethyl)phenyl)-phenylacetic acid.

3.7 g of the ester obtained above are dissolved in 150 ml of carbon tetrachloride and treated with 2.33 g of N-bromosuccinimide in the presence of 200 mg of benzoyl peroxide, at reflux, under U.V. irradiation for 1 hour. The succinimide formed is removed by filtration and then the filtrate is concentrated. The brominated derivative is obtained in the form of a red oil.

D) 2-(n-Butyl)-4-spirocyclopentane-2-imidazolin-5-one.

The ethyl ester of 1-aminocyclopentanecarboxylic acid is prepared according to Adkins and Billica (J. Amer. Chem. Soc., 1948, 70, 3121–3125).

Ethyl valerimidate is prepared according to MacElvain (J. Amer. Chem. Soc., 1942, 64, 1825–1827), released from its hydrochloride by the action of potassium carbonate and extraction by DCM.

The ethyl ester of 1-aminocyclopentane carboxylic acid (1.57 g) and the valerimidate (1.56 g) are dissolved in 12 ml of xylene containing 6 drops of acetic acid. After 6 and a half hours of heating at reflux, the reaction mixture is concentrated under vacuum and then the residue is chromatographed on silica gel by eluting with a chloroform/methanol/acetic acid (94/4/2; v/v/v) mixture. The fraction containing the expected product is evaporated several times in the presence of xylene and then benzene to remove the acetic acid. 1.91 g of product are obtained in the form of a thick oil.

IR (CHCl₃): 1720 cm⁻¹: C=O, 1635 cm⁻¹: C=N

Note: the fact that the band between 1500 and 1600 cm⁻¹ is not seen indicates that, in the chloroform solution, the product is a 5-imidazolinone.

NMR: 0.92 ppm: t: 3 H: CH₃(nBu), 1.35 ppm: sext: 2 H: CH₃—CH₂—, 1.50–1.93 ppm: m: 10 H: CH₃—CH₂CH₂ and cyclopentane, 2.33 ppm: t: 2 H: CH₃—CH₂—CH₂—CH₂—, 10.7 ppm: b.s.: NH mass spectrum: MH+: 195.

In order to prepare the hydrochloride of 2-(n-butyl)-4-spirocyclopentane-2-imidazolin-5-one, 8.5 g of this compound are dissolved in 100 ml of isopropanol and 3.7 ml of concentrated hydrochloric acid (d=1.18) are added dropwise. The mixture is made homogeneous by heating for a few minutes at 70° C. and then is cooled to 15° C. The crystals formed are filtered off, washed with isopropanol and then dried.

E) tert-Butyl ester of 2-[4-((2-n-butyl-5-oxo-4-spirocyclopentane-2-imidazolin-1-yl)methyl)phenyl]-2-phenylacetic acid.

800 mg of the product prepared in stage D are dissolved in 4 ml of DMF and 240 mg of sodium methoxide are added and then, after 15 minutes, 2.16 g of the product prepared in stage C, dissolved in 3 ml of DMF are added and the mixture is then heated for 3 and a half hours at 40° C. The reaction mixture is taken up in a water-ethyl acetate mixture, the organic phase is separated off and then rewashed with a saturated solution of sodium chloride and evaporated under vacuum. The residue is chromatographed on silica by eluting with a toluene-ethyl acetate mixture. 320 mg of the expected product are obtained.

IR (CHCl₃): 1710–1720 cm⁻¹: C=O: imidazolinone and ester, 1625 cm⁻¹: C=N imidazolinone NMR: 7.30–6.90 ppm: m: 9 H: aromatic, 4.90 ppm: s: 1 H: CH—CO₂(tBu), 4.55 ppm: s: 2 H: N-CH—C₆H₄, 2.20 ppm: t: 2 H: CH₃—CH₂—CH₂—CH₂—, 1.6–1.8 ppm: m: 8 H: cyclopentane, 1.20 ppm: quint: 2 H: CH₃—CH₂—CH₂—, 1.15 ppm: s: 9 H: (tBu), 1.10 ppm: sext: 2 H: CH₃—CH₂—, 0.75 ppm: t: 3 H: CH₃(nBu).

F) 2-[4-((2-n-Butyl-5-oxo-4-spirocyclopentane-2-imidazolin-1-yl)methyl)phenyl]-2-phenylacetic acid.

The product obtained in the above stage is treated with 4 ml of TFA in 3 ml of DCM for 45 minutes at 25° C. After evaporation under vacuum, the residue is treated with hexane, a precipitate forms. The solid obtained is chromatographed on silica by eluting with an AcOEt/MeOH/AcOH (97/3/0.3; v/v/v) mixture. 110 mg of the expected product are obtained. m.p.=146°–148° C.

mass spectrum: MH+ =419

NMR 7.10–7.40 ppm: m: 9 H: aromatic, 5.05 ppm: s: 1 H: CH—CO₂H, 4.65 ppm: s: 2 H: N-CH₂—C₆H₄, 2.30 ppm: t: 2 H: CH₃—CH₂—CH₂—CH₂, 1.60–2 ppm: m: 8 H: cyclopentane, 1.50 ppm: quint: 2 H: CH₃—CH₂—CH₂—CH₂, 1.25 ppm: sext: 2 H: CH₃—CH₂—CH₂—CH₂, 0.80 ppm: t: 3 H: CH₃(nBu).

EXAMPLE 2

2-[4-((2-n-Butyl-5-oxo-4-spirocyclopentane-2-imidazolin-1-yl)methyl)phenyl]-2-phenylpropionic acid.

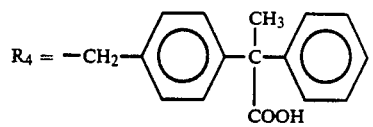

A) tert-Butyl ester of 2-(para-tolyl)-2-phenylpropionic acid.

5.9 g of tert-butyl ester of 2-(para-tolyl)-2-phenylacetic acid, prepared in Example 1 stage B, are dissolved in 80 ml of THF and 3.15 ml of methyl iodide are added at 0° C. and then 1.2 g of 50% sodium hydride in oil. After stirring overnight at RT, the reaction mixture is diluted with 300 ml of ethyl acetate and then 50 ml of water. The organic phase is separated, rewashed with a saturated solution of sodium chloride, dried over sodium sulphate and then concentrated under vacuum. The residue is chromatographed on silica by AcOEt/hexane. 4.7 g of the expected product are obtained in the form of an oil identified by its IR and NMR spectra.

B) tert-Butyl ester of 2-(para-bromomethyl)phenyl-2-phenylpropionic acid.

2.96 g of the ester obtained above are dissolved in 120 ml of carbon tetrachloride and treated with 1.78 g of NBS, in the presence of benzoyl peroxide, for 1 hour at reflux. The succinimide formed is removed by filtration and then the filtrate is evaporated under vacuum. 3.7 g of the expected product identified by its NMR spectra are obtained.

C) tert-Butyl ester of 2-[4-((2-n-butyl-5-oxo-4-spirocyclopentane-2-imidazoline-1-yl)methyl)phenyl]-2-phenylpropionic acid.

500 mg of 2-imidazolin-5-one, prepared in Example 1, stage D, dissolved in 5 ml of DMF, are added to 120 mg of 80% sodium hydride in oil, suspended in 4 ml of DMF. After 15 minutes, 1.02 g of the brominated derivative, prepared in the preceding stage, dissolved in 5 ml of DMF are added and the mixture is left stirring at RT for 2 hours. The reaction mixture is diluted with 100 ml of AcOEt and then 25 ml of water. The organic phase is separated off, washed with a saturated solution of sodium chloride, dried over sodium sulphate and then concentrated under vacuum. The residue is chromatographed on silica by eluting with a AcOEt-toluene mixture. 550 mg of the expected product are obtained.

IR (CHCl₃): 1720–1715 cm⁻¹: C=O: imidazolinone and ester, 1625 cm⁻¹: C=N imidazolinone NMR: 1.95 ppm: s: 3 H: CH—C—CO₂tBu D) 2-[4-((2-n-Butyl-5-oxo-4-spirocyclopentane-2-imidazolin-1-yl)methyl)phenyl]-2-phenylpropionic acid.

530 mg of the ester obtained in the preceding stage are treated for 45 minutes with 5 ml of TFA in 4 ml of DCM. After concentrating under vacuum, the residue is taken up in an ether-hexane mixture. After leaving overnight at 0° C., the crystals obtained are filtered off, washed with hexane and then dried under vacuum. 460 mg of the expected product are obtained.

m.p.=118°–120° C.

NMR: 7.0–7.30 ppm: m: 9 H: aromatic, 4.75 ppm: s: 2 H: N-CH₂—C₆H₄—, 2.50 ppm: t: 2 H: CH₃—CH₂—CH₂—CH₂—, 1.60–1.95 ppm: m: 11 H: cyclopentane+CH₃—C—CO₂H, 1.40 ppm: quint: 2 H: CH₃—CH₂—CH₂—CH₂—, 1.20 ppm: sext: 2 H: CH₃—C$\underline{H_2}$—C$\underline{H_2}$—CH₂, 0.70 ppm: t: 3 H: CH₃(n-Bu).

EXAMPLE 3

3-[4-((2-n-Butyl-5-oxo-4-spirocyclopentane-2-imidazolin-1-yl)methyl)phenyl)-3-phenylpropionic acid.

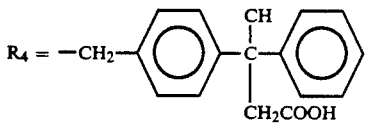

A) 3-(para-Tolyl)-3-phenylpropionic acid.

This acid is prepared according to Karsten (Chem. Ber., 1893, 26, 1579–1583).

B) tert-Butyl ester of 3-(para-tolyl)-3-phenylpropionic acid.

5 g of the acid prepared above are dissolved in 30 ml of DCM; 2 ml of oxalyl chloride are added at 0° C. and the mixture is left stirring for 3 hours at RT. The reaction mixture is evaporated to dryness and then reevaporated twice with benzene. The residue is dissolved in 30 ml of THF; 2.9 g of potassium tert-butoxide are added at 0° C. and the mixture is stirred for 1 hour at RT. 150 ml of ether and 50 ml of water are then added and then the organic phase is washed with a saturated solution of sodium chloride, dried over sodium sulphate and concentrated under vacuum. The expected product is obtained in the form of an oil which slowly crystallises (yield 67%).

m.p.=45° C.

The product is identified by its IR and NMR spectra.

C) tert-Butyl ester of 3-(4-(bromomethyl)phenyl)-3-phenylpropionic acid.

200 mg of benzoyl peroxide and 2.49 g of NBS are added to 4.1 g of the preceding ester dissolved in 150 ml of carbon tetrachloride and the mixture is taken to reflux for 2 hours under U.V. radiation. After filtration of the succinimide, the filtrate is concentrated under vacuum. Analysis of the NMR spectrum shows that a dibrominated derivative is also formed, namely the tert-butyl ester of 3-bromo-3-(4-(bromomethyl)phenyl)-3-phenylpropionic acid.

D) tert-Butyl ester of 3-[4-((2-n-butyl-5-oxo-4-spirocyclopentane-2-imidazolin-1-yl)methyl)phenyl]-3-phenylpropionic acid and tert-butyl ester of 3-[4-((2-n-butyl-5-oxo-4-spirocyclopentane-2-imidazolin-1-yl)methyl)phenyl]-3-phenylacrylic acid.

The mixture of compounds obtained in the preceding stage is added to 2-n-butyl-4-spirocyclopentane-2-imidazolin-5-one, prepared in Example 1, stage D. The reaction is carried out in DMF in the presence of sodium hydride. The product obtained is a mixture which comprises ⅔ of the ester of the propionic acid and ⅓ of the ester of the acrylic acid.

NMR: ester of the propionic acid: 4.40 ppm: t: 1 H: —C$\underline{H}$—CH₂—, 3.0 ppm: d: 2 H: —CH—C$\underline{H_2}$—, ester of the acrylic acid: 6.40 ppm: s: H: ethylenic E) 3-[4-((2-n-Butyl-5-oxo-4-spirocyclopentane-2-imidazolin-1-yl)methyl)phenyl]-3-phenylpropionic acid.

The mixture of tert-butyl esters prepared in the preceding stage is hydrolysed by the action of trifluoroacetic acid in DCM according to the method described previously.

300 mg of the mixture of acids thus obtained are dissolved in 10 ml of ethanol and 100 mg of 5% palladium on barium sulphate are added. The mixture is stirred under a hydrogen atmosphere for 3 hours. The catalyst is removed by filtration, the filtrate is concentrated to dryness and then taken up in ethyl acetate, water is added and the pH is adjusted to 5 by the addition of a solution of sodium hydrogen carbonate.

The organic phase is washed with a saturated solution of sodium chloride, dried over sodium sulphate and concentrated under vacuum. The residue obtained is taken up in ether, the precipitate formed is filtered, washed with ether and dried.

m=140 mg m.p.=138°–140° C.

mass spectrum: MH⁺: 433.

NMR: 7.10–7.50 ppm: m: 9 H: aromatic 4.75 ppm: s: 2 H: N—CH₂—C₆H₄, 4.45 ppm: t: 1 H: C$\underline{H}$—CH₂—CO₂H 2.40 ppm: t: 2 H: C$\underline{H_2}$—CH₂—C$\underline{H_2}$—CH₃, 2.05–1.70 ppm: H: cyclopentane 1.45 ppm: q: 2 H: CH₂—C$\underline{H_2}$—CH₂—CH₃ 1.15 ppm: sext: 2 H: CH₂—C$\underline{H_2}$—CH₂—CH₃ 0.80 ppm: t: 3 H: CH₂—CH₂—CH₂—C$\underline{H_3}$.

EXAMPLE 4

2-[4-((2-n-Butyl-5-oxo-4-spirocyclopentane-2-imidazolin-1-yl)methyl)phenyl]-2,2-diphenylacetic acid.

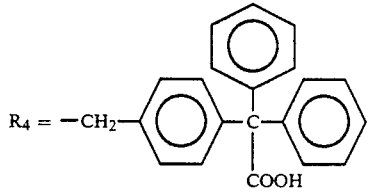

A) 2,2-Diphenyl-2-(para-tolyl)acetic acid.

This acid is prepared according to the method of A. Bistrzycki (Chem. Ber. 1901, 34, 3079–3080) by the action of toluene on benzilic acid.

B) tert-Butyl ester of 2,2-diphenyl-2-(para-tolyl)acetic acid 5 g of the preceding acid are placed in 30 ml of DCM and 30 ml of benzene and 2.31 g of oxalyl chloride are added at 0° C. and the mixture is then left stirring for 3 hours at RT. The reaction mixture is concentrated under vacuum and then evaporated twice with benzene, the residue is taken up in 50 ml of THF, 2.5 g of potassium tert-butoxide are added and the mixture is stirred for 1 hour at RT. The reaction mixture is diluted with 200 ml of ethyl acetate and 50 ml of water, the organic phase is separated, washed with a saturated solution of sodium chloride, dried over sodium sulphate and evaporated to dryness. The expected ester is obtained in the form of an oil and identified by its NMR spectrum.

C) tert-Butyl ester of 2-(para-bromomethyl)phenyl-2,2-diphenylacetic acid.

1 g of the ester obtained in the preceding stage is dissolved in 40 ml of carbon tetrachloride and 50 mg of benzoyl peroxide and 534 mg of NBS are added. After 3 and a half hours of heating at reflux under U.V. irradiation, the succinimide formed is filtered off and then the filtrate is concentrated under vacuum. 1.13 g of oil are obtained.

D) tert-Butyl ester of 2-[4-((2-n-butyl-5-oxo-4-spiro-cyclopentane-2-imidazolin-1-yl)methyl)phenyl]-2,2-diphenylacetic acid.

The hydrochloride of 2-n-butyl-4-spirocyclopentane-2-imidazolin-5-one obtained in Example 1, stage D is used.

578 mg of this compound are placed in 10 ml of DMF in the presence of 150 mg of 80% sodium hydride in oil. After 20 minutes, the brominated derivative obtained in the preceding stage (1.13 g), in 10 ml of DMF is added and the mixture is left stirring for 30 minutes. The reaction mixture is concentrated to half its volume and then diluted with 100 ml of ethyl acetate and 15 ml of water. The organic phase is separated off, washed with a saturated solution of sodium chloride, dried over sodium sulphate and then concentrated under vacuum. The residue is chromatographed on silica by eluting with an ethyl acetate/toluene mixture. 580 mg of the expected product, characterised by the NMR and IR spectra, are obtained in the form of a wax.

IR (CHCl$_3$): 1725-1715 cm$^{-1}$: C=O: imidazolinone and ester, 1630 cm$^{-1}$: C=N: imidazolinone E) 2-[4-((2-n-Butyl-5-oxo-4-spirocyclopentane-2-imidazolin-1-yl)methyl)phenyl]-2,2-diphenylacetic acid.

The product obtained in the preceding stage is treated for 45 minutes at RT with 3 ml of TFA in 3 ml of DCM. After evaporating to dryness, the residue is taken up in ether, the precipitate formed is filtered, washed with ether and dried. 500 mg of white powder are obtained.

m.p.=197° C.

NMR: 7.10-7.40 ppm: m: 14 H: aromatic, 4.85 ppm: s: 2 H: N—C$\underline{H}_2$—C$_6$H$_4$—, 2.70 ppm: t: 2 H: CH$_3$—CH$_2$—C$\underline{H}_2$—CH$_2$—, 1.80-2.10 ppm: m: 8 H: cyclopentane, 1.50 ppm: quint: 2 H: CH$_3$—CH$_2$—C$\underline{H}_2$—CH$_2$—, 1.30 ppm: sext: 2 H: CH$_3$—C$\underline{H}_2$—CH$_2$—CH$_2$—, 0.80 ppm: t: 3 H: CH$_3$(nBu).

EXAMPLE 5

1-[4-(Dibenzyl-(5-tetrazolyl)methyl)benzyl]-2-n-butyl-4-spirocyclopentane-2-imidazolin-5-one.

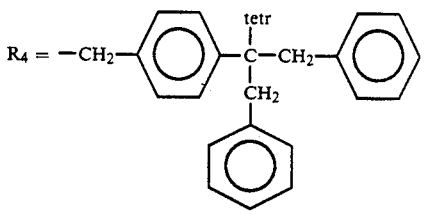

A) 1,3-Diphenyl-2-(para-tolyl)-2-cyanopropane.

3.93 g of para-methylbenzyl cyanide in 7 ml of DMSO and 4.8 g of sodium hydroxide in 5 ml of water are added simultaneously over 15 minutes to a solution of 10.7 ml of benzyl bromide in 25 ml of DMSO; the mixture is cooled in a water bath at 20° C. so that the temperature of the reaction mixture does not exceed 60° C. 1 hour and 45 minutes after the end of the addition, the reaction mixture is diluted with 150 ml of ether and 50 ml of water, the organic phase is separated off, washed with a saturated solution of sodium chloride, dried over sodium sulphate and concentrated under vacuum; the solid residue is taken up in ether, filtered and dried. 7 g of white solid are obtained.

m.p.=128°-129° C.

IR (CHCl$_3$): 2200 cm$^{-1}$: CN

B) 1,3-Diphenyl-2-(4-(bromomethyl)phenyl)-2-cyanopropane.

3.11 g of the product obtained in the preceding stage are dissolved in 150 ml of carbon tetrachloride, 1.78 g of NBS and 90 mg of benzoyl peroxide are added and the mixture is heated at reflux for 2 hours and 15 minutes. The succinimide formed is filtered and the filtrate is concentrated under vacuum. The expected brominated derivative is obtained in the form of a wax and identified by its NMR spectrum. The reaction is quantitative.

C) 1-[4(Diphenylcyamomethyl)benzyl]-2-n-butyl-4-spirocyclopentane-2-imidazolin-5-one.

920 mg of hydrochloride of 2-n-butyl-4-spirocyclopentane-2-imidazolin-5-one are dissolved in 15 ml of DMF, 300 mg of 80% sodium hydride in oil are added and, after 10 minutes, 1.86 g of the brominated derivative prepared in the preceding stage, dissolved in 10 ml of DMF, are added. After 2 and a half hours of stirring, the reaction mixture is diluted with 150 ml of ethyl acetate and 20 ml of water. The organic phase is separated off, washed with a saturated solution of sodium chloride, dried over sodium sulphate and concentrated under vacuum. The residue is chromatographed on silica by eluting with an ethyl acetate/toluene mixture. 180 g of the expected product are obtained in the form of a foam.

IR (CHCl$_3$):
1625 cm$^{-1}$: C=N imidazolinone,
2200 cm$^{-1}$: CN weak.

D) 1-[4(Dibenzyl(5-tetrazolyl)methyl)benzyl]-2-n-butyl-4-spirocyclopentane-2-imidazolin-5-one.

Tribuytyltin azide is prepared according to the method described by Kricheldorf and Leppert in Synthesis, 1976, 329.

1.8 g of the compound prepared in stage C and 1.1 equivalent of tributylin azide are heated at reflux for 95 hours in 20 ml of xylene. After cooling, the reaction mixture is diluted with 30 ml of xylene and then extracted 3 minutes with 20 ml of 1N sodium hydroxide. The 3 aqueous phases are combined and then extracted twice with 20 ml of ether. 200 ml of DCM are added to the aqueous phase which is then adjusted to pH 5.0 by the addition of 3N hydrochloric acid. The organic phase is separated off, washed once with water, once with a saturated solution of sodium chloride, dried over sodium sulphate and then evaporated to dryness. The residue is taken up in ether and the solid obtained is filtered and dried.

m=700 mg m.p.=157°-159° C.

NMR: 7.6-7.10 ppm: m: 14 H: aromatic 4.60 ppm: s: 2 H: N—C$\underline{H}_2$—C$_6$H$_4$ 3.35-3.65 ppm: 4 s: 4 H: 2C$\underline{H}_2$ (benzyl) 2.25 ppm: t: 2 H: CH$_3$—CH$_2$—CH$_2$—C$\underline{H}_2$ 1.95 ppm: m: 8 H: cyclopentane 1.50 ppm: quint: 2 H: CH$_3$CH$_2$—C$\underline{H}_2$—CH$_2$ 1.25 ppm: sext: 2 H: CH$_3$—C$\underline{H}_2$—CH$_2$—CH$_2$— 0.80 ppm: t: 3 H: CH$_3$(n-Bu).

EXAMPLE 6

(E)-3-[4-((2-n-Butyl-5-oxo-4-spirocyclopentane-2-imidazolin-1-yl)methyl)phenyl]-2-phenylacrylic acid.

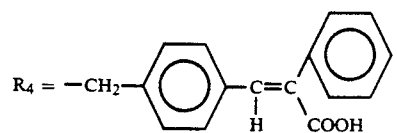

A)  4-[(2-n-Butyl-5-oxo-4-spirocyclopentane-2-imidazolin-1-yl)methyl]benzonitrile.

1.14 g of 80% sodium hydride in oil are suspended in 15 ml of anhydrous DMF under argon and 4 g of 2-n-butyl-4-spirocyclopentane-2-imidazolin-5-one in 15 ml of anhydrous DMF are added dropwise, under argon, at 0° C. After stirring for 20 minutes at RT under argon, 3.74 g of 4-(bromomethyl)benzonitrile are added. After 20 minutes, the DMF is concentrated under vacuum and the mixture is then taken up with 150 ml of ethyl acetate and is washed successively with 100 ml of water, 100 ml of 5% aqueous solution of $KHSO_4$—$K_2SO_4$, 50 ml of a saturated solution of sodium chloride, 100 ml of a saturated solution of sodium hydrogen carbonate, and again with 50 ml of a saturated solution of sodium chloride. The mixture is dried over sodium sulphate, filtered and the filtrate is concentrated. 5.64 g of the expected product are obtained in the form of an oil.

NMR: 0.80 ppm: t: 3 H: $CH_3(nBu)$, 1.25 ppm: sext: 2 H: $CH_3$—$\underline{CH_2}$—, 1.50 ppm: m: 2 H: $CH_3$—$\underline{CH_2}$—$CH_2$—, 1.75–2.0 ppm: m: 8 H: cyclopentane, 2.35 ppm: t: 2 H: $CH_3$—$CH_2$—$CH_2$—$\underline{CH_2}$—, 4.8 ppm: s: 2 H: $\underline{CH_2}$—$C_6H_4$—, 7.6 ppm: q: 4 H: aromatic B)  4-[(2-n-Butyl-5-oxo-4-spirocyclopentane-1-imidazolinyl)methyl]benzaldehyde.

4.5 g of Raney nickel, 4.5 g of the compound obtained in the preceding stage and 70 ml of 75% strength aqueous formic acid are placed in a flask and the mixture is heated at reflux for 1 hour. The nickel is filtered on Celite and the filtrate is diluted with 100 ml of water and is extracted 3 times with 50 ml of ethyl acetate. The organic phases are combined and are washed 3 times with 100 ml of a saturated solution of sodium hydrogen carbonate, then with 100 ml of a saturated solution of sodium chloride, then the mixture is dried over sodium sulphate, is filtered and the filtrate is concentrated. The oil obtained is purified by chromatography on silica by eluting with a hexane/ethyl acetate (6/4; v/v) mixture. 1.93 g of the expected compound are obtained in the form of an oil.

NMR: 0.89 ppm: t: 3 H: $CH_3(nBu)$, 1.15 ppm: sext: 2 H: $CH_3$—$\underline{CH_2}$—, 1.40 ppm: m: 2 H: $CH_3$—$\underline{CH_2}$—$CH_2$—, 1.5–1.8 ppm: m: 8 H: cyclopentane, 2.20 ppm: t: 2 H: $CH_3$—$CH_2$—$CH_2$—$\underline{CH_2}$—, 4.8 ppm: s: 2 H: $\underline{CH_2}$—$C_6H_4$—, 7.6 ppm: q: 4 H: aromatic. 9.85 ppm: s: 1 H: CHO.

C) (E)-3-[4((2-n-Butyl-5-oxo-4-spirocyclopentane-2-imidazolin-1-yl)methyl)phenyl]-2-phenylacrylic acid.

This stage is carried out according to H. E. Zimmerman et al., J. Am. Chem. Soc., 1959, 2086.

A solution containing 1.93 g of the aldehyde prepared in the preceding stage, 850 mg of phenylacetic acid, 6 ml of acetic anhydride and 6 ml of triethylamine are brought to reflux for 35 minutes. The reaction mixture is cooled in an ice bath and then 10 ml of concentrated hydrochloric acid and then 100 ml of water are slowly added at 0° C. The aqueous phase is extracted with 3 times 50 ml of DCM, the organic phases are combined, washed with 100 ml of water, dried over sodium sulphate, filtered and the filtrate is concentrated. The gum obtained is taken up with 100 ml of ethyl ether and is extracted 3 times with 50 ml of 10% sodium hydroxide. The alkaline phase is acidified to pH 3-4 by the addition of concentrated hydrochloric acid and is then extracted 3 times with 50 ml of ethyl acetate. The extract is dried over sodium sulphate, filtered and concentrated. The product obtained is purified by chromatography on silica by eluting with AcOEt/toluene/AcOH (2/8/0.3;

v/v/v). An oil (m=850 mg) is obtained which precipitates on trituration in ether.

m.p.=153° C.

NMR: 0.75 ppm: t: 3 H: $CH_3(nBu)$, 1.20 ppm: sext: 2 H: $CH_3$—$\underline{CH_2}$—, 1.40 ppm: m: 2 H: $CH_3$—$\underline{CH_2}$—$CH_2$—, 1.50–1.90 ppm: m: 8 H: cyclopentane, 2.2 ppm: t: 2 H: $CH_3$—$CH_2$—$CH_2$—$\underline{CH_2}$—, 4.60 ppm: s: 2 H: $\underline{CH_2}$—$C_6H_4$, 6.90–7.70 ppm: m: 10 H: aromatic and 1 H ethylenic

EXAMPLE 7

(Z)-3-[4-((2-n-Butyl-5-oxo-4-spirocyclopentane-2-imidazolin-1-yl)methyl)phenyl]-2-phenylacrylic acid.

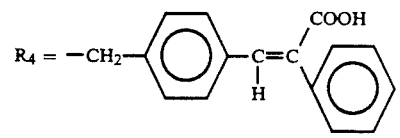

A) (Z)-2-Phenyl-3-(para-tolyl)acrylic acid.

A mixture containing 25 g of phenylacetic acid, 35 ml of 4-methylbenzaldehyde, 20 ml of acetic anhydride and 20 ml of triethylamine is brought to reflux at 110° C. for 22 hours. It is cooled in an ice bath, is acidified with 40 ml of concentrated hydrochloric acid and is then diluted by the addition of water. It is extracted 3 times with 300 ml of ethyl ether, the ether phases are combined, are washed with 400 ml of water and are then extracted with a liter of 2% sodium hydroxide solution (pH 14). The alkaline phase is acidified with acetic acid to pH 7 and the precipitate, which is the (E) acid, is filtered. The filtrate is adjusted to pH 4, is extracted with 3 times 300 ml of DCM and is concentrated to dryness. The oil obtained precipitates on the addition of an ether/hexane (1/5; v/v) mixture. The expected compound (Z acid) is obtained pure by recrystallisation from toluene while warm and addition of hexane while cold.

m.p.=86° C.

m=4.3 g

NMR: 2.3 ppm: s: 3 H: $CH_3$ 7.0–7.6 ppm: m: 10 H: aromatic+H ethylenic 13.3 ppm: s: 1 H: $CO_2H$.

B) tert-Butyl ester of (Z)-2-phenyl-3-(para-tolyl)acrylic acid.

2 g of the compound obtained in the preceding stage are dissolved in 40 ml of DCM, 800 μl of oxalyl chloride are added under nitrogen and the mixture is stirred under nitrogen, at RT, for 5 hours. After evaporation to dryness, the mixture is evaporated again twice after addition of 40 ml of toluene. The residue is dissolved in 40 ml of anhydrous THF and 1.04 g of potassium tert-butoxide are added to it while cold under nitrogen. After stirring for 1 hour at RT under nitrogen, the mixture is diluted with 50 ml of water and then with 50 ml of ether, it is separated and the aqueous phase is extracted twice with 30 ml of ether. The ether phases are combined and washed with a 2% sodium hydroxide solution and then with a saturated solution of sodium chloride. They are dried over sodium sulphate, filtered and the filtrate is concentrated. The oil obtained is purified by chromatography on silica by eluting with a DCM/hexane (1/1; v/v) mixture. 780 mg of the expected product are obtained in the form of an oil.

NMR: 1.2 ppm: s: 9 H: (tBu), 2.2 ppm: s: 3 H: $CH_3$, 6.9–7.4 ppm: m: 10 H: H aromatic+H ethylenic C) tert-Butyl ester of (Z)-3-(para-bromomethyl)phenyl-2-phenylacrylic acid 780 mg of the compound prepared in the preceding stage, 470 mg of NBS and 10 mg of benzoyl peroxide are suspended in 50 ml of carbon tetrachloride and are left stirring, under a U.V. radiation for 2 hours while holding at gentle reflux by heating. The reaction mixture is cooled in an ice bath and then the succinimide formed is filtered off. By concentration of the filtrate, 1.22 g of an oil which is used as it is in the following stage, are obtained.

D) tert-Butyl ester of (Z)-3-[4-((2-n-butyl-5-oxo-4-spirocyclopentane-2-imidazolin-1-yl)methyl)phenyl]-2-phenylacrylic acid.

165 mg of 80% sodium hydride in oil are suspended under argon in 20 ml of anhydrous DMF and 780 mg of 2-n-butyl-4-spirocyclopentane-2-imidazolin-5-one are added, in small portions, at 0° C. After stirring for 20 minutes under argon, 1.22 g of the brominated derivative prepared in the preceding stage are added and the mixture is left stirring for 5 hours, at RT, under argon. After concentration of the reaction mixture under vacuum, it is taken up with 100 ml of ethyl acetate and is washed with 50 ml of water, 30 ml of a 5% solution of $KHSO_4$—$K_2SO_4$, 30 ml of a saturated solution of sodium chloride, 30 ml of sodium hydrogen carbonate and then 30 ml of a saturated solution of sodium chloride. The organic phase is dried over sodium sulphate, is filtered and the filtrate is concentrated. The oil obtained is purified by chromatography on silica by eluting with a DCM-acetone (100/4; v/v) mixture. 890 mg of the expected compound are obtained pure.

2-imidazolin-1-yl)methyl)phenyl]-2-phenylacrylic acid.

890 mg of the compound obtained in the preceding stage are dissolved in 10 ml of DCM and 5 ml of TFA and the mixture is left stirring for 2 hours at RT. After concentration to dryness of the reaction mixture, the oil obtained is triturated in ether and then the ether is evaporated; on repeating this operation, a white precipitate is formed, it is filtered and then dried in a desiccator. 350 mg of the expected compound are obtained.

m.p.=158°-161° C.

NMR: 0.8 ppm: t: 3 H: $CH_3(nBu)$, 1.25 ppm: sext: 2 H: $CH_3$—$CH_2$—, 1.50 ppm: m: 11 H: tBu and $CH_3$—$CH_2$—$CH_2$—, 1.8-2.0 ppm: m: 8 H: cyclopentane, 2.3 ppm: t: 2 H: $CH_3$—$CH_2$—$CH_2$—$CH_2$—, 4.8 ppm: s: 2 H: $CH_2$—$C_6H_4$, 6.9-7.7 ppm: m: 10 H: aromatic and H ethylenic

EXAMPLE 8

N-Phenyl-N-[4-((2-n-butyl-4-spirocyclopentane-5-oxo-2-imidazolin-1-yl)methyl)phenyl]aminoacetic acid.

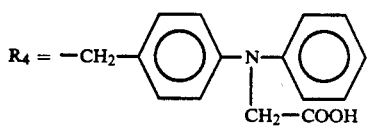

A) N-(para-Tolyl)aniline is prepared according to the operating procedure described by C. Izard-Verchere et al., in Chim. Therap., 1971, (5), 346-351.

B) N-Phenyl-N-(para-tolyl)trifluoroacetamide.

3.66 g of the amine prepared in stage A are dissolved in 50 ml of DCM, 3.04 ml of triethylamine are added at 0° C., and then, over 2 minutes, 2.96 ml of trifluoroacetic anhydride. After stirring for 1 hour at RT, the reaction mixture is diluted with 200 ml of ether and 200 ml of water. The organic phase is separated and then washed successively with a halfsaturated solution of sodium bicarbonate at 0° C., a 5% solution of potassium sulphate-bisulphate, and a saturated solution of sodium chloride. After drying over sodium sulphate, the organic phase is evaporated under vacuum and 5.4 g of the expected product are obtained in the form of an oil; the product is identified by its NMR and IR spectra.

C) N-(para-Bromomethyl)phenyl-N-phenyltrifluoroacetamide.

2.8 g of the product obtained in stage C are diluted in 120 ml of carbon tetrachloride and 100 mg of azobisisobutyronitrile, 100 mg of benzoyl peroxide and 1.96 g of NBS are added. After 2 and a half hours of heating at reflux, the reaction mixture is cooled and filtered. The filtrate is concentrated under vacuum and an oil is obtained; the expected product is identified by its NMR spectrum.

D) N-[4-((2-n-Butyl-4-spirocyclopentane-5-oxo-2-imidazolin-1-yl)methyl)phenyl]-N-phenyltrifluoroacetamide.

300 mg of 80% sodium hydride in oil are added, over 10 minutes, to 1.15 g of the hydrochloride of 2-n-butyl-4-spirocyclopentane-2-imidazolin-5-one in 14 ml of DMF and then, after 15 minutes, the product prepared in stage C, dissolved in 5 ml of DMF, is added over 15 minutes. After stirring for 3 hours at RT, the reaction mixture is diluted in 100 ml of ethyl acetate and 20 ml of water; the organic phase is separated off, washed with water and then with a saturated solution of sodium chloride, dried over sodium sulphate and then concentrated under vacuum. The residue is chromatographed on silica by eluting with an AcOEt/toluene (2/3; v/v) mixture. 1.5 g of the expected product are obtained in the form of wax; the product is identified by its IR and NMR spectra.

E) 1-(4-phenylaminobenzyl)-2-n-butyl-4-spirocyclopentane-2-imidazolin-5-one.

The product obtained in the preceding stage is diluted in 15 ml of methanol and 3.5 ml of 2N sodium hydroxide are added. After stirring for 50 minutes, the reaction mixture is diluted with 100 ml of ethyl acetate and 20 ml of water; the organic phase is separated off, washed with a saturated solution of sodium chloride and then concentrated under vacuum. 1.15 g of the expected product are obtained in the form of a wax. The product is identified by its IR and NMR spectra.

F) tert-Butyl ester of N-phenyl-N-[4-((2-n-butyl-4-spirocyclopentane-5-oxo-2-imidazolin-1-yl)methyl)phenyl]aminoacetic acid.

1.12 g of the product obtained in the preceding stage are dissolved in 10 ml of DMF and 100 mg of 80% sodium hydride in oil are added and then, after 15 minutes, 643 mg of tert-butyl bromoacetate diluted in 1 ml of DMF are added. The same quantities of ethyl bromoacetate and sodium hydride are added again, 3 times, after 2 hours, 6 hours and 22 hours. After 28 hours, the reaction mixture is diluted with 100 ml of ethyl acetate and 20 ml of water; the organic phase is separated off and then washed with a saturated solution of sodium chloride, dried over sodium sulphate and concentrated under vacuum. The residue is chromatographed on silica by eluting with a chloroform/hexane (4/6; v/v) mixture containing 4% of methanol. The expected product is identified by its IR and NMR spectra.

NMR: 4.70 ppm: s: 2 H: N-C$\underline{H_2}$—C$_6$H$_4$ 4.45 ppm: s: 2 H: N-CH$_2$—CO$_2$tBu.

G) N-Phenyl-N-[4-((2-n-butyl-4-spirocyclopentane-5-oxo-2-imidazolin-1-yl)methyl)phenyl]aminoacetic acid.

The product obtained in the preceding stage is treated for 10 minutes with a mixture of 15 ml of DCM and 20 ml of TFA. After concentrating under vacuum, the residue is taken up in 40 ml of water and 20 ml of ether and adjusted to pH 10 by the addition of 2N sodium hydroxide. The aqueous phase is separated and adjusted to pH 5 by the addition of 2N hydrochloric acid, in the presence of ethyl acetate. The organic phase is washed with a saturated solution of sodium chloride, dried over sodium sulphate and then concentrated under vacuum. The residue is chromatographed on silica by eluting with an AcOEt/toluene (2/1; v/v) mixture containing 0.3 % of acetic acid. 400 mg of the expected product are obtained.

m.p. = 140°–142° C.

mass spectrum: MH+ = 434

NMR: 6.00–7.35 ppm: m: 9 H: aromatic, 4.65 ppm: s: 2 H: N-C$\underline{H_2}$—C$_6$H$_4$—, 4.45 ppm: s: 2 H: N-CH$_2$—CO$_2$H, 2.35 ppm: t: 2 H: CH$_3$—CH$_2$—C$\underline{H_2}$—CH$_2$, 1.60–2.00 ppm: m: 8 H: cyclopentane, 1.50 ppm: quint: 2 H: CH$_3$—CH$_2$—C$\underline{H_2}$—CH$_2$—, 1.30 ppm: sext: 2 H: CH$_3$—C$\underline{H_2}$—CH$_2$—CH$_2$—,

EXAMPLE 9

2,2-Dichloro-2-[4-((2-n-butyl-5-oxo-4-spirocyclopentane-2-imidazolin-1-yl)methyl)phenyl]acetic acid.

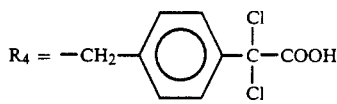

A) Ethyl (para-tolyl)dichloroacetate is prepared according to the procedure described by R. N. McDonald and R. C. Cousins in J. Org. Chem., 1980, 45, 2976-2984.

B) Ethyl (para-bromomethyl)dichloroacetate is obtained by the action of benzoyl peroxide and NBS on the compound prepared in stage A, according to the procedure described in the preceding examples.

C) The ethyl ester of 2,2-dichloro-2-[4-((2-n-butyl-5-oxo-4-spirocyclopentane-2-imidazolin-1-yl)methyl)phenyl]acetic acid is prepared by the action of the brominated derivative obtained in the preceding stage on the hydrochloride of 2-n-butyl-4-spirocyclopentane-2-imidazolin-5-one, according to the procedure described in the preceding examples. The compound obtained is characterised by its IR and NMR spectra.

IR (CHCl$_3$): 1710-1715 cm$^{-1}$: C=O: ester and imidazolinone, 1630 cm$^{-1}$: C=N: imidazolinone.

D) 2,2-Dichloro-2-[4-((2-n-butyl-5-oxo-4-spirocyclopentane-2-imidazolin-1-yl)methyl)phenyl]acetic acid.

0.95 g of the ester obtained in stage C are dissolved in 4 ml of methanol and 4 ml of dioxane. 1.1 ml of 2N sodium hydroxide are added and the mixture is left stirring for 40 minutes at RT. The reaction mixture is diluted with 60 ml of AcOEt and 10 ml of water and 1N hydrochloric acid is added to bring it to a pH of 4.8. The precipitate formed is filtered, washed with water and then with ether and dried under vacuum. 290 mg of the expected product are obtained.

m.p. = 185°–187° C.

Another portion of the expected product is obtained from the neutralisation medium: the latter is separated off, the organic phase is washed with water and then with a saturated solution of sodium chloride, dried over sodium sulphate and concentrated under vacuum. 290 mg of the expected product are obtained.

m.p. = 178°–180° C.

The IR and NMR spectra are identical for the products obtained.

NMR: 7.60–7.15 ppm: AA'BB' system: 4H: aromatic, 4.65 ppm: s: 2 H: N—C$\underline{H_2}$—C$_6$H$_4$—, 2.30 ppm: t: 2 H: CH$_3$—CH$_2$—CH$_2$—C$\underline{H_2}$, 1.50–1.90 ppm: m: 8 H: cyclopentane, 1.40 ppm: quint: 2 H: CH$_3$—CH$_2$—C$\underline{H_2}$—CH$_2$, 1.15 ppm: sext: 2 H: CH$_3$—C$\underline{H_2}$—CH$_2$—CH$_2$, 0.70 ppm: t: 3 H: C$\underline{H_3}$—CH$_2$—CH$_2$—CH$_2$.

EXAMPLE 10

2-n-Butyl-4-spirocyclopentane-1-[4-(2-(5-tetrazolyl)isopropyl)benzyl]-2-imidazolin-5-one.

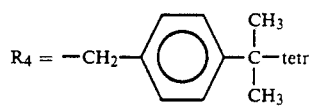

A) 2-(para-tolyl)-2-cyanopropane.

This compound is prepared according to J. Org. Chem. 1969, 34, 227.

Bromomethane is sparged into 50 ml of DMSO for 15 minutes and 6.56 g of 4-methylbenzyl cyanide and 16 g of 50% sodium hydroxide in water are added dropwise. The inflow of gas is maintained for 1 hour, then 125 ml of water are added and the mixture is extracted with ether, washed with a solution of sodium carbonate and then with a saturated solution of sodium chloride, dried and then evaporated under vacuum. The liquid obtained distils at 130° C. 5 g of the expected product are collected.

B) 2-(5-tetrazolyl)-2-(para-tolyl)-propane.

2.1 g of the compound prepared in the preceding stage and 2.1 g of tributyltin azide are brought to reflux for 96 hours in 20 ml of xylene. After evaporating the solvents, the mixture is taken up with water, extracted twice with AcOEt, the organic phase is washed with water and then the organic phase is extracted twice with 2N sodium hydroxide. The basic aqueous phase is washed with ether, cooled and then acidified by the addition of 5N hydrochloric acid to pH 3–4. By extracting with AcOEt, 1.57 g of the expected product which is characterised by its NMR spectrum, are obtained.

C) 2-[(1-trityl)-5-tetrazolyl]-2-(para-tolyl)-propane.

1.5 g of the compound obtained in the preceding stage, 2.29 g of trityl chloride and 1.3 ml of triethylamine are brought to reflux for 5 hours in DCM. After evaporating the solvents, the mixture is taken up with AcOEt and washed successively with a 3% potassium hydrogen sulphate solution, with 1N sodium hydroxide, water and a saturated solution of sodium chloride. The product obtained is chromatographed on an alumina column by eluting with a hexane/DCM (70/30; v/v) mixture. 1.92 g of the expected product characterised by its IR and NMR spectra, are obtained.

D) 2-[(1-trityl)-5-tetrazolyl]-2-[para-(bromomethyl)phenyl]-propane.

A mixture containing 1.92 g of the compound prepared in the preceding stage, 846 mg of NBS and 100 mg of benzoyl peroxide is brought to reflux for 3 hours in 30 ml of carbon tetrachloride. When the reaction mixture has returned to RT, the succinimide formed is filtered off, the tetrachloride evaporated, and the mixture is taken up with ether, washed with water and then with a saturated solution of sodium chloride. 2.06 g of the expected compound are obtained.

E) 2-n-Butyl-4-spirocyclopentane-1-[4-(2-((1-trityl)-5-tetrazolyl)-isopropyl)benzyl]-2-imidazolin-5-one.

10 ml of DMF containing 50 mg of 80% sodium hydride in oil are placed under nitrogen. 194 mg of 2-n-butyl-4-spirocyclopentane-2-imidazolin-5-one in 10 ml of DMF and then, after 30 minutes at RT, 748 mg of the brominated derivative prepared in stage D in 10 ml of DMF are added dropwise. After stirring for 2 and a half hours at RT, the mixture is evaporated, taken up with AcOEt and water, separated and then dried over sodium sulphate. The product obtained is chromatographed on alumina by eluting with a hexane/AcOEt (90/10; v/v) mixture. 390 mg of the expected product are obtained. F) 2-n-Butyl-4-spirocyclopentane-1-[4-(2-(5-tetrazolyl)-isopropyl)benzyl]-2-imidazolin-5-one.

380 mg of the compound obtained in the preceding stage is left stirring for 4 hours in 4 ml of methanol and 0.3 ml of 4N hydrochloric acid and the mixture is then heated at 30° C. for 18 hours. After evaporating, the mixture is taken up with water, alkalified with sodium hydroxide, washed with ether, with toluene and again with ether and then the aqueous phase is acidified to pH 5 by the addition of 1N hydrochloric acid and is extracted with ethyl acetate. 150 mg of the expected product are obtained.

m.p.=95° C.

NMR: 0.85 ppm: t: 3 H: $CH_3$(tBu), 1.2 ppm: sext: 2 H: $CH_3$—$CH_2$—, 1.55 ppm: quint: 2 H: $CH_3$—$CH_2$—$CH_2$—, 1.65-2.1 ppm: m: 14 H: cyclopentane°2$CH_3$ (dimethyl), 2.45 ppm: t: 2 H: $CH_3$—$CH_2$—$CH_2CH_2$—, 4.75 ppm: s: 2 H: N—$CH_2$—$C_6H_4$—, 7.25 ppm: m: 4 H: aromatic

EXAMPLE 11

2-n-Butyl-4-spirocyclopentane-1-[3-(2-(5-tetrazolyl)isopropyl)benzyl]-2-imidazolin-5-one.

$$R_4 = -CH_2-\underset{\underset{CH_3}{|}}{\overset{\overset{CH_3}{|}}{\bigcirc}}-C-tetr$$

This compound is prepared according to the procedure described in the preceding example by using meta-methylbenzyl cyanide as the starting product.

m.p.=55° C.

NMR: 0.7 ppm: t: 3 H: $CH_3$(nBu), 1.2 ppm: sext: 2 H: $CH_3$—$CH_2$—, 1.35 ppm: quint: 2 H: $CH_3$—$CH_2$—$CH_2$—, 1.5-2 ppm: m: 14 H: cyclopentane+2$CH_3$ (dimethyl), 2.2 ppm: t: 2 H: $CH_3$—$CH_2$—$CH_2$—$CH_2$—, 4.6 ppm: s: 2 H: N—$CH_2$—$C_6H_4$—, 6.7-7.4 ppm: m: 4 H: aromatic

EXAMPLE 12

2-n-Butyl-4-spirocyclopentane-1-[4-(1-(5-tetrazolyl)-1-propylbutyl)benzyl]-2-imidazolin-5-one.

$$R_4 = -CH_2-\bigcirc-\underset{CH_3(CH_2)_2}{\overset{}{C}}\diagdown_{(CH_2)_2CH_3}^{tetr}$$

This compound is prepared according to the procedure described in Example 10. It is characterised by its melting point.

m.p.=50° C.

In the first stage, 1,1-dipropyl-para-methylbenzyl cyanide is obtained by the action of bromopropane on para-methylbenzyl cyanide.

NMR: 0.5-2.5 ppm: m: 31 H: (nBu) cyclopentane $2C_3H_7$ (dipropyl), 4.75 ppm: s: 2 H: N—$CH_2$—$C_6H_4$—, 7.2 ppm: m: 4 H: aromatic

EXAMPLE 13

2-n-Butyl-4-spirocyclopentane-1-[4-(5-tetrazolyl)benzyl]-2-imidazolin-5-one.

A) para-(5-tetrazolyl)-toluene.

$$R_4 = -CH_2-\bigcirc-tetr$$

A mixture containing 2.34 g of para-tolyl cyanide, 1.45 g of sodium azide and 1.28 g of ammonium chloride is heated to 120° C. in DMF. The solvent is evaporated, the mixture is taken up with water, extracted twice with AcOEt, the organic phase is washed with water, the organic phase is extracted twice with 2N sodium hydroxide and then the alkaline phase is washed with ether. The alkaline phase is cooled in a water-ice mixture and is then acidified to pH 3 by the addition of 5N hydrochloric acid. It is filtered, washed with water and dried under vacuum in the presence of potassium hydroxide. 2.5 g of the expected product characterised by its NMR spectrum, are obtained.

B) para-[(1-trityl)-5-tetrazolyl]-toluene.

2.5 g of the compound obtained in the preceding stage, 5.22 g of trityl chloride and 3.2 ml of triethylamine are brought to reflux for 16 hours in DCM. The solvent is evaporated off, the mixture is taken up with AcOEt, washed with a 3% solution of potassium hydrogen sulphate, with 1N sodium hydroxide, water and then with a saturated solution of sodium chloride. The product obtained is chromatographed on alumina by eluting with a hexane/DCM (80/20; v/v) mixture. 2.58 g of the expected product are obtained.

C) para-[(1-trityl)-5-tetrazolyl]-bromotoluene.

2.58 g of compound are obtained by treatment of 2.5 g of the compound obtained in the preceding stage with NBS and benzoyl peroxide according to the usual method.

D) 2-n-Butyl-4-spirocyclopentane-1-[4-(1-trityl-5-tetrazolyl)benzyl]-2-imidazolin-5-one.

475 mg of this compound are prepared by the usual method by treating 775 mg of the brominated compound obtained in the preceding stage with 194 mg of 2-n-butyl-4-spirocyclopentane-2-imidazolin-5-one.

E) 2-n-Butyl-4-spirocyclopentane-1-[4-(5-tetrazolyl)-benzyl]-2-imidazolin-5-one.

The expected compound is prepared from that obtained in the preceding stage by proceeding as in Example 10 stage F.

m.p.=90° C.

NMR: 0.7 ppm: t: 3 H: CH$_3$(nBu), 1.25 ppm: sext: 2 H: CH$_3$—CH$_2$—, 1.45 ppm: quint: 2 H: CH$_3$—CH$_2$—CH$_2$—, 1.55–2.0 ppm: m: 8 H: cyclopentane, 2.3 ppm: t: 2 H: CH$_3$—CH$_2$—CH$_2$—CH$_2$—, 4.7 ppm: s: 2 H: N—CH$_2$—C$_6$H$_4$—, 7.2–8.1 ppm: m: 4 H: aromatic

EXAMPLE 14

[5-(4-(2-n-Butyl-5-oxo-4-spirocyclopentane-2-imidazolin-1-yl)methylphenyl)-2-tetrazolyl]acetic acid.

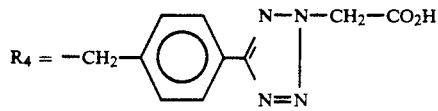

250 mg of 80% sodium hydride in oil and 10 ml of DMF are left stirring at RT, under a nitrogen atmosphere, and 1.49 g of the compound prepared in the preceding example (Example 13) dissolved in 20 ml of DMF are added dropwise and the mixture is left sirring for 30 minutes at RT. 925 mg of tert-butyl bromoacetate in 10 ml of DMF are then added. After stirring for hour at RT, the DMF is evaporated off, the residue is taken up in an AcOEt-water mixture and is extracted with AcOEt. The aqueous phase is acidified to pH 5 by the addition of 1N hydrochloric acid and is then extracted with AcOEt. The extract is dried over sodium sulphate, filtered and evaporated. The residue is chromatographed on silica by eluting with a DCM/MeOH/AcOH (95/5/1; v/v/v) mixture. 650 mg of the expected product are obtained.

m.p.=196°–198° C.

NMR: 0.65 ppm: t: 3 H: CH$_3$, 1.15 ppm: sext: 2 H: —CH$_2$—CH$_3$, 1.35 ppm: quint: 2 H: —CH$_2$—CH$_2$—CH$_3$, 1.5–1.95 ppm: m: 8 H: cyclopentane, 2.25 ppm: t: 2 H: CH$_3$—CH$_2$—CH$_2$—CH$_2$, 4.65 ppm: s: 2 H: N—CH$_2$—C$_6$H$_4$—, 5.65 ppm: s: 2 H: —N—CH$_2$—COOH, 7.1–8.1 ppm: m: 4 H: aromatic

EXAMPLE 15

2-n-Butyl-4-spirocyclopentane-1-[4-((5-tetrazolyl)-methyl)benzyl]-2-imidazolin-5-one.

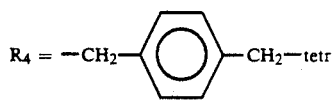

This compound is prepared according to the procedure described in Example 10. It is characterised by its melting point.

m.p.=120°–121° C.

NMR: 0.9 ppm: t: 3 H: CH$_3$(tBu), 1.4 ppm: sext: 2 H: CH$_3$—CH$_2$—, 1.6 ppm: m: 2 H: CH$_3$—CH$_2$—CH$_2$—, 1.8–2.3 ppm: m: 8 H: cyclopentane, 2.9 ppm: t: 2 H: —CH$_2$—CH$_2$—CH$_2$—CH$_3$, 4.35 ppm: s: 2 H: —CH$_2$—C$_6$H$_4$—, 5 ppm: s: 2 H: —N—CH$_2$—C$_6$H$_4$—, 7.35 ppm: m: 4 H: aromatic

EXAMPLE 16

2-n-Butyl-4-spirocyclopentane-1-[4-(1-(5-tetrazolyl)cyclohexyl)benzyl]-2-imidazolin-5-one.

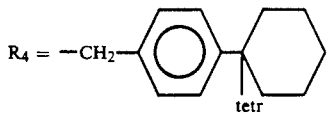

A) 1-Cyano-1-(para-tolyl)cyclohexane.

This compound is prepared according to the operating procedure described in J. Org. Chem. 1971, 36 (9), 1308.

2.7 g of 80% sodium hydride in oil are placed, under argon, in 40 ml of DMSO and a mixture of 5.24 g of para-methylbenzyl cyanide and 10.12 g of 1,5-dibromopentane in 20 ml of ether is added dropwise while maintaining the temperature between 25° and 35° C. using a bath of cold water. After the end of the exothermic reaction, the mixture is left stirring for 1 hour at 25° C. and is then cooled in an ice bath. 3 ml of isopropyl alcohol and 30 ml of water are added. After separation, extraction is carried out with ether and AcOEt. The organic phases are combined and washed 3 times with water and then with a saturated solution of sodium chloride, they are then dried over sodium sulphate and evaporated.

The product is then distilled under reduced pressure (0.2 mm Hg): BP=98°–102° C. 4.2 g of the pure product are obtained.

B) 2-n-Butyl-4-spirocyclopentane-1-[4-(1-(5-tetrazolyl)cyclohexyl)benzyl]-2-imidazolin-5-one.

In order to prepare the expected product, the various stages described in Example 10 are then followed according to the usual procedure.

m.p.=80°–100° C.

NMR: 0.6 ppm: t: 3 H: CH$_3$(nBu), 0.9–2.6 ppm: m: 24 H: cyclopentane+3CH$_2$(nBu)+cyclohexyl, 4.5 ppm: s/ 2 H: N—CH$_2$—C$_6$H$_4$—, 6.8–7.2 ppm: m: 4 H; aromatic, 15 ppm: b.s.: 1 H: NH (tetrazolyl),

EXAMPLE 17

2-[4-(2-n-Butyl-4-spirocyclopentane-5-oxo-2-imidazol-1-yl)methylphenyl]-2-methylpropionic acid.

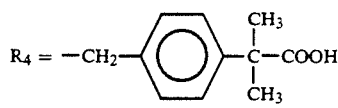

A) 2-(para-tolyl)-2-cyanopropane.

The preparation of this compound is similar to that described in Example 10.

B) 2-(para-Tolyl)-2-methylpropionic acid.

24.4 g of the compound prepared in the preceding stage in 1.44 l of diethyl ethylene glycol and 1.88 l of 40% aqueous potassium hydroxide are brought to reflux for 16 hours. The reaction mixture is diluted with water and then extracted with ether. The aqueous phase is acidified with concentrated hydrochloric acid, extracted with ethyl acetate, washed with water, dried over sodium sulphate and concentrated. The product obtained is chromatographed on silica by eluting with an AcOEt/hexane/acetic acid (20/80/1; v/v/v) mixture. 22 g of the expected product are collected.

C) Methyl ester of 2-(para-tolyl)-2-methylpropionic acid.

4.3 g of the acid prepared in the preceding stage and 10 ml of thionyl chloride are brought to reflux for 2 hours. The excess thionyl chloride is evaporated, the residue is taken up several times with toluene and the toluene is then evaporated off. 20 ml of methanol and then 1.9 ml of pyridine are added dropwise at RT and the mixture is brought to reflux for 1 hour. The mixture is evaporated, taken up with ethyl acetate and water, washed with 1N hydrochloric acid, water and with a saturated solution of sodium chloride and then the organic phase is dried over sodium sulphate. The product obtained is chromatographed on silica by eluting with the ethyl acetate/heptane (10/90; v/v) mixture. 3.6 g of the expected product are collected.

D) Methyl ester of 2-((para-bromomethyl)phenyl)-2-methylpropionic acid.

The compound prepared in the preceding stage is treated with NBS and benzoyl peroxide according to the usual procedure.

E) Methyl ester of 2-[4-(2-n-butyl-4-spirocyclopentane-5-oxo-2-imidazol-1-yl)methylphenyl]-2-methylpropionic acid.

The compound prepared in the preceding stage is treated with 2-butyl-4-spirocyclopentane-2-imidazol-5-one according to the usual procedure.

F) 2-[4-(2-n-Butyl-4-spirocyclopentane-5-oxo-2-imidazol-1-yl)methylphenyl]-2-methylpropionic acid.

500 mg of the ester obtained in the preceding stage are brought to reflux for 3 hours in 5 ml of dioxan, 1.3 ml of water and 112 mg of sodium hydroxide. The mixture is evaporated, taken up with water, extracted with ether and then the aqueous phase is acidified to pH 5. It is extracted with ethyl acetate, dried over sodium sulphate and evaporated.

The product obtained is purified on a silica column by eluting with a hexane/AcOEt (5/5; v/v) mixture. 300 mg of the expected product are collected. m.p.=150° C.

NMR: 0.85 ppm: t: 3 H: $CH_3(nBu)$, 1.1-2.1 ppm: m: 18 H: $CH_3-CH_2-CH_2-+2CH_3$ (dimethyl)+cyclopentane 2.35 ppm: t: $\overline{2H}$: $-CH_2-CH_2-CH_2-CH_3$, 4.7 ppm: s: 2 H: $N-C\underline{H}_2-C_6H_4\overline{-}$, 7-7.6 ppm: m: 4 H: aromatic, 12.4 ppm: b.s.: 1 H: COOH—

EXAMPLE 18

2-n-Butyl-4-spirocyclopentane-1-[4-(2-((5-tetrazolyl)-methyl)isopropyl)benzyl]-2-imidazolin-5-one.

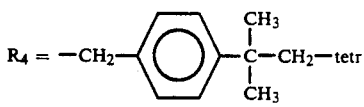

A) Ethyl ester of 2-cyano-3-(para-tolyl)-2-butenecarboxylic acid.

This compound is prepared according to Tetrahedron, 1959, 7; 236–240.

22.8 g of para-methylacetophenone, 19.2 g of ethyl cyanoacetate, 2.62 g of ammonium acetate and 8.17 g of acetic acid are mixed in 50 ml of anhydrous benzene and the mixture is brought to reflux for 20 hours in a flask equipped with a water separator. The organic phase is washed with water, dried over sodium sulphate, filtered and evaporated. The expected product is obtained by distillation under reduced pressure:

b.p.=136° C. at 0.6 mm Hg m=22.1 g

B) Ethyl ester of 2-cyano-3-methyl-3-(para-tolyl)-butyric acid.

This compound is prepared according to J. Am. Chem. Soc., 1957, 79. 4487.

39.9 ml of a 3M solution of methylmagnesium chloride in THF and 692 mg of copper iodide are placed in a flask and 20.8 g of the nitrile prepared in the preceding stage, in 50 ml of ether, are added dropwise. After heating for 4 hours at reflux, the mixture is hydrolysed with a saturated solution of ammonium chloride and is then extracted with ether, the organic phases are dried over sodium sulphate and evaporated. The product obtained is purified by chromatography on silica by eluting with an AcOEt/hexane (9/1; v/v) mixture. 10.8 g of the expected product are collected.

C) 2-Cyano-3-methyl-3-(para-tolyl)butyric acid.

10.8 g of the compound prepared in the preceding stage in 175 ml of dioxane and 45 ml of water containing 3.94 g of sodium hydroxide are brought to reflux for 3 hours. After evaporating, the mixture is taken up with water, extracted with ether and the aqueous phase is acidified to pH 5. It is extracted with ether; the extract is dried over sodium sulphate and evaporated. 9 g of the expected product are obtained.

D) 3-Methyl-3-(para-tolyl)butyronitrile.

The procedure is carried out according to Japanese Patent Application 78-124248. 9 g of the compound obtained in the preceding stage are brought to reflux for 5 hours in 50 ml of pyridine. The mixture is evaporated, taken up with ethyl acetate, washed with water, dried over sodium sulphate and concentrated. The product obtained is chromatographed on silica by eluting with the hexane-AcOEt (90/10; v/v) mixture. 3.84 g of the expected product are collected.

E) 2-n-Butyl-4-spirocyclopentane-1[4-(2-((5-tetrazolyl)methyl)isopropyl)benzyl]-2-imidazolin-5-one.

The preparation of the expected compound, characterised by its NMR spectra, is then carried out according to the usual methods.

NMR: 0.85 ppm: t: 3 H: $CH_3(nBu)$, 1.1-1.6 ppm: m: 10 H: $CH_3-CH_{22}-CH_2+\overline{2CH}_3$ (dimethyl), 1.6-2.1 ppm: m: 8 H: cyclopentane, 2.35 ppm: t: 2 H: $CH_3-CH_2-CH_2-CH_2$, 3.25 ppm: s: 2 H: $-CH_2$-tetrazole, 4.7 ppm: s: 2 $\overline{H}$: $N-CH_2-C_6H_4-$, 7-7.5 ppm: m: 4 H: aromatic

EXAMPLES 19 and 20

2-n-Butyl-1-[4-(3,3-dimethyl-1-(5-tetrazolyl)-1-buten-1-yl)benzyl]-4-spirocyclopentane-2-imidazolin-5-one, 2 isomers.

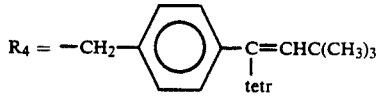

A) 4,4-Dimethyl-2-(para-tolyl)-2-pentenenitrile.

7 ml of LDA (1.5M in cyclohexane) and 15 ml of anhydrous THF are placed under argon, are cooled to −70° C. and 1.31 g of para-methylbenzyl cyanide in 10 ml of THF are added dropwise; after stirring for 30 minutes, 0.95 g of pivalaldehyde dissolved in 10 ml of THF are added dropwise, the mixture is left stirring for 1 hour at −70° C. and then for 1 hour at RT. The mixture is poured onto an ice/hydrochloric acid mixture, extracted with AcOEt and then washed with a saturated solution of sodium chloride. The product obtained is chromatographed on silica by eluting with a DCM/hexane (2/8; v/v) mixture. 1.3 g of the expected product are collected.

B) 3,3-Dimethyl-1-(5-tetrazolyl)-1-(para-tolyl)-1-butene.

1.27 g of the nitrile prepared in the preceding stage and 3.2 g of tributyltin azide are heated to reflux for 90 hours in 20 ml of xylene. After returning to RT, the organic phase is extracted with 1N sodium hydroxide, washed with ether, the aqueous phase is acidified to pH 2, extracted with AcOEt; the extract is dried and evaporated. 1.2 g of the expected product are obtained.

C) 3,3-Dimethyl-1-(1-trityl-5-tetrazolyl)-1-(paratolyl)-1-butene.

1.2 g of the product obtained in the preceding stage is brought to reflux for 3 hours in 25 ml of DCM containing 1.52 g of trityl chloride and 1 ml of triethylamine. The mixture is evaporated, taken up with ethyl acetate, washed with water and then with a 3% solution of potassium hydrogen sulphate, dried over sodium sulphate and evaporated. 2.6 g of the expected product, which crystallises, are obtained.

D) 1-(para-Bromomethyl)phenyl-3,3-dimethyl-1-(1-trityl-5-tetrazolyl)-1-butene.

2.6 g of the product obtained in the preceding stage and 906 mg of NBS are brought to reflux for 4 hours in 40 ml of carbon tetrachloride containing 50 mg of benzoyl peroxide. After returning to RT, the mixture is filtered and evaporated to obtain the crude expected product.

E) 2-n-Butyl-1-[4-(3,3-dimethyl-1-(1-trityl-5-tetrazolyl)-1-buten-1-yl)benzyl]-4-spirocyclopentane-2-imidazolin-5-one.

370 mg of 80% sodium hydride in oil and 10 ml of DMF are placed under argon and 680 mg of 2-n-butyl-4-spirocyclopentane-2-imidazolin-5-one in 10 ml of DMF are added dropwise; the brominated compound obtained in the preceding stage, dissolved in 20 ml of DMF, is added and the mixture is left for 1 hour at RT. The mixture is evaporated, taken up with AcOEt and water, the organic phase is dried over sodium sulphate, filtered and evaporated. The crude product obtained is chromatographed on silica by eluting with a hexane-AcOEt (7/3; v/v) mixture. 2 isomers of the expected product are obtained, the configurations of which are determined by the N.O.E. effect.
Compound a: 550 mg: Z isomer
Compound b: 650 mg: E isomer F) 2-n-Butyl-1-[4-(3,3-dimethyl-1-(5-tetrazolyl)-1-buten-1-yl)benzyl]-4-spirocyclopentane-2-imidazolin-5-one, (Z) isomer.

490 mg of the compound a), obtained above, are placed in 10 ml of THF, a few drops of 3N hydrochloric acid are added to reach a pH of 2 and the mixture is left stirring for 2 hours at RT. The mixture is evaporated, taken up with ether, a solution of 1N sodium hydroxide and is then extracted with AcOEt. The aqueous phase is acidifed to pH 5 and is extracted with AcOEt. The extract is dried over sodium sulphate, filtered and evaporated. The crude product is eluted on a silica column with the DCM/methanol (95/5; v/v) mixture. m=290 mg is obtained.

m.p.=85°-90° C.

NMR: 0.8 ppm: t: 3 H: CH3(nBu), 0.9 ppm: s: 9 H: (tBu), 1.25 ppm: sext: 2 H: CH3—CH2—, 1.5 ppm: quint: 2 H: CH3—CH2—CH2—, 1.6-2 ppm: m: 8 H: cyclopentane, 2.3 ppm: t: 2 H: CH3—CH2—CH2—CH2—, 4.75 ppm: s: 2 H: N—CH2—C6H4—, 6.8 ppm: s: 1 H: =C—H, 7.1-7.3 ppm: m: 4 H: aromatic G) 2-n-Butyl-1-[4-(3,3-dimethyl-1-(5-tetrazolyl)-1-buten-1-yl)benzyl]-4-spirocyclopentane-2-imidazolin-5-one, (E) isomer.

510 mg of the compound b obtained in stage E are placed in 10 ml of methanol and 10 ml of THF, 2N hydrochloric acid is added to reach a pH of 2 and the mixture is left stirring for 5 hours. The product obtained is treated as in stage F and is then chromatographed on silica by eluting with the DCM/methanol (97/3; v/v) mixture. m=235 mg is obtained.

m.p.=160°-162° C.

NMR: 0.7 ppm: t: 3 H: CH3(nBu), 0.8 ppm: s: 9 H: (tBu), 1-1.9 ppm: m: 12 H: CH3—CH2—CH2—+cyclopentane, 2.2 ppm: t: 2 H: CH3—CH2—CH2—CH2—, 4.55 ppm: s: 2 H: N—CH2—C6H4—, 6.45 ppm: s: 1 H: =CH, 7 ppm: s: 4 H: aromatic

EXAMPLE 21

(Z)-2-n-Butyl-1-[4-(3,3-dimethyl-2-(5-tetrazolyl)-1-buten-1-yl)benzyl]-4-spirocyclopentane-2-imidazolin-5-one.

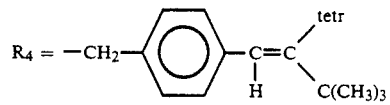

A) Diethyl (2,2-bis(methylthio)-1-cyanoethene)phosphonate.

The preparation of this compound is described by E. Schaumann et al. in Liebigs Ann. Chem., 1979, 1715-1733.

B) Diethyl (1-cyano-2,2-dimethylpropane)phosphonate.

The preparation of this compound is described by E. Schaumann et al. in Synthesis, 1983, 449-450.

C) (Z)-1-(para-Tolyl)-2-cyano-3,3-dimethyl-1-butene.

1.6 g of the compound prepared in the preceding stage, in 10 ml of THF, and a suspension of 226 mg of 80% sodium hydride in oil in 20 ml of THF are mixed under nitrogen. The mixture is stirred for 30 minutes at RT and then 0.89 ml of para-tolualdehyde in 20 ml of THF are added. After 18 hours at RT and 2 hours of heating at reflux, the mixture is poured onto ice, extracted with DCM, dried over sodium sulphate and concentrated. The crude product obtained is chromatographed on silica by eluting with a DCM/heptane (8/2; v/v) mixture. 920 mg of an oily product are isolated. The Z isomer is recognised by analysis of the NMR spectrum by the N.O.E. effect.

D) (Z)-1-(para-Bromomethyl)phenyl-2-cyano-3,3-dimethyl-1-butene.

A mixture containing 850 mg of the compound prepared in the preceding stage, 760 mg of NBS, 80 mg of benzoyl peroxide and 40 ml of carbon tetrachloride are brought to reflux for 3 hours. After cooling, the mixture is filtered, washed with carbon tetrachloride and concentrated to dryness. 1.4 g of crude product, which is used as such in the following stage, are obtained.

E) (Z)-2-n-Butyl-1-[4-(3,3-dimethyl-2-cyano-1-buten-1-yl)benzyl]-4-spirocyclopentane-2-imidazolin-5-one.

This compound is prepared according to the usual procedure by addition of 2-n-butyl-4-spirocyclopentane-2-imidazolin-5-one to the product prepared in the preceding stage.

F) (Z)-2-n-Butyl-1-[4-(3,3-dimethyl-2-(5-tetrazolyl)-1-buten-1-yl)benzyl]-4-spirocyclopentane-2-imidazolin-5-one.

A mixture containing 1 g of the compound obtained in the preceding stage and 1.6 g of tributyltin are brought to reflux for 90 hours in 30 ml of xylene.

The mixture is extracted with 2N sodium hydroxide and the aqueous phase is then acidified with 2N hydrochloric acid to a pH of 5; it is extracted with AcOEt, dried over sodium sulphate and concentrated. The product obtained is chromatographed on silica by eluting with a DCM/methanol (95/5; v/v) mixture. 220 mg of a white solid are isolated.

m.p.=80° C.

The Z isomer is recognised by analysis of the NMR spectrum with the N.O.E. effect. Thus, the hydrogen and the tert-butyl are at the cis position on the double bond.

NMR: 0.8 ppm: t: 3 H: CH$_3$(nBu), 1–1.35 ppm: m: 11 H: (tBu)+CH$_3$—C$\underline{H}_2$—, 1.45 ppm: quint: 2 H: CH$_3$—CH$_2$—C$\underline{H}_2$—, 1.45–2 ppm: m: 8 H: cyclopentane, 2.2 ppm: t: 2 H: —CH$_3$—CH$_2$—CH$_2$—C$\underline{H}_2$—, 4.6 ppm: s: 2 H: N—C$\underline{H}_2$—C$_6$H$_4$—, 6.7–7.1 ppm: m: 5 H: aromatic+=CH,

EXAMPLE 22

2-n-butyl-1-[(2'-carboxy-4-biphenylyl)methoxy]-4-spirocyclopentane-2-imidazolin-5-one trifluoroacetate.

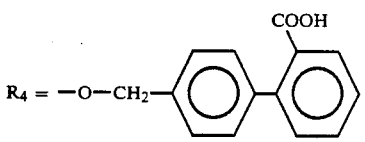

The first two stages of this process are carried out according to A. F. McKay et al. in Can. J. Chem., 960, 38, 343.

A) N-[(2'-tert-Butoxycarbonyl-4-biphenylyl)methoxy]phthalimide.

4.66 ml of DIPEA and 6.26 g of 4-bromomethyl(2'-tert-butoxycarbonyl)biphenyl are added successively to a solution of 2.95 g of N-hydroxyphthalimide in 30 ml of DMF. The mixture is left stirring for 2 hours at RT and for 4 hours at 80° C. and then the reaction mixture is taken up with 250 ml of ethyl acetate, and washed successively with 50 ml of water, a saturated solution of sodium hydrogen carbonate, with a saturated solution of sodium chloride, a 5% solution of KHSO$_4$—K$_2$SO$_4$ and then a saturated solution of sodium chloride. After drying and concentrating, the residue is recrystallised from a methanol-water mixture.

m=7.15 g m.p.=140°–145° C.

B) (2'-tert-Butoxycarbonyl-4-biphenylyl)methoxyamine.

6.96 g of the compound obtained in the preceding stage is brought to reflux for 4 hours in 15 ml of DCM and 1 ml of ethanolamine. The mixture is concentrated, taken up with DCM, washed successively with water, with a saturated solution of NaHCO$_3$ and a saturated solution of NaCl. After drying over sodium sulphate, the organic phase is concentrated and the residue is triturated in ether. An insoluble solid is removed and then the filtrate is concentrated and purified by chromatography by eluting with the DCM/MeOH (8/2; v/v) mixture. 4 g of the expected compound are obtained in the form of an oil.

C) N-[(2°-tert-Butoxycarbonyl-4-biphenylyl)methoxy]-1-(N-benzyloxycarbonylamino)cyclopentanecarboxamide.

The N-benzyloxycarbonylcyclopentylcarboxylic acid is prepared according to Tet. Lett., 1966, 4765.

1.65 g of this acid and 2.79 g of BOP are added to 1.51 g of the compound prepared in the preceding stage in solution in 20 ml of DCM and the mixture is held at pH 7 by the addition of DIPEA. After 8 hours at RT, the reaction mixture is concentrated, taken up with ethyl acetate and washed successively with water, a 5% solution of KHSO$_4$—K$_2$SO$_4$, a saturated solution of NaCl, a saturated solution of NaHCO$_3$ and a saturated solution of NaCl. After drying over sodium sulphate, the organic phase is concentrated and purified on a silica column by eluting with the hexane/AcOEt (6/4; v/v) mixture. The pure fractions are concentrated to give the expected product in the form of a white solid.

m=2.31 g m.p.=137°–138° C.

D) N-[(2'-tert-Butoxycarbonyl-4-biphenylyl)methoxy]-1-aminocyclopentanecarboxamide.

2.2 g of the compound prepared in the preceding stage are taken into solution in 20 ml of THF and are hydrogenated at atmospheric pressure for 2 hours in the presence of 400 mg of 10% palladium on charcoal. The catalyst is filtered off and the filtrate is concentrated and then the residue is triturated in an etherhexane (1/1; v/v) mixture. The solid obtained is filtered off and washed with hexane.

m=800 mg.

E) 2-n-Butyl-1-[(2'-tert-butoxycarbonyl-4-biphenylyl)methoxy]-4-spirocyclopentane-2-imidazolin-5-one.

750 mg of the compound prepared in the preceding stage are treated with 270 µl of methyl orthovalerate in the presence of a few drops of acetic acid at 110° C. for 1 hour. The reaction mixture is taken up with 50 ml of AcOEt, washed in the usual manner and then dried over sodium sulphate. 860 mg of the expected compound are obtained in the form of an oil.

NMR: 0.8 ppm: t: 3 H: CH$_3$(nBu), 1.2 ppm: s: 9 H: (tBu), 1.2–1.8 ppm: m: 12 H: cyclopentane+CH$_2$—CH$_2$—CH$_3$, 2.2 ppm: t: 2 H: C$\underline{H}_2$—CH$_2$—CH$_2$—CH$_3$, 5.1 ppm: s: 2 H: OC$\underline{H}_2$, 7.2–7.65 ppm: m: 8 H: aromatic, F) 2-n-butyl-1-[(2'-carboxy-4-biphenylyl)methoxy]-4-spirocyclopentane-2-imidazolin-5-one trifluoro acetate.

830 mg of the preceding compound are treated at RT for 30 minutes with 10 ml of TFA in 7 ml of DCM. The solution is concentrated to dryness and the residue is recrystallised from a hexane-ether mixture to obtain the expected product.

m=825 mg

MP=143°–145° C.

NMR: 0.9 g ppm: t: 3 H: CH$_3$(nBu), 1.3 ppm: sext: 2 H: CH$_3$—C$\underline{H}_2$—, 1.5 ppm: quint: 2 H: CH$_3$—CH$_2$—C$\underline{H}_2$—, 1.6–2 ppm: m: 8 H: cyclopentane, 2.35 ppm: t: 2 H: C$\underline{H}_2$—CH$_2$—CH$_2$—CH$_3$, 5.2 ppm: s: 2 H: OC$\underline{H}_2$, 7.39–7.8 ppm: m: 8 H: aromatic

EXAMPLE 23

2-n-butyl-1-[(2'-carboxy-4-biphenylyl)amino]-4-spirocyclohexane-2-imidazolin-5-one dihydrochloride.

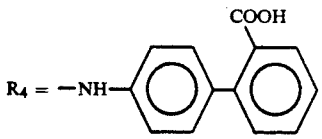

A) 4'-Amino-2-biphenylcarboxylic acid is prepared according to S. A. Glover et al. (J. Chem. Soc., Perkin I, 1981, 842).

B) 4'-Hydrazino-2-biphenylcarboxylic acid.

This compound is prepared according to J. Witte et al., J. Org. Chem., 1972, 37 (18), 2849. 235 mg of sodium nitrite dissolved in 2 ml of water are added to a solution, at −10° C., of 716 mg of the compound prepared in stage A in 2 ml of hydrochloric acid and 2 g of ice. After 10 minutes, a solution at −10° C. of 1.8 g of $SnCl_2.2H_2O$ in 8.5 ml of concentrated hydrochloric acid is added in 4 portions. After 30 minutes, the mixture is adjusted to pH 7 by the addition of sodium hydroxide. The solid obtained is filtered off, the filtrate is concentrated and taken up with MeOH in order to remove the precipitate formed. After concentrating the filtrate and triturating in ethanol, a pink solid (270 mg) is obtained which is used immediately for the following stage.

C) methyl ester of 4'-hydrazino-2-biphenylcarboxylic acid hydrochloride.

0.5 mg of thionyl chloride are mixed while cold in 5 ml of methanol, after stirring for 15 minutes, 310 mg of the compound prepared previously are added in 5 ml of methanol and the mixture is brought to reflux for 2 hours. The mixture is concentrated, taken up with cold absolute ethanol, an insoluble solid is removed and the filtrate is concentrated in order to give the expected product in the form of an oil (310 mg).

D) 1-Aminocyclohexanecarboxylic acid is commercially available, and it allows the preparation of N-benzyloxycarbonyl-1-aminocyclohexanecarboxylic acid.

E) 2-n-butyl-1-[(2'-carboxy-4-biphenylyl)amino]-4-spirocyclohexane-2-imidazolin-5-one dihydrochloride.

The various stages described in the preceding example are then carried out in order to prepare the methyl ester of the expected product and then the product itself.

mass spectrum: MH+: 420

NMR: 0.9 ppm: t: 3 H: $CH_3$(nBu), 1.15-2.2 ppm: m: 14 H: cyclohexane and, —$CH_2$—$CH_2$—$CH_3$, 2.6 ppm: t: 2 H: —$C\underline{H}_2$—$CH_2$—$CH_2$—$\overline{C}H_3$, 6.7-7.8 ppm: m: 8 H: aromatic

EXAMPLE 24

2-n-Butyl-1-(2'-carboxy-4-biphenylyl)-4-spirocyclohexane-2-imidazolin-5-one.

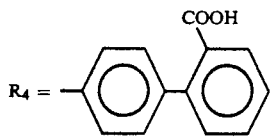

A) Methyl ester of 4'-amino-2-biphenylcarboxylic acid.

This compound is obtained from the corresponding acid described in stage A of the preceding example. 700 mg of the acid are treated with methanol saturated with hydrogen chloride gas and are brought to reflux for 3 hours. The mixture is concentrated and then taken up with 50 ml of water. The aqueous phase is washed twice with 10 ml of AcOEt and then a concentrated solution of $NaHCO_3$ is added. It is extracted 3 times with 20 ml of AcOEt; the extract is dried and concentrated. The expected product is obtained in the form of an oil (330 mg) which is used as such in the following stage (330 mg).

B) 2-n-Butyl-1-(2'-methoxycarbonyl-4-biphenylyl)-4-spirocyclohexane-2-imidazolin-5-one.

N-Benzyloxycarbonyl-1-aminocyclohexanecarboxylic acid is prepared and then this acid is coupled to the product prepared in stage A and the stages described in Example 22 are carried out to obtain the expected product.

NMR: 0.85 ppm: t: 3 H: $CH_3$(nBu), 1.25-1.8 ppm: m: 14 H: cyclohexane and $C\underline{H}_2$—$CH_2$—$CH_3$, 2.4 ppm: t: 2 H: $C\underline{H}_2$—$CH_2$—$CH_2$—$\overline{C}H_3$, 3.65 ppm: s: 3 H: $CO_2CH_3$, 7.4-7.9 ppm: m: 8 H: aromatic C) 2-n-Butyl-1-(2'-carboxy-4-biphenylyl)-4-spirocyclohexane-2-imidazolin-5-one.

320 mg of the compound prepared in the preceding stage are taken into solution in 10 ml of ethanol and treated with 2.1 ml of 10% sodium hydroxide for 1 hour at reflux. The mixture is concentrated, then taken up with 5 ml of water and acidified by the addition of acetic acid. The precipitate formed is filtered off, washed with water and dried over phosphorus pentoxide. 200 mg of the expected product are obtained.

m.p.=85°–90° C.

NMR: 0.7 ppm: t: 3 H: $CH_3$(nBu), 1.1-1.7 ppm: m: 14 H: cyclohexane and —$CH_2$—$CH_2$—$CH_3$, 2.2 ppm: t: 2 H: $C\underline{H}_2$—$CH_2$—$CH_2$—$\overline{C}H_3$, 7.15-7.7 ppm: m: 8 H: aromatic, 12.6 ppm: s: 1 H: $CO_2H$.

EXAMPLE 25

2-n-Butyl-1-[(2'-carboxy-4-biphenylyl)carbonyl]-4-spirocyclopentane-2-imidazolin-5-one.

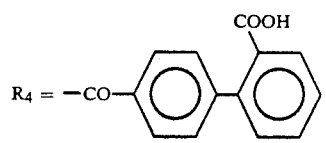

A) 2'-tert-Butoxycarbonyl-4-biphenylcarboxylic acid.

This compound is prepared according to S. Cacchi et al., Chem. Ind., 1986, 286.

3 g of 4-bromomethyl-(2'-tert-butoxycarbonyl)biphenyl in solution in 37 ml of acetonitrile and 5 ml of DCM are treated with 27.6 ml of an aqueous sodium hypochlorite solution, containing 15% of chlorine, in the presence of 2.95 g of tetrabutylammonium hydrogen sulphate. After stirring for 24 hours at RT, 200 ml of ether and 50 ml of water are added. The organic phase is washed with 100 ml of water, dried and concentrated to give a yellow oil which is purified by chromatography on silica by eluting with the heptane/AcOEt/AcOH (80/20/2; v/v/v) mixture, 1.02 g of the expected product are obtained.

m.p.=174°–176° C.

B) 2-n-Butyl-1-[(2'-tert-butoxycarbonyl-4-biphenylyl)carbonyl]-4-spirocyclopentane-2-imidazolin-5-one.

485 mg of the compound prepared in the preceding stage in solution in DCM are treated with 335 mg of DCC for 15 minutes, then 315 mg of 2-n-butyl-4-spirocyclopentane-2-imidazolin-5-one are added and then 50 mg of DMAP. After stirring for 24 hours, the reaction mixture is filtered, the filtrate is purified and concentrated by chromatography on silica by eluting with the hexane/AcOEt (9/1; v/v) mixture. The expected product is obtained in the form of an oil.

m=200 mg.

NMR: 0.8 ppm: t: 3 H: $CH_3$(nBU), 1.2 ppm: s: 9 H: (tBU), 1.25-2 ppm: m: 12 H: cyclopentane+C-$\underline{H}_3$—$CH_2H_2$—$CH_2$—, 2.7 pp: t: 2 H: $C\underline{H}_2$—$CH_2$C-$H_2$—$C\overline{H}_3$—, 7.35-7.85 ppm: m: 8 H: aromatic C) 2-n-Butyl-1[(2'-carboxy-4-biphenyl)carbonyl]-4-spirocyclopentane-2-imidazolin-5-one.

222 mg of the compound obtained in the preceding stage are treated for 1 hour and a half with 4 ml of TFA and 4 ml of DCM. After concentrating the mixture, the residue is triturated in an ether-hexane (1/1; v/v) mixture. The expected product is obtained in the form of a white powder which is unstable at RT.

NMR: 0.8 ppm: t: 3 H: $CH_3$(nBU), 1.2-2.0 ppm: m: 12 H: cyclopentane, $CH_2$—$CH_2$—$CH_2$, 2.6 ppm: t: 2 H: $C\underline{H}_2$—$CH_2CH_2$—$CH_3$—, 7.2-7.9 ppm: m: 8 H: aromatic

EXAMPLES 26 AND 27

2-n-Butyl-4-spirocyclopentane-1-[4-(1-(5-tetrazolyl)-1-butyl)benzyl]-2-imidazolin-5one.

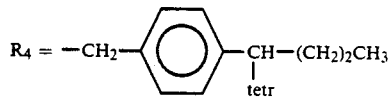

and 2-n-butyl-4-spirocyclopentane-1-[4(1-(5-tetrazolyl)-1-buten-1-yl)benzyl]-2-imidazolin-5-one.

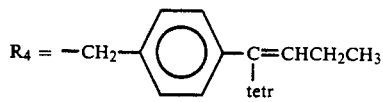

A) 1-[1-trityl-5-tetrazolyl]-1-[para-tolyl]-butane.

By proceeding as in the first stages described for Examples 10 and 16, butyl 2-(para-tolyl)pentanenitrile is prepared, then the cyano group is converted to tetrazole and then to 1-trityltetrazole.

B) 1-[1-trityl-5-tetrazolyl]-1-[para-(bromomethyl)phenyl]-butane and 1-[1-trityl-5-tetrazolyl]-1-[para-(bromomethyl)phenyl]-2-bromobutane.

4 g of the compound prepared in stage A) are treated with 1.7 g of NBS in the presence of 205 mg of benzoyl peroxide in 55 ml of carbon tetrachloride. After 3 hours at reflux and return to RT, the succinimide formed is filtered off and is then evaporated. The presence of the 2 brominated compounds is identified by thin layer chromatography. They are used as such in the following stage.

C) 2-n-Butyl-4-spirocyclopentane-1-[4-(1-(1-trityl-5-tetrazolyl)-1-butyl)benzyl]-2-imidazolin-5-one and 2-n-butyl-4-spirocyclopentane-1-[4-(1-(1-trityl-5-tetrazolyl)-1-buten-1-yl)benzyl]-2-imidazolin-5-one.

10 ml of DMF are placed in an argon atmosphere and 1.24 g of 80% sodium hydride in oil and 504 mg of imidazolinone in 10 ml of DMF are added. After 30 minutes at RT, 2.09 g of the mixture of products obtained in stage B) are added dropwise. After stirring for 5 hours at RT, the mixture is evaporated, taken up with ethyl acetate, washed with water and then with a saturated solution of NaCl, is dried over sodium sulphate and concentrated. The product obtained is chromatographed on alumina by eluting with a hexane/AcOEt (8/2; v/v) mixture. 1.7 g of the mixture of the expected products are obtained.

D) 2-n-Butyl-4-spirocyclopentane-1-[4-(1-(5-tetrazolyl)-1-butyl)benzyl]-2-imidazolin-5-one and 2-n-butyl-4-spirocyclopentane-1-[4-(1-(5-tetrazolyl)-1-buten-1-yl)benzyl]-2-imidazolin-5-one.

1 g of the mixture obtained in the preceding stage is placed in 5 ml of methanol; the mixture is cooled to 0° C. and 0.8 ml of 4N hydrochloric acid are added and the mixture is then left stirring for 3 and a half hours. After evaporating, the mixture is taken up with water, sodium hydroxide is added to bring to a pH of 13, then the mixture is washed with ether, with toluene and then again with ether. The pH is adjusted to 5 by the addition of hydrochloric acid and the mixture is then extracted with ethyl acetate, dried over sodium sulphate and concentrated. The mixture obtained is chromatographed on silica and the 2 products are separated by eluting with a DCM/MeOHAcOH (98/2/1; v/v/v) mixture. 90 mg of the compound of Example 26 (as butyl) and 50 mg of the compound of Example 27 (as butene) are collected.

NMR (Example 26): 0.5-0.9 ppm: m: 6 H: $CH_3$(nBu), 0.9-1.45 ppm: m: 6 H: $CH_3CH_2$—$CH_2$—(nBu)+$CH_3C$-$\underline{H}_2$—$C\underline{H}_2$ butyl, 1.45-2 ppm: m: 10 H: $CH_3$—$CH_2$—$CH_2$—(butyl)+cyclopentane, 2.2 ppm: t: 2 H: $CH_3$—$C\overline{H}$-$_2$—$CH_2$—$CH_2$—(nBu), 4.25 ppm: t: 1 H: —$CH$—$C_6$-$H_4$—, 4.55 ppm: s: 2 H: —N—$C\underline{H}_2$—$C_6H_4$, 6.9-7.2 ppm: m: 4 H: aromatic NMR (Example 27): 0.5-1.05 ppm: m: 6 H: $CH_3$(nBu)$CH_3$(butene), 1.2 ppm: sext: 2 H: $CH_3$—$CH_2$(nBu), 1.4 ppm: quint: 2 H: $CH_3$—$CH_2$-$CH_2$(nBu), 1.5-1.9 ppm: m: 8 H: cyclopentane, 1.9-2.4: m: 4 H: $CH_3$—$CH_2$—$CH_2$—$CH_2$(nBu)+ 4.65: split s: 2 H: —N—$C\underline{H}_2$—$C_6H_4$—, 6.4-6.8: split t: 1 H: =$C\underline{H}$, 6.9-7.4: m: 4 H: aromatic

EXAMPLE 28 n-Butyl-1-[4-(cyclohexyl-(5-tetrazolyl)methyl)benzyl]-4-spirocyclopentane-2-imidazolin-5-one.

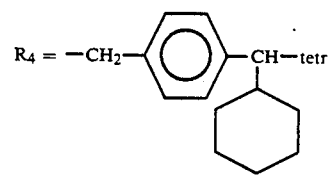

By proceeding as in Example 16, 1-[cyano-(p-tolyl)-methyl]cyclohexane is prepared first by the action of bromocyclohexane on para-methylbenzyl cyanide. The following stages are carried out under the usual conditions which make it possible to obtain the expected product.

NMR: 0.6 ppm: t: 3 H: CH₃(nBu), 0.65-1.9 ppm: m: 22 H: CH₃—CH₂—CH₂—+cyclopentane+CH₂—(cyclohexyl), 1.9-2.3 ppm: m: 3 H: CH₂—CH₂—CH₂—CH₃+CH(cyclohexyl) 2.5 ppm: m: 2 H: CH₂—CH₂—CH₂—CH₃ 3.95 ppm: d: 1 H: CH₂—C₆H₄ 4.35 ppm: s: 2 H: —N—CH₂—C₆H₄— 6.8-7.4 ppm: m: 4 H: H aromatic

EXAMPLE 29

2-n-Butyl-4-spirocyclopentane-1-[4-(3-(5-tetrazolyl)-2,3-dimethyl-2-butyl)benzyl]-2imidazolin-5-one.

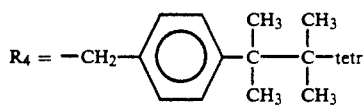

A) 3-Methyl-3-(para-tolyl)butyrontrile.

This compound is prepared in Example 18, stage D).

B) 2,2,3-Trimethyl-3-(para-tolyl)butyronitrile.

20 ml of anhydrous THF are placed at 0° C. under a nitrogen atmosphere and then 32 ml of LDA (1.5M in cyclohexane) in 10 ml of THF and 2.1 g of the nitrile prepared in stage A) in 5 ml of THF are added dropwise. After stirring for 15 minutes, 6.1 ml of methyl iodide in 5 ml of THF are added dropwise. The mixture is allowed to return to RT and is then brought to reflux for 2 and a half hours. After evaporating, the mixture is taken up with ethyl acetate, washed with water and then successively with a solution of KHSO₄, water and a saturated solution of NaCl. It is dried over sodium sulphate and the organic phases are then concentrated. Chromatography is then carried out on silica by eluting with an AcOEt/hexane (5/95; v/v) mixture. 2 g of the expected product are obtained.

C) 2-n-Butyl-4-spirocyclopentane-1-[4-(3-(5-tetrazolyl)-2,3-dimethyl-2-butyl)benzyl]-2-imidazolin-5-one.

By proceeding according to the usual methods, the expected product is prepared.

NMR: 0.7 ppm: t: 3 H: CH₃(nBu), 1-1.5 ppm: m: 16 H: CH₃—CH₂—CH₂—+4CH₃, 1.5-1.9: m: 8 H: cyclopentane, 2.2 ppm: t: 2 H: CH₃—CH₂—CH₂—, 4.55: s: 2 H: —N—CH₂-C₆H₄—, 6.55: m: 4 H: aromatic

EXAMPLE 30

2-n-Butyl-1-[4-(3,3-dimethyl-1-(5-tetrazolyl)-1-buten-2-yl)benzyl]-4-spirocyclopentane-2-imidazolin-5-one

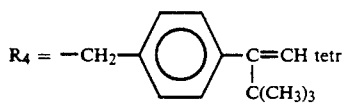

A) tert-Butyl-(para-tolyl)ketone.

This compound is prepared according to J. Am. Chem. Soc., 1950, 4169.

B) 4,4-Dimethyl-3-(para-tolyl)-2-pentenenitrile.

This compound is prepared according to Chem. Pharm. Bull., 1980, 1394.

2.15 g of sodium are dissolved in 70 ml of ethanol, the solution is then cooled in an ice bath and 16.46 g of diethyl cyanomethylphosphonate are added dropwise. After stirring for 10 minutes at 10° C., 13.9 g of the ketone prepared in the preceding stage are added and the mixture is left stirring for 1 hour at RT, then for 18 hours at 60° C. After evaporating, the mixture is taken up with ether; the solution is washed with water and with a saturated solution of sodium chloride and is then dried over sodium sulphate. After concentrating the organic phases, these are purified by chromatography on silica by eluting with an AcOEt/hexane (5/95; v/v) mixture. 7.57 g of the expected product are obtained.

C) 2-n-Butyl-1-[4-(3,3-dimethyl-1-(5-tetrazolyl)-1-buten-2-yl)benzyl]-4-spirocyclopentane-2-imidazolin-5-one.

The usual stages are carried out in order to prepare the expected product, characterised by its melting point.

m.p.=145° C.

EXAMPLES 31 AND 31a 2-n-Butyl-1-[4-(α-(5-tetrazolyl)benzyl)benzyl]-4-spirocyclopentane-2-imidazolin-5-one.

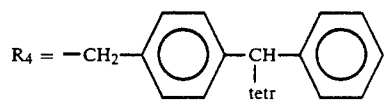

and 2-n-Butyl-1-[4-((α-hydroxyl-α-(5-tetrazolyl))benzyl)benzyl]-4-spirocyclopentane-2-imidazolin-5-one

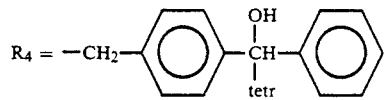

A) para-Tolylphenylacetonitrile is prepared according to K. Sisido in J. Org. Chem., 1954, 19, 1699.

B) Phenyl-(para-tolyl)-5-tetrazolylmethane.

1.12 g of the compound of stage A are treated with 1.8 g of tributyltin azide in 10 ml of xylene and are brought to reflux for 3 days. The mixture is taken up with 50 ml of a 5% aqueous solution of sodium hydroxide and with 50 ml of ether. The ethereal phase is washed with 50 ml of a 5% aqueous solution of sodium hydroxide; the combined aqueous phases are washed with 20 ml of ether and then acidified with concentrated hydrochloric acid to a pH of 2. The precipitate obtained is filtered off, washed with water and dried under vacuum over phosphoric anhydride. 1.15 g of the solid.

m.p.=148°-150° C.

NMR: 2.2 ppm: s: 3 H: —C₆H₄—CH₃, 5.85 ppm: s: 1 H: —C₆H₄—CH—C₆H₅, 7.1-7.4 ppm: m: 9 H: aromatic C) [Phenyl-(para-tolyl)-(trityl-5-tetrazolyl)]methane.

1.15 g of the product prepared in the preceding stage are mixed in 25 ml of DCM with 1.54 g of trityl chloride and 1.1 ml of triethylamine and the mixture is heated at reflux for 3 hours. The solution is concentrated under vacuum, taken up with ethyl acetate, washed twice with water and then with a saturated solution of sodium chloride. It is dried over sodium sulphate, partially concentrated and then filtered on silica. After concentrating, a white foam is obtained which is used as such in the following stage.

NMR: 2.3 ppm: s: 3 H: —C₆H₄—CH₃ 6.0 ppm: s: 1 H: —C₆H₄—CH—C₆H₅ 7.0-7.5 ppm: m: 24 H: aromatic D) [((4-Bromomethyl)phenyl)phenyl(trityl-5-tetrazolyl)]methane.

The crude product obtained in the preceding stage (4.6 mmol) is treated with 820 mg of NBS and 30 mg of benzoyl peroxide in 20 ml of carbon tetrachloride and the mixture is brought to reflux under UV radiation for 1 and a half hours. The mixture is filtered, the solid is washed with carbon tetrachloride and the filtrate is concentrated under vacuum. The foam obtained is used as such in the following stage.

E) 2-n-Butyl-1-[4-(α-(trityl-5-tetrazolyl)benzyl)benzyl]-4-spirocyclopentane-2-imidazolin-5-one.

740 mg of the hydrochloride of 2-n-butyl-4-spirocyclopentane-2-imidazolin-5-one are added to 0.193 g of 80% sodium hydride in oil and 10 ml of DMF. After 15 minutes at RT under argon, the crude product obtained in the preceding stage is added at 0° C. After stirring for 3 hours under argon at RT, the reaction mixture is concentrated under vacuum, the residue is then taken up in ethyl acetate and is washed successively with water, a saturated solution of sodium hydrogen carbonate and a saturated solution of sodium chloride. After drying over sodium sulphate and concentrating under vacuum, the oil obtained is chromatographed on silica by eluting with a heptane/ethyl acetate (7/3; v/v) mixture. 2 fractions are obtained; the less polar fraction consists of 400 mg of the expected product in the form of a white foam.

NMR: 0.85 ppm: t: 3 H: CH$_3$(nBu), 1.25 ppm: sext: 2 H: CH$_3$—CH$_2$, 1.45 ppm: quint: 2 H: CH$_3$—CH$_2$—CH$_2$, 1.6–2.0 ppm: m: 8 H: cyclopentane, 2.35 ppm: t: 2 H: CH$_3$—CH$_2$—CH$_2$—CH$_2$—, 4.7 ppm: s: 2 H: —N—CH$_2$—C$_6$H$_4$—, 6.05 ppm: s: 1 H: —C$_6$H$_4$—CH—C$_6$H$_5$, 7.0–7.5 ppm: m: 24 H: aromatic The more polar fraction consists of the following product: 2-n-butyl-1-[4-((α-hydroxyl-α-(trityl-5-tetrazolyl))benzyl)benzyl]-4-spirocyclopentane-2-imidazolin-5-one.

F) 2-n-Butyl-1-[4-(α-(5-tetrazolyl)benzyl)benzyl]-4-spirocyclopentane-2-imidazolin-5-one.

370 mg of the product obtained in the preceding stage (the less polar fraction) are placed in 5 ml of DCM and are treated with 5 ml of formic acid and 0.75 ml of water. After 3 hours, the mixture is concentrated to dryness and is then chromatographed on silica by eluting with a heptane/acetone/acetic acid (75/35/1) mixture. The pure fractions are concentrated to dryness. The residue is taken up in an ether-hexane mixture and is concentrated under vacuum so that a dry foam is obtained.

m = 200 mg

NMR: 0.75 ppm: t: 3 H: CH$_3$(nBu), 1.2 ppm: sext: 2 H: CH$_3$—CH$_2$. 1.4 ppm: quint: 2 H: CH$_3$—CH$_2$—CH$_2$, 1.6–1.9 g ppm: m: 8 H: cyclopentane, 2.3 ppm: t: 2 H: CH$_3$—CH$_2$—CH$_2$—CH$_2$—, 4.65 ppm: s: 2 H: —N—CH$_2$—C$_6$H$_4$—, 5.9 ppm: s: 1 H: —C$_6$H$_4$—CH—C$_6$H$_5$, 7.0–7.4 ppm: m: 9 H: aromatic G) 2-n-Butyl-1-[4-((α-hydroxyl-α-(5-tetrazolyl))benzyl)benzyl]-4-spirocyclopentane-2-imidazolin-5-one.

400 g of the compound obtained in stage E) (the more polar fraction) are dissolved in 5 ml of DCM and treated with 5 ml of formic acid and 0.75 ml of water at RT for 4 hours. The reaction mixture is concentrated and the residue is chromatographed on silica by eluting with a heptane/acetone/AcOH (70/30/1; v/v/v) mixture. The pure fractions are combined and concentrated. After triturating in an ether/hexane (1/1; v/v) mixture, the expected product is obtained in the form of a white solid.

m = 100 mg m.p. = 179°–181° C. 0.75 ppm: t: 3 H: CH$_3$(nBu) 1.2 ppm: sext: 2 H: CH$_3$—CH$_2$—CH$_2$—CH$_2$— 1.45 ppm: quint: 2 H: CH$_3$—CH$_2$—CH$_2$—CH$_2$— 1.6–1.9 ppm: m: 8 H: cyclopentane 2.3 ppm: t: 2 H: CH$_3$—CH$_2$—CH$_2$—CH$_2$— 4.65 ppm: s: 2 H: —N—CH$_2$—C$_6$H$_4$— 7-7.4 ppm: m: 10 H: aromatic+OH 14.8 ppm: s: 1 H: NH (tetrazole).

EXAMPLE 32

2-[4-((2-n-Butyl-5-oxo-4-spirocyclopentane-2-imidazolin-1-yl)methyl)phenoxy]-2-phenylacetic acid.

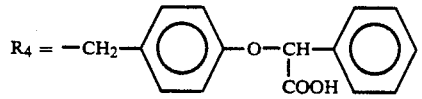

A) Ethyl ester of 2-bromophenylacetic acid.

34.5 g of ethyl ester of phenylacetic acid are dissolved in 150 ml of carbon tetrachloride; 37.5 g of NBS and 38 mg of benzoyl peroxide are added and then the mixture is heated at reflux for 6 hours. After cooling, the mixture is filtered and then the filtrate is concentrated to dryness and distilled under reduced pressure. 43 g of the expected product are obtained.

b.p. = 78°–80° C. at 0.1 mm of Hg.

B) Ethyl ester of 2-(para-tolyloxy)-2-phenylacetic acid.

14.5 g of a 35% suspension of potassium hydride in oil are used and 150 ml of DMF are added under argon. 10.8 g of para-cresol in 100 ml of DMF and 2.7 g of crown ether (18-Crown-6) are added. After stirring for 45 minutes, 24.3 g of ester prepared in the preceding stage are added in 50 ml of DMF and stirring is maintained for 4 hours at RT. The mixture is concentrated, is then extracted with ethyl acetate and washed with water. The expected product is obtained by chromatography on silica by eluting with a heptane/AcOEt (95/5; v/v) mixture.

m = 10.5 g.

C) Ethyl ester of 2-(4-(bromomethyl)phenoxy)-2-phenylacetic acid.

5.38 g of the compound prepared in the preceding stage and 3.18 g of NBS are introduced into 216 ml of carbon tetrachloride; 1 g of azobisisobutyronitrile is added and the mixture is brought to reflux for 4 and a half hours. It is cooled, the reaction mixture is filtered and then the filtrate is concentrated. The expected product is obtained by chromatography on silica by eluting with a heptane/AcOEt (95/5; v/v) mixture.

m = 2.15 g.

D) Ethyl ester of 2-[4-((2-n-butyl-5-oxo-4-spirocyclopentane-2-imidazolin-1-yl)methyl)phenoxy]-2-phenylacetic acid.

462 mg of the hydrochloride of 2-n-butyl-4-spirocyclopentane-2-imidazolin-5-one and 150 mg of an 80% suspension of sodium hydride in oil are mixed under argon in 10 ml of DMF. After stirring for 30 minutes, 944 mg of the compound prepared in the preceding stage are added in 10 ml of DMF and the mixture is left stirring for 4 hours at RT. The reaction mixture is concentrated to dryness, then extracted with AcOEt and the organic phase is washed with water and then with a saturated solution of sodium chloride. After concentrating, the residue is chromatographed on silica by eluting with a DCM/MeOH (95.5/0.5; v/v) mixture.

m = 660 mg.

E) 2-[4-((2-n-Butyl-5-oxo-4-spirocyclopentane-2-imidayl)methyl)phenoxy]-2-phenylacetic acid.

The compound prepared in the preceding stage (650 mg) is dissolved in 12 ml of sodium hydroxide and the solution is poured into 3 ml of water. After stirring for 3 hours at RT, the mixture is concentrated to dryness, taken up with water and then acidified towards pH 3 by the addition of a 3% strength aqueous solution of potassium hydrogen sulphate. The mixture is extracted with AcOEt and is then washed with water. After concentrating, the residue is chromatographed on silica by eluting with a DCM/MeOH (9/1; v/v) mixture.

m = 110 mg.
m.p. = 133° C.

NMR: 0.7 ppm: t: 3 H: $CH_3(nBu)$, 1-2 ppm: m: 12 H: $CH_2$—$CH_2$—$CH_2$—$CH_3$+cyclopentane, 2.2 ppm: t: 2 H: $CH_2$—$CH_2$—$CH_2$—$CH_3$, 4.5 ppm: s: 2 H: —N—$CH_2$—$C_6H_4$—, 5.3 ppm: s: 1 H: —OCH—, 6.6–7.6 ppm: m: 9 H: aromatic

EXAMPLE 33

2-(2-Chlorophenyl)-2-[4-((2-n-butyl-5-oxo-4-spirocyclopentane-2-imidazolin-1-yl)methyl)phenoxy]acetic acid.

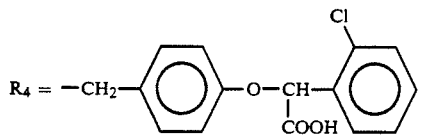

This compound is prepared according to the procedure described in Example 32, by using, as starting product, the ethyl ester of (2-chlorophenyl)acetic acid.

NMR: 0.7 ppm: t: 3 H: $CH_3(nBu)$, 1-2 ppm: m: 12 H: $CH_2$—$CH_2$—$CH_2$—$CH_3$+cyclopentane, 2.25 ppm: t: 2 H: $CH_2$—$CH_2$—$CH_2$—$CH_3$, 4.6 ppm: s: 2 H: —N—$CH_2$—$C_6H_4$—, 6 ppm: s: 1 H: —O—CH—, 7 ppm: AA'-BB' system: 4 H: aromatic, 7.2–7.7 ppm: m: 4 H: aromatic

EXAMPLE 34

Ethyl ester of 3-[4-((2-n-butyl-5-oxo-4-spirocyclopentane-2-imidazolin-1-yl)methyl)phenyl]-2-ethoxycarbonylcinnamic acid.

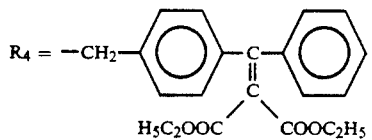

A) Ethyl -3-(para-tolyl)-2-ethoxycarbonyl-cinnamate.

A solution containing 2.5 ml of titanium tetrachloride, 13 ml of carbon tetrachloride and 20 ml of anhydrous THF is prepared at 0° C. After 20 minutes, the following mixture is slowly added: 1.6 ml of pyridine, 1.48 g of ethyl malonate and 1.07 g of 4-methylbenzophenone in 10 ml of THF. After 24 hours at RT, the reaction mixture is filtered and is extracted with AcOEt; the organic phase is washed with a saturated solution of sodium bicarbonate and then with a normal solution of hydrochloric acid; it is dried over sodium sulphate and evaporated and then the residue is chromatographed on silica by eluting with a hexane/ether (5/1; v/v) mixture. 1.28 g of the expected product are obtained.

B) Ethyl-3-[(4-bromomethyl)phenyl]-2-ethoxycarbonylcinnamate.

1 g of the product prepared in the preceding stage is suspended in 20 ml of carbon tetrachloride; 0.578 g of NBS and 30 mg of azobisisobutyronitrile are added. After 2 hours at reflux under UV irradiation, the mixture is evaporated to dryness until the expected product is obtained in solid form.

C) Ethyl ester of 3-[4-((2-n-butyl-5-oxo-4-spirocyclopentane-2-imidazolin-1-yl)methyl)phenyl]-2-ethoxycarbonyl-cinnamic acid.

This product is obtained by proceeding according to the usual methods.

NMR: 0.9–1 ppm: m: 9 H: $2CH_3(CO_2Et)+CH_3(nBu)$, 1.2–1.4 ppm: m: 2 H: $CH_2(nBu)$, 1.4–1.6 ppm: m: 2 H: $CH_2(nBu)$, 1.7–1.9 ppm: m: 8 H: cyclopentane, 2.2 ppm: m: 2 H: $CH_2(nBu)$, 4–4.1 ppm: m: 4 H: $2CH_2(CO_2Et)$, 4.8 ppm: s: 2 H: —N—$CH_2$—$C_6H_4$—, 7.1–7.5 ppm: m: 9 H: aromatic

EXAMPLE 35

3-[4-((2-n-Butyl-5-oxo-4-spirocyclopentane-2-imidazolin-1-yl)methyl)phenyl]-2-carboxy-cinnamic acid.

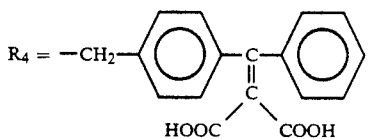

106 mg of the compound prepared in the preceding example are suspended in 3 ml of benzene and 90 mg of anhydrous potassium hydroxide, as a fine powder, and 32 mg of crown ether (18-Crown-6) are added. The mixture is left stirring for 18 hours at RT, protected from moisture. 5 ml of benzene are added and the mixture is acidified by the addition of N hydrochloric acid. The gum formed is taken up with hexane and 60 mg of the expected product are obtained in the form of a powder.

m.p. = 135°–140° C.

NMR: 0.8 ppm: m: 3 H: $CH_3(nBu)$, 1.1–1.6 ppm: m: 4 H: $2CH_2(nBu)$, 1-8 ppm: m: 8 H: cyclopentane, 2.3 ppm: m: 2 H: $CH_2(nBu)$, 4.7 ppm: s: 2 H: —N—$CH_2$—$C_6H_4$—, 7–7.4 ppm: m: 9 H: aromatic, 12.5–13.3 ppm: m: 2 H: 2COOH

EXAMPLE 36

2-n-Butyl-1-[4-(1-phenyl-2,2-(di-5-tetrazolyl)-vinyl)benzyl]-4-spirocyclopentane-2-imidazolin-5-one hydrochloride.

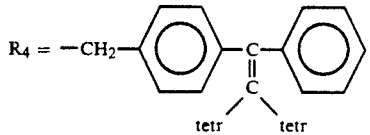

A) (para-tolyl)phenylketimine hydrochloride.

A mixture containing 13.2 g of 4-methylbenzophenone, 125 ml of liquid ammonia and 3.96 g of ammonium chloride in 60 ml of THF are brought to 120° C. for 15 hours in a sealed tube. The ammonia is driven off and then 80 ml of ether and 40 ml of water are added.

After separating, the material is extracted with ether, dried and evaporated. The expected product is obtained in solid form.

B) α, α-dicyano-β-(para-tolyl)-styrene.

10 g of the compound prepared in the preceding stage are placed in 100 ml of ethanol and 5.45 ml of N-ethylmorpholine and 2.85 g of malononitrile are added. After 5 hours at RT, the mixture is concentrated by half, the insoluble material is filtered off and the filtrate is washed with ether. The crude product obtained is taken up with chloroform; the mixture is filtered, the solvents are evaporated and 7.1 g of the expected product are obtained.

C) α,α-dicyano-β-[4-(bromomethyl)phenyl]-styrene.

6 g of the compound prepared in the preceding stage are placed in 100 ml of carbon tetrachloride and 4.82 g of NBS and 250 mg of azobisisobutyronitrile are added; the mixture is brought to reflux and then under UV irradiation for 10 minutes. The reaction mixture is then evaporated to dryness to allow the expected product to be obtained in the form of an oil.

D) 2-n-Butyl-1-[4-(2,2-dicyano-1-phenyl-vinyl)-benzyl]-4-spirocyclopentane-2-imidazolin-5-one.

This compound is prepared by the usual method.

NMR: 0.6-0.7 ppm: m: 3 H: $CH_3(nBu)$, 1.1-1.4 ppm: m: 4 H: $CH_2$—$CH_2$—$CH_2$—$CH_3$. 1.6-1.9 ppm: m: 8 H: cyclopentane, 2.2-2.4 ppm: m: 2 H: $CH_2$—$CH_2$—$CH_2$—$CH_3$—, 4.7 ppm: s: 2 H: —N—$CH_2$—$C_6H_4$—, 7.1-8.1 ppm: m: 9 H: aromatic E) 2-n-butyl-1-[4-(1-phenyl-2,2-(di-5-tetrazolyl)-vinyl)benzyl]-4-spirocyclopentane-2-imidazolin-5-one hydrochloride.

The conversion of the cyano groups to tetrazolyl, to thus obtain the expected product, is carried out according to the usual method.

NMR: 0.8-0.9 ppm: m: 3 H: $CH_3(nBu)$, 1.2-1.6 ppm: m: 6 H: $CH_2$—$CH_2$—$CH_2$—$CH_3$, 1.8-2.2 ppm: m: 8 H: cyclopentane 2.8 ppm: m: 2 H: $CH_2$—$CH_2$—$CH_2$—$CH_3$, 4.95 ppm: s: 2 H: —N—$CH_2$—$C_6H_4$—, 6.9-7.4 ppm: m: 9 H: aromatic

EXAMPLE 37

4-[(2-n-Butyl-5-oxo-4-spirocyclopentane-2-imidazol-1-yl)methyl]benzoic acid.

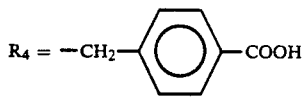

A) tert-butoxide of 4-methylbenzoic acid.

26.2 g of para-tolyl chloride in 500 ml of THF are cooled to 15° C. and treated with stirring with 22.4 g of potassium tert-butoxide powder, added in small portions, while maintaining the temperature at 15°-20° C. with an ice bath. The mixture is left stirring at RT for 1 hour, then the mixture is concentrated by half and then diluted with 500 ml of water. It is extracted with ether, the ether phases are washed with a saturated solution of sodium hydrogen carbonate, and with a saturated solution of sodium chloride, then dried over sodium sulphate and concentrated. 32 g of the expected product are obtained in the form of an oil.

B) tert-Butoxide of 4-[(2-n-butyl-5-oxo-4-spirocyclopentane-2-imidazol-1-yl)methyl]benzoic acid.

The procedure is carried out in 2 stages according to the usual methods.

C) 4-[(2-n-Butyl-5-oxo-4-spirocyclopentane-2-imidazol-1-yl)methyl]benzoic acid.

1.5 g of the tert-butyl ester previously obtained is treated with TFA by following Example 2, stage D). The oil obtained is treated with water and then brought to pH 6 by the addition of sodium hydrogen carbonate. It is extracted with ethyl acetate, washed with a solution of sodium chloride, dried over sodium sulphate and evaporated to dryness.

m=0.9 g.
m.p.=144°-148° C.

EXAMPLE 38

1-[(4-Benzoyl)benzyl]-2-n-butyl-4-spirocyclopentane-2-imidazolin-5-one.

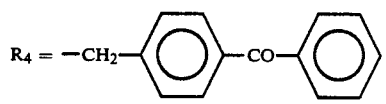

This compound is prepared by the usual methods. 4-(Bromomethyl)benzophenone is prepared from 4-methylbenzophenone (commercially available) and then this product is added to the hydrochloride of 2-n-butyl-4-spirocyclopentane-2-imidazolin-5-one.

m.p.=99°-101° C.

EXAMPLE 39

1-[4-(α-Acetoxybenzyl)benzyl]-2-n-butyl-4-spirocyclopentane -2-imidazolin-5-one.

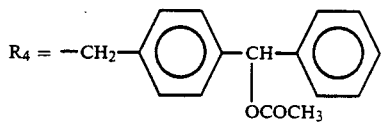

The acetate of (4-methyl)diphenylmethane is prepared from 4-methylbenzhydrol (commercially available) and then the compound according to the invention is prepared by following the usual procedures.

NMR: 0.65 ppm: m: 3 H: $CH_3(nBu)$, 1.1 ppm: sext: 2 H: $CH_3$—$CH_2$—$CH_2$—$CH_2$—, 1.35 ppm: quint: 2 H: $CH_3$—$CH_2$—$CH_2$—$CH_2$—, 1.4-1.5 ppm: m: 8 H: cyclopentane, 2.05 ppm: s: 3 H: $OCOCH_3$, 2.2 ppm: t: 2 H: $CH_3$—$CH_2$—$CH_2$—$CH_2$—, 4.55 ppm: s: 2 H: —N—$CH_2$—$C_6H_4$—, 6.65 ppm: s: 1 H: —$C_6H_4$—$CH$—$C_6H_5$, 7-7.4 ppm: m: 9 H: aromatic

EXAMPLE 40

2,2-Difluoro-para-[(2-n-butyl-5-oxo-4-spirocyclopentane-2-imidazolin-1-yl)methyl]phenylacetic acid.

A) Ethyl ester of 2,2-difluoro-2-(para-tolyl)acetic acid.

The ethyl ester of 2-oxo-2-(para-tolyl)acetic acid is prepared according to R. C. Cousins in J. Org. Chem., 1980, 45, 2976-2983. 8 ml of diethylaminosulphur trifluoride are added dropwise to 2.88 g of this ester and the mixture is left stirring overnight at RT. The mixture is diluted with ice, then extracted with ethyl acetate and the organic phase is washed with a saturated solution of NaHCO₃, a solution of KHSO₄—K₂SO₄, water and then a saturated solution of NaCl.

B) Ethyl ester of 2,2-difluoro-para-[(2-n-butyl-5-oxo-4-spirocyclopentane-2-imidazolin-1-yl)methyl]phenylacetic acid.

This compound is prepared according to the usual methods by the addition of the ethyl ester of 2-(4-(bromomethyl)phenyl)-2,2-difluoroacetic acid to 2-n-butyl-4-spirocyclopentane-2-imidazolin-5-one.

C) 2,2-Difluoro-para-[(2-n-butyl-5-oxo-4-spirocyclopentane-2-imidazolin-1-yl)methyl]phenylacetic acid.

500 mg of the ester prepared in the preceding stage are placed in 2 ml of methanol and 2 ml of dioxane in the presence of 1.3 ml of N sodium hydroxide. After 1 and a half hours, the mixture is diluted with AcOEt and acidified to pH 4 by the addition of N hydrochloric acid. After evaporating, the mixture is taken up with ether. The solid obtained is filtered off, then washed with water and a saturated solution of NaCl.

m = 220 mg
m.p. = 194°–198° C.

EXAMPLE 41

N-Hydroxy-2-[4-((2-n-butyl-5-oxo-4-spirocyclopentane-2-imidazolin-1-yl)methyl)phenyl]-2-phenylacetamide.

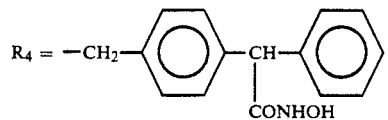

589 mg of the acid prepared in Example 1 are placed in 20 ml of chloroform and treated at 0° C. with 1.2 ml of thionyl chloride. After 1 hour at RT, the reaction mixture is concentrated and the traces of thionyl chloride are removed by coevaporation with toluene. The acid chloride formed is taken up with 10 ml of DCM and added dropwise at 0° C. to a solution containing 250 mg of hydroxylamine hydrochloride and 917 μl of DIPEA in 10 ml of DMF. After 1 hour at RT, the solution is concentrated, taken up with DCM and then washed with water, dried and concentrated. The residue is chromatographed on silica by eluting with a toluene-methanol (9/1; v/v) mixture. The pure fractions are combined and concentrated and the residue is recrystallised from an ether/hexane mixture.

m = 400 mg.
MH⁺: 434
m.p. 90° C. with decomposition.

NMR: 0.7 ppm: t: 3 H: CH₃(nBu), 1.15 ppm: sext: 2 H: CH₃—CH₂—CH₂—CH₂—, 1.4 ppm: quint: 2 H: CH₃—CH₂—CH₂—CH₂—, 1.5–1.8 ppm: m: 8 H: cyclopentane, 2.2 ppm: t: 2 H: CH₃—CH₂—CH₂—CH₂—, 4.55 ppm: s: 2 H: —N—CH₂—C₆H₄—, 4.6 ppm: s: 1 H: —C₆H₄—CH—C₆H₅, 6.95–7.3 ppm: m: 9 H: aromatic

EXAMPLE 42

2-[4-((2-n-Butyl-5-oxo-4-spirocyclopentane-2-imidazolin-1-yl)methyl)phenyl]-2-hydroxy-2-phenylacetic acid.

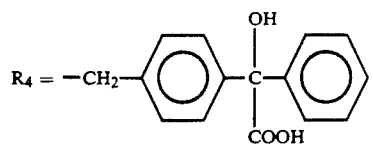

A) 2-(para-Tolyl)-2-hydroxyphenylacetic acid.

This compound is prepared according to A. McKenzie, J. Chem. Soc., 1934, 1070–1075.

B) Methyl ester of 2-(para-tolyl)-2-hydroxy-2-phenylacetic acid.

5 g of the compound prepared in stage A, dissolved in 150 ml of methanol, are brought to reflux overnight in the presence of 7.5 ml of concentrated sulphuric acid. The solution is adjusted to pH 6–7 by the addition of concentrated aqueous sodium hydroxide and is then extracted with ethyl acetate. The organic phase is washed with water and then with a concentrated solution of sodium chloride. It is dried over sodium sulphate and then concentrated. The residue is chromatographed on silica by eluting with a cyclohexane/AcOEt (95/5; v/v) mixture. 2 products are isolated which are identified by NMR and IR: the methyl ester of 2-(para-tolyl)-2-methoxyphenylacetic acid and the methyl ester of 2-(para-tolyl)-2-hydroxyphenylacetic acid.

C) Methyl ester of 2-(para-bromomethyl)phenyl-2-hydroxy-2-phenylacetic acid.

This compound is prepared by the usual method from the methyl ester of 2-(para-tolyl)-2-hydroxyphenylacetic acid obtained in the preceding stage.

D) Methyl ester of 2-[4-((2-n-butyl-5-oxo-4-spirocyclopentane-2-imidazolin-1-yl)methyl)phenyl]-2-hydroxy-2-phenylacetic acid.

This product is obtained by the usual method by the addition of the product prepared in stage C to the hydrochloride of 2-n-butyl-4-spirocyclopentane-2-imidazolin-5-one.

E) 2-[4-((2-n-Butyl-5-oxo-4-spirocyclopentane-2-imidazolin-1-yl)methyl)phenyl]-2-hydroxy-2-phenylacetic acid.

1.37 g of the compound prepared in stage D are dissolved in 15 ml of methanol and 4 ml of N sodium hydroxide are added. After stirring for 2 hours and 15 minutes at RT, the mixture is diluted with water and ethyl acetate and is adjusted to pH 4 by the addition of N hydrochloric acid. The organic phase is separated off, washed with water and then with an aqueous solution of sodium chloride; it is dried and concentrated.

m.p. = 98° C.

NMR: 7.00–7.4 ppm: m: 9 H: aromatic, 4.65 ppm: s: 2 H: —N—CH₂—C₆H₄, 2.3 ppm: t: 2 H: CH₃—CH₂—CH₂—CH₂, 1.6–1.9 ppm: m: 8 H: cyclopentane, 1.47 ppm: quint: 2 H: CH₃—CH₂—CH₂—CH₂—, 1.25 ppm: sext: 2 H: CH₃—CH₂—CH₂—CH₂—, 0.75 ppm: t: 3 H: CH₃—CH₂—CH₂—CH₂—

EXAMPLE 43

2-Acetoxy-2-[4-((2-n-butyl-5-oxo-4-spirocyclopentane-2-imidazolin-1-yl)methyl)phenyl]-2-phenylacetic acid.

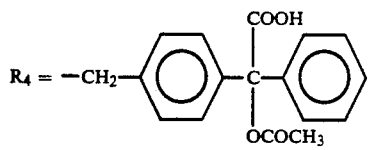

200 mg of the compound prepared in the preceding example are diluted in 5 ml of DMF and 33 mg of sodium hydride are added, in small quantities, under nitrogen: the mixture is left stirring for 20 minutes at RT and 54 mg of acetyl chloride in 5 ml of DMF are slowly added. After stirring for 3 hours, the reaction mixture is diluted with water and ethyl acetate and is adjusted to pH 4 by a solution of $K_2SO_4$—$KHSO_4$. It is extracted with ethyl acetate, the organic phase is washed with water and then with a saturated solution of sodium chloride; it is dried over sodium sulphate and concentrated. The residue is taken up with ether; the precipitate formed is filtered off then dried under vacuum.

m = 217 mg.
m.p. = 147° C.
NMR: 7.1-7.6 ppm: m: 9 H: aromatic, 4.7 ppm: s: 2 H: —N—$CH_2$—$C_6H_4$—, 2.35 ppm: t: 2 H: $CH_3$—$CH_2$—$CH_2$—$CH_2$—, 2.20 ppm: s: 3 H: CO—$CH_3$, 1.65-2 ppm: m: 8 H: cyclopentane, 1.5 ppm: quint: 2 H: $CH_3$—$CH_2$—$CH_2$—$CH_2$—, 1.3 ppm: sext: 2 H: $CH_3$—$CH_2$—$CH_2$—$CH_2$—, 0.8 ppm: t: 3 H: $CH_3$—$CH_2$—$CH_2$—$CH_2$—,

EXAMPLE 44

2-[4-((2-n-Butyl-5-oxo-4-spirocyclopentane-2-imidazolin-1-yl)methyl)phenyl]-2-methoxy-2-phenylacetic acid.

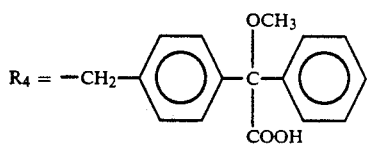

A) Methyl ester of 2-(para-bromomethyl)phenyl-2-methoxy-2-phenylacetic acid.

This compound is prepared by the usual method from the 2-(para-tolyl)-2-methoxyphenylacetic acid obtained in Example 42, stage B.

B) Methyl ester of 2-[4-((2-n-butyl-5-oxo-4-spirocyclopentane-2-imidazolin-1-yl)methyl)phenyl]-2-methoxy-2-phenylacetic acid.

This compound is obtained by the usual method by combining the compound prepared in the preceding stage and the hydrochloride of 2-n-butyl-4-spirocyclopentane-2-imidazolin-5-one.

C) 2-[4-((2-n-Butyl-5-oxo-4-spirocyclopentane-2-imidazolin-1-yl)methyl)phenyl]-2-methoxy-2-phenylacetic acid.

1.92 g of the compound prepared in the preceding stage are dissolved in 20 ml of methanol and 5.2 ml of 1N sodium hydroxide are added. After 4 hours at reflux, the reaction mixture is diluted with ethyl acetate and water and is then adjusted to pH 4 by the addition of N hydrochloric acid. The organic phase is separated off, washed with water, with a saturated solution of sodium chloride, then dried over sodium sulphate and concentrated. The residue is chromatographed on silica by eluting with a DCM/MeOH/AcOH (92/5/3; v/v/v) mixture. The expected product is obtained.

m = 1.014 g.
m.p. = 67° C.
NMR: 7.5 ppm: m: 9 H: aromatic, 4.75 ppm: s: 2 H: —N—$CH_2$—$C_6H_4$—, 3.15 ppm: s: 3 H: O—$CHH_3$, 2.4 ppm: t: 2 H: $CH_3$—$CH_2$—$CH_2$—$CH_2$—, 1.7-2 ppm: m: 8 H: cyclopentane, 1.5 ppm: quint: 2 H: $CH_3$—$CH_2$—$CH_2$—$CH_2$—, 1.3 ppm: sext: 2 H: $CH_3$—$CH_2$—$CH_2$—$CH_2$—, 0.8 ppm: t: 3 H: $CH_3$—$CH_2$—$CH_2$—$CH_2$—

EXAMPLE 45

2-Cyano-2-[4-((2-n-butyl-5-oxo-4-spirocyclopentane-2-imidazolin-1-yl)methyl)phenyl]phenylacetonitrile.

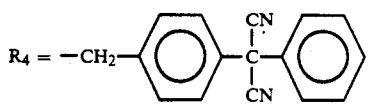

A) Phenyl-(para-tolyl)malononitrile.

A mixture of 14.7 g of 4-methylbenzophenone and 16.4 g of phosphorus pentachloride are heated for 2 hours at 120° C. The mixture is evaporated to dryness, the residual oil is then dissolved in 200 ml of DCM and 19.3 g of trimethylsilyl cyanide and 2.1 ml of tin tetrachloride are added under nitrogen. After stirring for 48 hours at RT, the reaction mixture is poured into a water-ice mixture; it is filtered and extracted 3 times with methylene chloride. The organic phases are washed with a solution of sodium bicarbonate, dried and then evaporated. The residue is chromatographed on silica with a hexane/acetone (5/1; v/v) mixture.

m = 9.8 g.

B) 2-Cyano-2-[4-((2-n-butyl-5-oxo-4-spirocyclopentane-2-imidazolin-1-yl)methyl)phenyl]phenylacetonitrile.

The preparation of the expected product, which is purified on silica by eluting with a toluene/AcOEt (3/1; v/v) mixture, is carried out in 2 stages according to the usual process.

NMR: 0.8 ppm: t: 3 H: $CH_3$(nBu), 1.2-1.4 ppm: m: 2 H: $CH_2$(nBu), 1.4-1.6 ppm: m: 2 H: $CH_2$(nBu), 1.7-2 ppm: m: 8 H: cyclopentane, 2.3-2.4 ppm: m: 2 H: $CH_2$(nBu), 4.8 ppm: s: 2 H: —N—$CH_2$—$C_6H_4$, 7.35-7.45 and 7.6-7.7 ppm: m: 9 H: aromatic
IR (DCM) 2200 $cm^{-1}$ (CN)

EXAMPLE 46

2-[4-(4-((2-n-butyl-5-oxo-4-spirocyclopentane-2-imidazolin-1-yl)methyl)phenyl)benzoyl]benzoic acid trifluoroacetate.

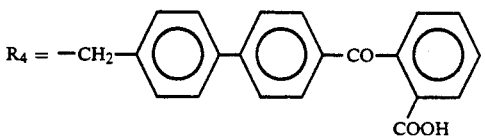

A) 2-[4-(para-Tolyl)benzoyl]benzoic acid.

A solution containing 9 g of 4-methylbiphenyl and 7.5 g of phthalic anhydride in 50 ml of orthodichlorobenzene is prepared and 13.5 g of aluminium trichloride are added. After stirring overnight at 100° C., the reaction mixture is poured onto 500 ml of water and ice and 100 ml of concentrated hydrochloric acid. The organic phase is separated off and diluted with hexane. The solid formed is dissolved in an 8% strength aqueous ammonia solution which is then washed with ether and is acidified with concentrated hydrochloric acid in the presence of ice. The solid formed is filtered off, washed with water, dried at 60° C. under vacuum and is then finely powdered in ether, filtered off and dried.

m = 5.8 g.
m.p. = 260° C.

B) tert-Butoxide of 2-[4-(para-tolyl)benzoyl]benzoic acid.

5 g of the acid prepared in the preceding stage are suspended in 30 ml of thionyl chloride, left stirring for 20 hours at RT and then heated for 6 hours at 50° C. The solution obtained is evaporated to dryness, the residue is dissolved in toluene and then evaporated; the operation is carried out once again in toluene at 80° C. The residue is dissolved in 30 ml of THF, cooled in an ice bath and treated while stirring vigorously with 1.35 g of potassium tert-butoxide added progressively so as to maintain the temperature at 15°-20° C. After stirring for 1 hour at RT, the mixture is poured onto water, extracted with ether and washed with an aqueous salt solution; the organic phases are dried over sodium sulphate and evaporated to dryness.

m = 3.4 g

C) 2-[4-(4-((2-n-butyl-5-oxo-4-spirocyclopentane-2-imidazolin-1-yl)methyl)phenyl)benzoyl]benzoic acid trifluoroacetate.

The preparation of the expected product is then carried out according to the usual methods.

m.p. = 77°-85° C.

EXAMPLE 47

2-[4-((2-n-Butyl-5-oxo-4-spirocyclopentane-2-imidazolin-1-yl)methyl)-2-n-propylphenoxy]phenylacetic acid.

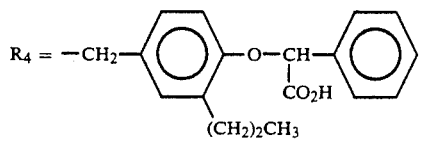

A) Ethyl ester of 2-[4-bromomethyl-2-n-propylphenoxy]-phenylacetic acid.

This ester is prepared by following the procedure described in International Patent Application WO 91/12001.

B) Ethyl ester of 2-[4-((2-n-butyl-5-oxo-4-spirocyclopentane-2-imidazolin-1-yl)methyl)-2-n-propylphenoxy]-phenylacetic acid.

This ester is prepared by following the usual method and is purified by chromatography on silica by eluting with a DCM/AcOEt (9/1; v/v) mixture.

C) 2-[4-((2-n-Butyl-5-oxo-4-spirocyclopentane-2-imidazolin-1-yl)methyl)-2-n-propylphenoxy]phenylacetic acid.

80 mg of the compound obtained in the preceding stage are stirred for 2 hours at RT in the presence of 4 ml of methanol, 1 ml of water and 15 mg of sodium hydroxide. After evaporating the solvents, the mixture is taken up with a water/ether mixture, the aqueous phase is then acidified to a pH of 5 and is then extracted with ethyl acetate. The product obtained is washed with a saturated solution of sodium chloride and then purified in heptane.

NMR: 0.6-2.1 ppm: m: 20 H: —CH$_2$—CH$_2$—CH$_3$ (propyl), —CH$_2$—CH$_2$—CH$_2$—CH$_3$+cyclopentane 2.4 ppm: t: 2 H: —CH$_2$—CH$_2$—CH$_2$—CH$_3$, 2.7 ppm: t: 2 H: —CH$_2$—CH$_2$—CH$_3$ (propyl), 4.4 ppm: s: 2 H: —N—C$\underline{H}_2$—C$_6$H$_3$, 5.9 ppm: s: 1 H: —OC$\underline{H}_3$—, 6.7-7.8 ppm: m: 8 H: aromatic

EXAMPLE 48

4-[4'-((2-n-Butyl-5-oxo-4-spirocyclopentane-2-imidazolin-1-yl)methyl)-4-biphenylyl]-4-oxobutyric acid

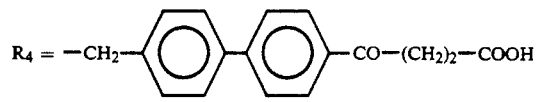

A) 4-(4'-Methyl-4-biphenylyl)-4-oxobutyric acid.

This compound is prepared according to the methods described by E. Burker in Bull. Soc. Chim. Fr., 1888, 449 and Weizmann et al. in Chem. Ind., 1940, 402.

6.5 g of anhydrous aluminium chloride are suspended in 50 ml of dichloroethane. 3.2 g of succinic anhydride and 4.5 g of 4-methylbiphenyl are added. After stirring for 24 hours at RT, the reaction mixture is poured onto 400 ml of a water/ice mixture containing 50 ml of concentrated HCl. The solid formed is filtered off, washed with water and dried at 60° C. under vacuum.

m = 6.5 g.
m.p. = 188° C.

B) Methyl ester of 4-(4'-methyl-4-biphenylyl)-4-oxobutyric acid.

2.85 g of the acid prepared above are dissolved in 30 ml of DMF and stirred for 20 minutes at RT with 3.63 g of caesium carbonate, then for 3 hours at RT with 2.4 ml of methyl iodide. The methyl iodide excess is evaporated under vacuum and then the reaction mixture is poured onto 100 g of a water/ice mixture. The solid formed is filtered off, dissolved in AcOEt, treated with active charcoal, dried over sodium sulphate and evaporated to dryness. m = 1.9 g.

C) Methyl ester of 4-(4'-bromomethyl-4-biphenylyl)-4-oxobutyric acid.

This compound is prepared according to the usual methods.

D) Methyl ester of 4-[4'-((2-n-butyl-5-oxo-4-spirocyclopentane-2-imidazolin-1-yl)methyl)-4-biphenylyl]-4-oxobutyric acid.

This compound is prepared according to the usual methods.

E) 4-[4'-((2-n-Butyl-5-oxo-4-spirocyclopentane-2-imidazolin-1-yl)methyl)-4-biphenylyl]-4-oxobutyric acid.

900 mg of the ester prepared above are dissolved in 7.5 ml of methanol, 1.5 ml of potassium hydroxide and 1 ml of water. After stirring for 1 hour and 40 minutes ar RT, the reaction mixture is diluted with 25 ml of water, washed twice with AcOEt and neutralised with 4.8 ml of N HCl. The precipitate formed is extracted with AcOEt, the insoluble material is then filtered off, the filtrate is dried over sodium sulphate and the solvent is evaporated. The solid residue is taken up in ether, filtered off and dried.

m = 580 mg.
m.p. = 167° C.

EXAMPLE 49

2-n-Butyl-4-spirocyclopentane-1-[4-(N-(5-tetrazolyl) anilino)benzyl]-2-imidazolin-5-one.

A) N-Phenyl-N-(para-tolyl)urea.

This compound is prepared according to J. R. Robinson in Can. J. Chem., 1954, 32, 901-905. 2.92 g of N-(para-tolyl)aniline described in Example 8, stage A) are dissolved in 30 ml of acetic acid; 1.6 g of potassium isocyanate are added every 24 hours for 3 days. Sodium hydroxide solution, to reach a pH of 5, and 200 ml of water are then added. After cooling, the solid obtained is filtered off, washed with water and dried over phosphoric anhydride.

m=3.4 g.

m.p.=141°-145° C.

B) N-Cyano-N-(para-tolyl)aniline.

This compound is prepared according to the method described by J. R. Robinson (loc. cit.).

3.33 g of the compound prepared previously are dissolved in 22 ml of pyridine and treated with 8.4 g of tosyl chloride at 100° C. After 1 hour, the reaction mixture is poured into water. The mixture is extracted with AcOEt, then washed with a KHSO$_4$—K$_2$SO$_4$ solution, with a saturated solution of NaCl, with a saturated solution of NaHCO$_3$ and a saturated solution of NaCl and is then dried. The residue is chromatographed on silica by eluting with a hexane/DCM (5/5; v/v) mixture. 2.2 g of an oil which crystallises in the refrigerator are obtained.

m.p.=36°-37° C.

C) N-Cyano-N-(4-(bromomethyl)phenyl)aniline.

This compound is prepared according to the usual methods.

D) 2-n-Butyl-4-spirocyclopentane-1-[4-(N-cyanoanilino) benzyl]-2-imidazolin-5-one.

This compound is prepared according to the usual methods. m.p.=75°-78° C.

E) 2-n-Butyl-4-spirocyclopentane-1-[4-(N-(5-tetrazolyl) anilino)benzyl]-2-imidazolin-5-one.

The cyano group of the compound obtained in the preceding stage is converted, according to the usual methods, to the tetrazolyl group.

m.p.=175°-178° C.

NMR: 0.85 ppm: t 3 H: CH$_3$(nBu), 1.3 ppm: sext: 2 H: CH$_3$—CH$_2$—CH$_2$—CH$_2$—, 1.5 ppm: quint: 2 H: CH$_3$—CH$_2$—CH$_2$—CH$_2$—, 1.6-2 ppm: m: 8 H: cyclopentane, 2.4 ppm: t: 2 H: CH$_3$—CH$_2$—CH$_2$—CH$_2$—, 4.7 ppm: s: 2 H: N—CH$_2$—C$_6$H$_4$—, 7.2-7.5 ppm: m: 9 H: aromatic

EXAMPLE 50

N-Phenyl-N-[4-((2-n-butyl-4-spirocyclopentane-5-oxo-2-imidazolin-1-yl)methyl)phenyl]methoxycarboxamidine.

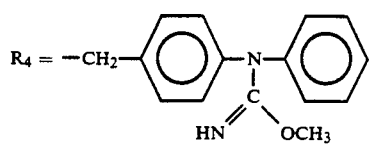

This compound is prepared according to the method described by A. Bonetti and E. Bellora in J. Org. Chem. 1972, 37 (21), 3352.

670 mg of the compound prepared in Example 49, stage D) are dissolved in 10 ml of methanol and heated with 109 mg of potassium cyanide. After 12 hours, the mixture is concentrated and extracted with AcOEt; the organic phase is washed with water and with a concentrated solution of NaCl and is then dried over Na$_2$SO$_4$.

m=670 mg.

NMR: 0.8 ppm: t: 3 H: CH$_3$(nBu), 1.25 ppm: sext: 2 H: CH$_3$—CH$_2$—CH$_2$—CH$_2$—, 1.5 ppm: quint: 2 H: CH$_3$—CH$_2$—CH$_2$—CH$_2$—, 1.6-2 ppm: m: 8 H: cyclopentane, 2.4 ppm: t: 2 H: CH$_3$—CH$_2$—CH$_2$—CH$_2$—, 3.7 ppm: s: 3 H: OCH$_3$—, 4.7 ppm: s: 2 H: N—CH$_2$—C$_6$H$_4$—, 5.8 ppm: s: 1 H: —NH, 7.2-7.5 ppm: m: 9 H: aromatic

EXAMPLE 51

2-n-Butyl-4-spirocyclopentane-1-[4-(N-(5-oxo-1,2,4-oxadiazol-3-yl)anilino)-benzyl]2-imidazolin-5-one.

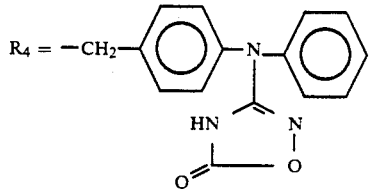

The 5-oxo-1,2,4-oxadiazole is prepared according to M. A. Perez et al., Synthesis, 1983, 483.

A) N'-Acetyl-N-phenyl-N-[4-(2-n-butyl-4-spirocyclopentane-5-oxo-2-imidazolin-1-yl)methyl)phenyl]methoxycarboxamidine.

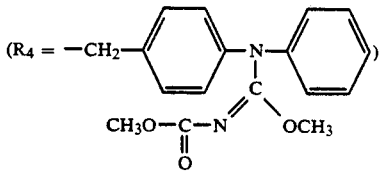

716 mg of the compound prepared in Example 50 are dissolved in 10 ml of DCM and treated at RT with 195 μl of acetyl chloride in the presence of 292 μl of collidine. After 24 hours, the reaction mixture is concentrated and the residue is chromatographed on silica by eluting with a heptane/acetone (75/25; v/v) mixture.

m=500 mg.

B) 2-n-Butyl-4-spirocyclopentane-1-[4-(N-(5-oxo-1,2,4-oxadiazol-3-yl)anilino)-benzyl]-2-imidazolin-5-one.

A solution of 77 mg of hydroxylamine chloride in 5 ml of methanol is treated for 15 minutes with 60 mg of sodium methoxide; 490 mg of the compound obtained in the preceding stage, dissolved in 10 ml of methanol, are then added. After heating overnight at reflux, the mixture is concentrated and then purified by chromatography on silica by eluting with a heptaneacetone/acetic acid (80/20/1) mixture. After triturating in an ether/hexane mixture, a white powder is obtained.

m = 70 mg.

m.p. = 187°-190° C.

NMR: 0.85 ppm: t: 3 H: $CH_3(nBu)$, 1.3 ppm: sext: 2 H: $CH_3$—$CH_2$—$CH_2$—$CH_2$, 1.55 ppm: quint: 2 H: $CH_3$—$\underline{CH_2}$—$CH_2$—$CH_2$—, 2.40 ppm: t: 2 H: $CH_3$—$CH_2$—$\underline{CH_2}$—$CH_2$—, 1.6–2 ppm: m: 8 H: cyclopentane, 4.75 ppm: s: 2 H: —N—$CH_2$—$C_6H_4$—, 7.2–7.5 ppm: m: 9 H: aromatic, 12.2 ppm: s: 1 H: —N$\underline{H}$

EXAMPLE 52

2-[4-((2-n-butyl-4-cyclohexyl-4-methyl-5-oxo-2-imidazolin-1-yl)methyl)phenyl]phenylacetic acid trifluoroacetate.

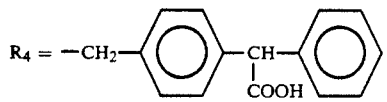

A) 5-Cyclohexyl-5-methylhydantoin.

This compound is prepared according to J. Org. Chem., 1960, 25, 1920–1924.

50 g of cyclohexyl methyl ketone, dissolved in 400 ml of 95 alcohol, are added over 30 minutes to 29.4 g of sodium cyanide and 192 g of ammonium carbonate in 400 ml of water. The mixture is heated at 55°-60° C. for 4 hours, is then evaporated by half under vacuum and is left overnight at +4° C. The precipitate formed is filtered off, washed with water and then dried under vacuum over phosphoric anhydride. 65.5 g of the expected hydantoin are obtained; it is identified from its IR and NMR spectra. m.p. = 220° C.

B) 2-Amino-2-cyclohexylpropionic acid.

This compound is prepared according to J. Org. Chem., 1960, 25, 1920–1924.

A mixture containing 7 g of the hydantoin prepared in the preceding stage and 28 g of barium hydroxide octahydrate in 150 ml of water is brought to 160° C. for 5 hours in a steel tube. The reaction mixture is saturated with solid carbon dioxide; the insoluble material formed is filtered off and then the filtrate is concentrated under vacuum. The solid residue is taken up in acetone, filtered off and dried. 5.25 g of the expected acid are obtained; it is identified from its IR and NMR spectra. The product melts with decomposition at 350° C.

C) Ethyl ester of 2-amino-2-cyclohexylpropionic acid.

3 g of the acid prepared in the preceding stage are added to 40 ml of absolute alcohol saturated with hydrogen chloride gas and the mixture is then heated at reflux, with stirring, for 20 hours. The reaction mixture is evaporated under vacuum and the residue is taken up in an ether/water mixture which is adjusted to pH 9 by the addition of a saturated solution of sodium bicarbonate. The organic phase is separated off, washed with a saturated solution of sodium chloride and then evaporated under vacuum. 2.1 g of the expected ester are obtained in the form of an oil. Identification from IR and NMR spectra.

D) Ethyl valerimidate.

This compound is prepared in the hydrochloride form according to MacElvain (J. Am. Chem. Soc., 1942, 1825–1827). It is released from its hydrochloride by the action of potassium carbonate and is then extracted with DCM.

E) 2-n-Butyl-4-cyclohexyl-4-methyl-2-imidazolin-5-one.

2 g of the ester prepared in stage C) and 2.35 g of ethyl valerimidate are mixed in 6 ml of xylene to which 6 drops of acetic acid are added; the mixture is brought to reflux for 6 hours. The reaction mixture is then concentrated under vacuum and the residue is chromatographed on fine silica gel by eluting with a chloroform/methanol/acetic acid (95/9/3; v/v/v) mixture. The fractions containing the desired product are combined and then evaporated under vacuum; the residue is taken up with an ethyl acetate/water mixture and is adjusted to pH 9 by the addition of a solution of sodium hydroxide. The organic phase is separated off, washed with water and then with a saturated solution of sodium chloride, dried over sodium sulphate and then evaporated to dryness. The expected product is obtained in the form of a thick oil which solidifies to give an amorphous solid.

m = 1.56 g

IR: (chloroform) 1720 cm$^{-1}$ C=O, 1640 cm$^{-1}$ C=N

NMR: 1.13 ppm: s: 3 H: $CH_3$ at position 4 of the imidazolinone.

F) (para-Tolyl)phenylacetic acid.

This acid is prepared from para-tolylaldehyde according to the method quoted by M. E. Grundy et al. in J. Chem. Soc., 1960, 372–376.

G) tert-Butyl ester of 2[(para-bromomethyl)phenyl]phenylacetic acid.

This compound is prepared according to Example 1, stages B and C.

H) tert-Butyl ester of 2-[4-(2-n-butyl-4-cyclohexyl-4-methyl-5-oxo-2-imidazolin-1-yl)methyl)phenyl]phenylacetic acid.

This compound is prepared according to the usual methods.

IR: (chloroform) 1720–1725 cm$^{-1}$ C=O (imidazolinone+ester), 1635 cm$^{-1}$ C=N (imidazolinone)

I) 2-[4-((2-n-butyl-4-cyclohexyl-4-methyl-5-oxo-2-imidazolin-1-yl)methyl)phenyl]phenylacetic acid trifluoroacetate.

The tert-butyl ester obtained in the preceding stage is deprotected with TFA according to the usual method. This product is obtained in the form of a foam. NMR: 7.1–7.45 ppm: m: 9 H: aromatic, 5.1 ppm: s: 1 H: C$\underline{H}CO_2H$, 4.7 ppm: s: 2 H: N—$CH_2$—$C_6H_4$, 2.4 ppm: t: 2 H: $CH_2$—$CH_2$—$CH_2$—$CH_3$, 0.9–1.9 ppm: m: 11 H: cyclohexyl +4 H: $CH_3$—$\underline{CH_2}$—$\underline{CH_2}$—$CH_3$, 1.25 ppm: s: 3 H: $CH_3$ at position 4 of the imidazolinone,

EXAMPLE 53

2-n-Butyl-4-spirocyclopentane-1-[4-(α-(5-tetrazolyl)-benzyloxy)benzyl]-2-imidazolin-5-one.

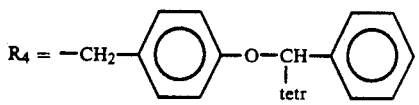

A) 2-[4-((2-n-butyl-5-oxo-4-spirocyclopentane-2-imidazolin-1-yl)methyl)phenoxy]-2-phenylacetic acid chloride.

163 mg of the acid prepared in Example 32 and 0.5 ml of thionyl chloride are mixed in 5 ml of DCM and the mixture is stirred at RT for 18 hours. The mixture is concentrated to dryness, taken up with toluene and then concentrated again and taken up with ether. After concentrating the solvent, the residue is used such as it is in the following stage.

B) 2-[4-((2-n-Butyl-5-oxo-4-spirocyclopentane-2-imidazolin-1-yl)methyl)phenoxy]-2-phenylacetic.

The compound prepared previously is taken up in 1 ml of THF and the solution is introduced into a metal cylinder; 6 ml of previously liquefied gaseous ammonia are introduced and the metal cylinder is closed. After 18 hours at RT, the mixture is concentrated, taken up with dilute sodium hydroxide solution and extracted with ethyl acetate. After washing with water, chromatography is carried out on a silica column by eluting with a DCM/MeOH (97/3; v/v) mixture. 100 mg of the expected product are obtained.

C) 2-n-Butyl-1-[4-(α-cyanobenzyloxy)benzyl]-4-spirocyclopentane-2-imidazolin-5-one.

A mixture of 120 mg of the compound obtained previously and 6 ml of phosphorus oxychloride is brought to reflux for 4 hours. The reaction mixture is concentrated, extracted with ethyl acetate and then washed with water. The product obtained is used such as it is in the following stage.

D) 2-n-Butyl-4-spirocyclopentane-1-[4-(α-(5-tetrazolyl)benzyloxy)benzyl]-2-imidazolin-5-one.

A mixture containing 80 mg of the product prepared in the preceding stage, 10 ml of toluene and 129 mg of tributyltin azide is brought to reflux for 96 hours. After cooling, the mixture is extracted with a 1N sodium hydroxide solution and is then washed with ether. The aqueous phase is acidified with a 3N hydrochloric acid solution. It is extracted with ethyl acetate, washed with water and then chromatographed on silica by eluting with a DCM/MeOH/AcOH (97/3/0.5; v/v/v) mixture. 19 mg of the expected product are obtained.

Mass Spectrum: MH+ = 459

NMR: 0.72 ppm: t: 3 H: C$\underline{H}_3$—CH$_2$—CH$_2$—CH$_2$—, 1.2 ppm: sext: 2 H: CH$_3$C$\underline{H}_2$—CH$_2$—CH$_2$—, 1.4 ppm: quint: 2 H: CH$_3$—CH$_2$—C$\underline{H}_2$—CH$_2$—, 1.5–1.9 ppm: m: 8 H: cyclopentane, 2.3 ppm: t: 2 H: CH$_3$—CH$_2$—CH$_2$—C$\underline{H}_2$—, 4.55 ppm: s: 2 H: N—C$\underline{H}_2$—C$_6$H$_4$—, 6.95 ppm: s: H: C$_\underline{H}$-tert, 7–7.6 ppm: m: 9 H: aromatic

We claim:

1. A compound of formula:

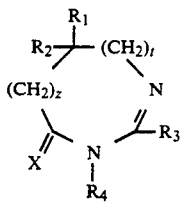

(1)

in which:

R$_1$ and R$_2$ each independently represent C$_1$–C$_6$ alkyl, C$_3$–C$_7$ cycloalkyl, phenyl or phenyl(C$_{1-3}$)alkyl wherein alkyl, phenyl and phenyl(1-3)alkyl are unsubstituted or substituted by one or more halogen atoms or by a group selected from the group consisting of C$_1$–C$_4$ perfluoroalkyl, hydroxyl and C$_1$–C$_4$ alkoxy;

or R$_1$ and R$_2$ together form a group =CR'$_1$R'$_2$, in which R'$_1$ represents hydrogen, C$_1$–C$_4$ alkyl or phenyl, and R'$_2$ represents C$_1$–C$_4$ alkyl or phenyl;

or R$_1$ and R$_2$ bonded together form a group —(CH$_2$)$_n$— or a group —(CH$_2$)$_p$Y(CH$_2$)$_q$—, in which Y is oxygen, sulphur, or CH substituted by C$_1$–C$_4$ alkyl, phenyl or phenyl(C$_{1-3}$)alkyl, or a group N—R$_5$ in which R$_5$ represents hydrogen, C$_1$–C$_4$ alkyl, phenyl(C$_{1-3}$)alkyl, C$_1$–C$_4$ alkylcarbonyl, C$_1$–C$_4$ haloalkylcarbonyl, C$_1$–C$_4$ polyhaloalkylcarbonyl, benzoyl, alpha aminoacyl or a N-protecting group, or R$_1$ and R$_2$ bonded together with the atom of carbon to which they are bonded form an indane or an adamantane;

R$_3$ represents hydrogen, C$_1$–C$_6$ alkyl which is unsubstituted or substituted by one or more halogen atoms; C$_2$–C$_6$ alkenyl; C$_3$–C$_7$ cycloalkyl; phenyl; phenyl(C$_{1-3}$)alkyl, phenyl(C$_{2-3}$)alkenyl, wherein the phenyl groups are unsubstituted or substituted one or more times by halogen, C$_1$–C$_4$ alkyl, C$_1$–C$_4$ haloalkyl, C$_1$–C$_4$ polyhaloalkyl, hydroxyl or C$_1$–C$_4$ alkoxy;

R$_4$ represents a group selected from the group consisting of:

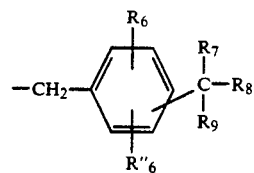  a)

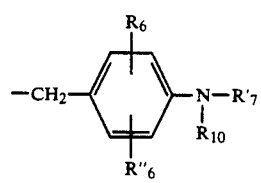  b)

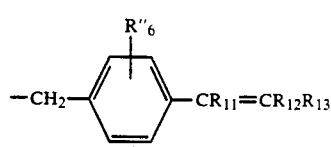  c)

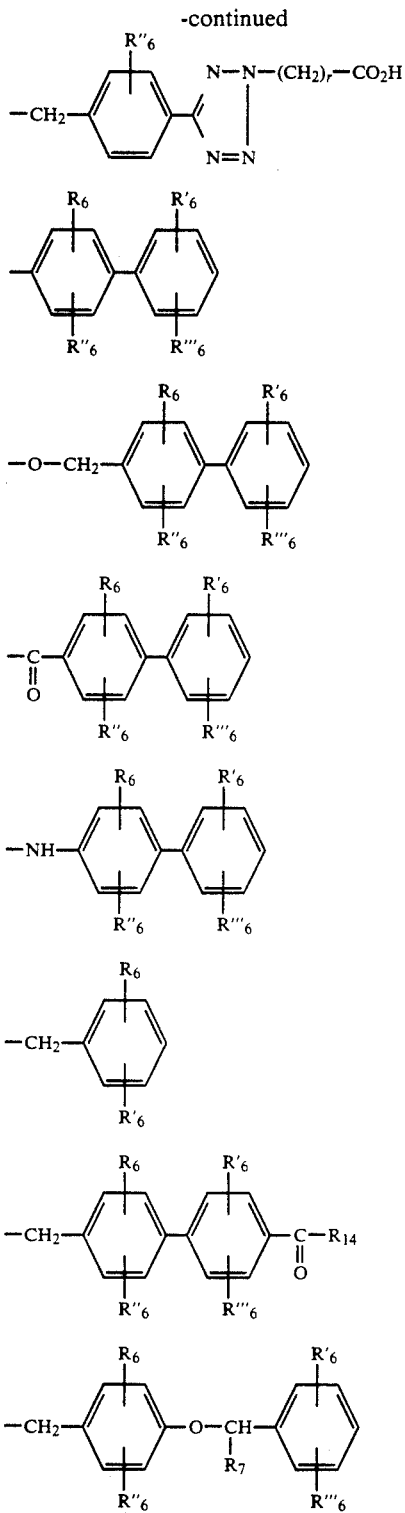

groups e, f, g, h, and j, at least one of the substituents $R_6$ or $R'_6$ is different from hydrogen;

$R_7$ represents $C_1$–$C_4$ alkyl or a group selected from:

$-(CH_2)_r-CO_2H$     i)

$-(CH_2)_r-\underset{\underset{N\diagdown N\diagup}{\|}}{\overset{}{\bigg|}}-NH$     ii)

$-\underset{CH_3}{\overset{CH_3}{\underset{|}{\overset{|}{C}}}}-\underset{\underset{N\diagdown N\diagup}{\|}}{\overset{}{\bigg|}}-NH$     iii)

$-(CH_2)_r-\underset{\underset{N\diagdown O\diagup}{\|}}{\overset{}{\bigg|}}-NH-C=O$     iv)

$-(CH_2)_r-N\underset{O=\underset{\underset{H}{N}}{C}}{\overset{\overset{}{\diagup}\diagdown}{\phantom{O}}}O$     v)

$-(CH_2)_r-\overset{O}{\overset{\|}{C}}-NHOH$     vi)

$-(CH_2)_r-CN$     vii)

$-OCOCH_3$     viii)

$R'_7$ represents $C_1$–$C_4$ alkyl or a group selected from:

$-(CH_2)_s-CO_2H$ $-(CH_2)_r-CN$ $-(CH_2)_r-\underset{NH}{\overset{\|}{C}}-OCH_3$ $-(CH_2)_r-\underset{\underset{N\diagdown N\diagup}{\|}}{\overset{}{\bigg|}}-NH$ $-\underset{CH_3}{\overset{CH_3}{\underset{|}{\overset{|}{C}}}}-\underset{\underset{N\diagdown N\diagup}{\|}}{\overset{}{\bigg|}}-NH$ $-(CH_2)_r-\underset{\underset{N\diagdown O\diagup}{\|}}{\overset{}{\bigg|}}-NH-C=O$ $-(CH_2)_r-N\underset{O=\underset{\underset{H}{N}}{C}}{\overset{\overset{}{\diagup}\diagdown}{\phantom{O}}}O$ wherein $R''_6$ and $R'''_6$ are similar or different and each independently represents hydrogen, chlorine, or a group selected from $C_1$–$C_6$ alkyl, $C_1$–$C_4$ alkoxy, amino and aminomethyl;

$R_6$ and $R'_6$ are similar or different and each independently represents hydrogen, carboxy, $C_1$–$C_4$ alkoxycarbonyl, cyano, 5-tetrazolyl, 5-methyltetrazolyl, 4H-5-oxo-1,2,4-oxadiazol-3-yl, or 4H-3,5-dioxo-1,2,4-oxadiazol-2-yl, with the proviso that for the $R_8$ is identical to $R_7$, or $R_8$ represents hydrogen, a halogen atom, $C_1$–$C_4$ alkyl, $C_3$–$C_7$ cycloalkyl, phenyl substituted by $R'_6$, benzyl in the phenyl is substituted by $R'_6$, hydroxyl, $C_1$–$C_4$ alkoxy, cyano, a group $OCOR_{15}$ in which $R_{15}$ represents $C_1-C_4$ alkyl, $C_1-C_4$ haloalkyl or phenyl substituted by $R'_6$;

$R_9$ is hydrogen or $R_9$ is identical to $R_8$, with the proviso that $R_9$ cannot be identical to $R_7$;

or $R_8$ and $R_9$ together with the carbon atom to which they are bonded form $C_3-C_7$ cycloalkyl or a carbonyl group;

$R_{10}$ represents hydrogen, $C_1-C_4$ alkyl, $C_3-C_7$ cycloalkyl, phenyl substituted by $R'_6$ or benzyl in which the phenyl is substituted by $R'_6$;

$R_{11}$ represents hydrogen, $C_1-C_6$ alkyl, carboxy, $C_1-C_4$ alkoxycarbonyl, 5-tetrazolyl, 4H-5-oxo-1,2,4-oxadiazol-3-yl, or 4H-3,5-dioxo-1,2,4-oxadiazol-2-yl;

$R_{12}$ represents hydrogen, $C_1-C_6$ alkyl, cyano, carboxy, $C_1-C_4$ alkoxycarbonyl, 5-tetrazolyl, phenyl substituted by $R'_6$, or benzyl in which the phenyl is substituted by $R'_6$;

$R_{13}$ represents hydrogen, $C_1-C_6$ alkyl, $C_1-C_4$ alkoxycarbonyl, phenyl substituted by $R'_6$, benzyl in which the phenyl is substituted by $R'_6$, cyano, carboxy, 5-tetrazolyl, 4H-5-oxo-1,2,4-oxadiazol-3-yl or 4H-3,5-dioxo-1,2,4-oxadiazol-2-yl, with the proviso that $T_{11}$ and $R_{13}$ do not simultaneously represent carboxy, 5-tetrazolyl, 4H-5-oxo-1,2,4-oxadiazol-3-yl or 4H-3,5-dioxo-1,2,4-oxadiazol-2-yl; and $R_{14}$ represents $C_1-C_4$ carboxyalkyl, phenyl or carboxyphenyl;

$p+q=m$;

n is an integer between 2 and 11;

m is an integer between 2 and 5;

r represents 0, 1 or 2;

s represents 1 or 2;

X represents an oxygen atom or a sulphur atom; and z and t are zero or one is zero and the other represents 1;

with the limitation that for the values a), b), k) and l) of $R_4$, $R_6$ represents hydrogen when $R_7$, $R'_7$ or $R_{14}$ contains carboxy, 5-tetrazolyl, 4H-5-oxo-1,2,4-oxadiazol-3-yl or 4H-3,5-dioxo-1,2,4-oxadiazol-2-yl; and its salts.

2. A compound according to claim 1 in which $R_1$ and $R_2$ together with the carbon to which they are bonded form cyclopentane or cyclohexane.

3. A compound according to claim 1 in which one of $R_1$ and $R_2$ is methyl and the other is cyclohexyl.

4. A compound according to claim 1 in which $R_3$ represents linear $C_1-C_6$ alkyl.

5. A compound according to claim 1 in which X represents an oxygen atom.

6. A compound according to claim 1 in which $R_4$ represents a group of formula:

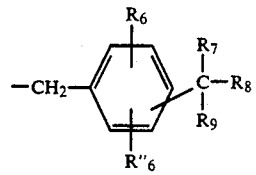

in which $R_6$, $R''_6$, $R_7$, $R_8$ and $R_9$ are as defined in claim 1.

7. A compound according to claim 6 in which $R_6$ and $R''_6$ represent hydrogen and $R_7$ represents a group $—(CH_2)_r—COOH$ wherein r is 0, 1 or 2.

8. A pharmaceutical composition comprising as active ingredient a compound according to claim 1.

9. A pharmaceutical composition comprising a compound according to claim 1 in combination with a beta-blocker.

10. A pharmaceutical composition comprising a compound according to claim 1 in combination with a diuretic.

11. A pharmaceutical composition comprising a compound according to claim 1 in combination with a non-steroidal antiinflammatory.

12. A pharmaceutical composition comprising a compound according to claim 1 in combination with a calcium antagonist.

13. A pharmaceutical composition comprising a compound according to claim 1 in combination with a tranquilizer.

* * * * *